US010752921B2

(12) United States Patent
Bhuiya et al.

(10) Patent No.: US 10,752,921 B2
(45) Date of Patent: Aug. 25, 2020

(54) ENZYMES AND METHODS FOR STYRENE SYNTHESIS

(71) Applicant: Phytogene, Inc., Rancho Santa Margarita, CA (US)

(72) Inventors: Mohammad Wadud Bhuiya, St. Louis, MO (US); Hui Chen, Bedford, MA (US); Xianpeng Cai, St. Louis, MO (US); Jixiang Han, Maryland Heights, MO (US); Xiaodan Yu, Lexington, MA (US)

(73) Assignee: Phytogene, Inc., Rancho Santa Margarita, CA (US)

( * ) Notice: Subject to any disclaimer, the term of this patent is extended or adjusted under 35 U.S.C. 154(b) by 42 days.

(21) Appl. No.: 15/705,361

(22) Filed: Sep. 15, 2017

(65) Prior Publication Data
US 2018/0002726 A1  Jan. 4, 2018

Related U.S. Application Data

(62) Division of application No. 14/409,600, filed as application No. PCT/US2013/047098 on Jun. 21, 2013, now abandoned.

(Continued)

(51) Int. Cl.
*C12N 1/16* (2006.01)
*C12N 1/20* (2006.01)
(Continued)

(52) U.S. Cl.
CPC ............... *C12P 5/005* (2013.01); *C12N 1/16* (2013.01); *C12N 1/20* (2013.01); *C12N 9/88* (2013.01);
(Continued)

(58) Field of Classification Search
None
See application file for complete search history.

(56) References Cited

U.S. PATENT DOCUMENTS

2007/0259409 A1  11/2007  Wery
2009/0311760 A1  12/2009  Wery et al.
(Continued)

FOREIGN PATENT DOCUMENTS

CN  101397568  4/2009
CN  103865912  6/2014
(Continued)

OTHER PUBLICATIONS

UniProt Accession No. G3Y7U5_ASPNA, published Dec. 14, 2011 (Year: 2011).*

(Continued)

*Primary Examiner* — Richard C Ekstrom
(74) *Attorney, Agent, or Firm* — Wolf, Greenfield & Sacks, P.C.; Karen K. Chan

(57) ABSTRACT

The subject technology generally relates to biosynthesis of styrene. Certain embodiments of the subject technology is based, in part, on the recognition that phenylalanine can be converted to styrene by a two-step pathway of deamination and de-carboxylation, with trans-cinnamic acid (tCA) as the intermediate. Two types of enzymes are directly involved in this process, phenylalanine ammonia lyase (PAL), which converts phenylalanine to tCA, and cinnamic acid decarboxylase, which coverts tCA to styrene. Host cells expressing these two types of enzymes can be cultured in bioreactor to produce styrene from renewable substrates such as glucose.

20 Claims, 21 Drawing Sheets
Specification includes a Sequence Listing.

Related U.S. Application Data

(60) Provisional application No. 61/663,500, filed on Jun. 22, 2012.

(51) Int. Cl.
  *C12N 9/88* (2006.01)
  *C12P 5/00* (2006.01)
  *C12Q 1/527* (2006.01)

(52) U.S. Cl.
  CPC ...... *C12Q 1/527* (2013.01); *C12Y 403/01024* (2013.01); *C07K 2319/00* (2013.01); *C12Y 401/01* (2013.01); *C12Y 403/01005* (2013.01)

(56) References Cited

U.S. PATENT DOCUMENTS

2015/0337336 A1  11/2015  Bhuiya et al.
2018/0002726 A1* 1/2018  Bhuiya ................ C12Q 1/527

FOREIGN PATENT DOCUMENTS

WO  WO 1994/008036 A1  4/1994
WO  WO 2012/122333 A1  9/2012
WO  WO 2014/202838 A1  12/2014

OTHER PUBLICATIONS

PCT/US2013/047098, dated Dec. 31, 2013, Invitation to Pay Additional Fees.
PCT/US2013/047098, dated Mar. 7, 2014, International Search Report and Written Opinion.
PCT/US2013/047098, dated Dec. 31, 2014, International Preliminary Report on Patentability.
EP 13806939.8, dated Apr. 13, 2015, Extended European Search Report.
EBI Accession No. BBS07607. Dec. 24, 2014.
[No Author Listed], SIGMA. Additive Screening Kit datasheet. Buchs, Switzerland. 2010;109:564-569.
Bhuiya et al., Structure and Mechanism of Ferulic Acid Decarboxylase (FDC1) from *Saccharomyces cerevisiae*. Appl Environ Microbiol. Jun. 15, 2015;81(12):4216-23. doi: 10.1128/AEM.00762-15.
Cochrane et al., The *Arabidopsis phenylalanine* ammonia lyase gene family: kinetic characterization of the four PAL isoforms. Phytochemistry. Jun. 2004;65(11):1557-64.
EBI Accession No. BB207607. Dec. 24, 2014.
Genbank Accession No. AAM15324.1. Feb. 27, 2002.
Genbank Accession No. NP_010828.1. NCBI. Jacq et al. Apr. 26, 2011.
Genbank Accession No. NP_181241. Lin et al. May 28, 2011.
Genbank Accession No. NP_190894.1. May 28, 2011.
Genbank Accession No. XM_002421083. Jackson et al. Jun. 26, 2009.
Hampton Research Corp., Temperature As A Crystallization Variable. California, U.S.A. 2001.
Huang et al., [Recent progress in fusion enzyme design and applications]. Sheng Wu Gong Cheng Xue Bao. Apr. 2012;28(4):393-409.
Huang et al., An endogenous factor enhances ferulic acid decarboxylation catalyzed by phenolic acid decarboxylase from Candida guilliermondii. AMB Express. Jan. 4, 2012;2(1):4. doi:10.1186/2191-0855-2-4.
McKenna et al., Styrene biosynthesis from glucose by engineered *E. coli*. Metab Eng. Sep. 2011;13(5):544-54. doi: 10.1016/j.ymben.2011.06.005. Epub Jun. 23, 2011.
Mukai et al., PAD1 and FDC1 are essential for the decarboxylation of phenylacrylic acids in *Saccharomyces cerevisiae*. J Biosci Bioeng. Jun. 2010;109(6):564-9. doi: 10.1016/j.jbiosc.2009.11.011. Epub Dec. 16, 2009.
Rangarajan et al., Crystal structure of a dodecameric FMN-dependent UbiX-like decarboxylase (Pad1) from *Escherichia coli* O157: H7. Protein Sci. Nov. 2004;13(11):3006-16. Epub Sep. 30, 2004.
Registry of Standard Biological Parts: Protein domains/Linker. International Genetically Engineered Machine (iGEM) Foundation, 2008-2011. Retrieved from the Internet Feb. 20, 2014.
Seo et al., Characterization of a bifunctional enzyme fusion of trehalose-6-phosphate synthetase and trehalose-6-phosphate phosphatase of *Escherichia coli*. Appl Environ Microbiol. Jun. 2000;66(6):2484-90.
SIGMA, Additive Screening Kit. Buchs, Switzerland. 2004;1.
Smits et al., A structural basis for substrate selectivity and stereoselectivity in octopine dehydrogenase from Pecten maximus. J Mol Biol. Aug. 1, 2008;381(1):200-11. doi: 10.1016/j.jmb.2008.06.003. Epub Jun. 7, 2008.
UniProt accession No. Q03034; May 31, 2011.
UniProt accession No. Q6BJQ8_DEBHA; May 31, 2011.
UniProt Ebi accession No. A2QHE5; Mar. 6, 2007.
UniProt Ebi accession No. I1RL84. Jun. 13, 2012.
UniProtKB Accession No. B9WJ66; Jackson et al. Mar. 24, 2009.
Zhang et al., Using unnatural protein fusions to engineer resveratrol biosynthesis in yeast and Mammalian cells. J Am Chem Soc. Oct. 11, 2006;128(40):13030-1.

* cited by examiner

```
                              SEQUENCE LISTING

<160> NUMBER OF SEQ ID NOS: 44

<210> SEQ ID NO 1
<211> LENGTH: 2178
<212> TYPE: DNA
<213> ORGANISM: Arabidopsis thaliana

<400> SEQUENCE: 1
atggagatta   acggggcaca   caagagcaac   ggaggaggag   tggacgctat   gttatgcggc      60
ggagacatca   agacaaagaa   catggtgatc   aacgcggagg   atcctctcaa   ctggggagct     120
gcagcggagc   aaatgaaagg   tagccatttg   gatgaagtga   agagaatggt   tgctgagttt     180
aggaagccag   ttgtgaatct   tggtggtgag   actctgacca   ttggacaagt   ggctgcgatc     240
tcaactattg   gtaacagtgt   gaaggtggag   ctatcggaga   cagctagagc   cggtgtgaat     300
gctagtagtg   attgggttat   ggagagtatg   aacaaaggca   ctgatagtta   tggtgttact     360
actggttttg   gtgctacttc   tcatcggaga   accaaaaacg   gtgtcgcact   tcagaaggaa     420
cttattagat   tccttaacgc   cggaatattc   ggaagcacga   agaaacaag    ccacacattg     480 ccacactccg   ccacaagagc   cgccatgctt   gtacgaatca   acactctcct   ccaaggattt     540
tccggtatcc   gatttgagat   tctcgaagca   attaccagtt   tcctcaacaa   caacatcact     600
ccatctctcc   ccctccgtgg   tacaatcacc   gcctccggag   atctcgttcc   tctctcctac     660
atcgccggac   ttctcaccgg   tcgtcccaat   tccaaagcta   ctggtcccaa   cggtgaagct     720
ttaacagcag   aggaagcttt   caaattagca   ggaatcagct   ccggattctt   tgatctccag     780
cctaaggaag   gtctcgcgct   agtcaatggc   acggcggttg   gatctggaat   ggcgtcaatg     840
gtgttattcg   aaacgaatgt   tctctctgtt   ttggctgaga   ttttgtcggc   ggttttcgca     900
gaggtgatga   gtggtaagcc   tgagttcacc   gatcatctca   ctcacagact   taaacatcat     960
cccggtcaaa   tcgaagcggc   ggcgataatg   gagcatatcc   tcgacggaag   ctcgtacatg    1020
aaattagctc   agaagcttca   cgagatggat   ccgttacaga   aacctaaaca   agatcgttac    1080
gctcttcgta   cttctcctca   atggttaggt   cctcaaatcg   aagtgatccg   ttacgcaacg    1140
aaatcgatcg   agcgtgagat   taactccgtc   aacgataatc   cgttgatcga   tgtttcgagg    1200
aacaaggcga   ttcacggtgg   taacttccaa   ggaacaccaa   tcggagtttc   aatggataac    1260
acgagattgg   cgatagcagc   gattggtaaa   ctcatgtttg   ctcaattctc   agagcttgtg    1320
aatgatttct   acaacaatgg   tttaccctcg   aatctaaccg   cttcgaggaa   tccaagtttg    1380
gattatggat   tcaagggagc   tgagattgca   atggcttctt   attgttcaga   gcttcaatac    1440
ttagctaatc   ctgtgactag   ccatgttcaa   tcagcagagc   aacataacca   agatgtcaac    1500
tctttgggac   taatctcgtc   tcgcaaaact   tctgaagctg   ttgatattct   caagcttatg    1560
tcaacaacgt   tcctcgttgc   gatttgtcaa   gctgtggatt   tgagacattt   ggaggagaat    1620
ttgagacaga   ctgtgaagaa   cactgtctct   caagtggcga   agaaagttct   tactactgga    1680
gtcaatggtg   agcttcatcc   ttctcgcttc   tgcgaaaagg   atttactcaa   agttgtagac    1740
```

```
cgtgaacaag tctacacata cgcggatgat ccttgtagcg caacgtaccc gttgattcag    1800
aagctgagac aagttattgt tgaccatgct ttgatcaatg gtgagagtga aagaatgca     1860 gtgacttcaa tcttccataa gattggagct ttcgaggagg agcttaaggc agtgctaccg    1920
aaagaagtgg aagcagcaag agcagcctac gataacggaa catcggctat cccgaacagg    1980
atcaaggaat gtaggtcgta tccattgtat agattcgtga gggaagagct tggaacagag    2040
cttttgaccg gagagaaagt gacgtcgcct ggagaagagt tcgacaaggt tttcacggcg    2100
atttgtgaag gtaaaatcat tgatccgatg atggaatgtc tcaacgagtg gaacggagct    2160
cccattccaa tatgttaa                                                  2178
```

<210> SEQ ID NO 2
<211> LENGTH: 725
<212> TYPE: PRT
<213> ORGANISM: Arabidopsis thaliana

<400> SEQUENCE: 2

```
Met Glu Ile Asn Gly Ala His Lys Ser Asn Gly Gly Gly Val Asp Ala
 1               5                  10                  15

Met Leu Cys Gly Gly Asp Ile Lys Thr Lys Asn Met Val Ile Asn Ala
            20                  25                  30

Glu Asp Pro Leu Asn Trp Gly Ala Ala Ala Glu Gln Met Lys Gly Ser
        35                  40                  45

His Leu Asp Glu Val Lys Arg Met Val Ala Glu Phe Arg Lys Pro Val
    50                  55                  60

Val Asn Leu Gly Gly Glu Thr Leu Thr Ile Gly Gln Val Ala Ala Ile
65                  70                  75                  80

Ser Thr Ile Gly Asn Ser Val Lys Val Glu Leu Ser Glu Thr Ala Arg
                85                  90                  95

Ala Gly Val Asn Ala Ser Ser Asp Trp Val Met Glu Ser Met Asn Lys
            100                 105                 110

Gly Thr Asp Ser Tyr Gly Val Thr Thr Gly Phe Gly Ala Thr Ser His
        115                 120                 125

Arg Arg Thr Lys Asn Gly Val Ala Leu Gln Lys Glu Leu Ile Arg Phe
    130                 135                 140

Leu Asn Ala Gly Ile Phe Gly Ser Thr Lys Glu Thr Ser His Thr Leu
145                 150                 155                 160

Pro His Ser Ala Thr Arg Ala Ala Met Leu Val Arg Ile Asn Thr Leu
                165                 170                 175

Leu Gln Gly Phe Ser Gly Ile Arg Phe Glu Ile Leu Glu Ala Ile Thr
            180                 185                 190

Ser Phe Leu Asn Asn Asn Ile Thr Pro Ser Leu Pro Leu Arg Gly Thr
        195                 200                 205

Ile Thr Ala Ser Gly Asp Leu Val Pro Leu Ser Tyr Ile Ala Gly Leu
    210                 215                 220

Leu Thr Gly Arg Pro Asn Ser Lys Ala Thr Gly Pro Asn Gly Glu Ala
225                 230                 235                 240

Leu Thr Ala Glu Glu Ala Phe Lys Leu Ala Gly Ile Ser Ser Gly Phe
                245                 250                 255

Phe Asp Leu Gln Pro Lys Glu Gly Leu Ala Leu Val Asn Gly Thr Ala
            260                 265                 270

Val Gly Ser Gly Met Ala Ser Met Val Leu Phe Glu Thr Asn Val Leu
        275                 280                 285

Ser Val Leu Ala Glu Ile Leu Ser Ala Val Phe Ala Glu Val Met Ser
```

-continued

```
            290                 295                 300
Gly Lys Pro Glu Phe Thr Asp His Leu Thr His Arg Leu Lys His His
305                 310                 315                 320

Pro Gly Gln Ile Glu Ala Ala Ile Met Glu His Ile Leu Asp Gly
                325                 330                 335

Ser Ser Tyr Met Lys Leu Ala Gln Lys Leu His Glu Met Asp Pro Leu
                340                 345                 350

Gln Lys Pro Lys Gln Asp Arg Tyr Ala Leu Arg Thr Ser Pro Gln Trp
                355                 360                 365

Leu Gly Pro Gln Ile Glu Val Ile Arg Tyr Ala Thr Lys Ser Ile Glu
            370                 375                 380

Arg Glu Ile Asn Ser Val Asn Asp Asn Pro Leu Ile Asp Val Ser Arg
385                 390                 395                 400

Asn Lys Ala Ile His Gly Gly Asn Phe Gln Gly Thr Pro Ile Gly Val
                405                 410                 415

Ser Met Asp Asn Thr Arg Leu Ala Ile Ala Ala Ile Gly Lys Leu Met
                420                 425                 430

Phe Ala Gln Phe Ser Glu Leu Val Asn Asp Phe Tyr Asn Asn Gly Leu
                435                 440                 445

Pro Ser Asn Leu Thr Ala Ser Arg Asn Pro Ser Leu Asp Tyr Gly Phe
            450                 455                 460

Lys Gly Ala Glu Ile Ala Met Ala Ser Tyr Cys Ser Glu Leu Gln Tyr
465                 470                 475                 480

Leu Ala Asn Pro Val Thr Ser His Val Gln Ser Ala Glu Gln His Asn
                485                 490                 495

Gln Asp Val Asn Ser Leu Gly Leu Ile Ser Ser Arg Lys Thr Ser Glu
                500                 505                 510

Ala Val Asp Ile Leu Lys Leu Met Ser Thr Thr Phe Leu Val Ala Ile
                515                 520                 525

Cys Gln Ala Val Asp Leu Arg His Leu Glu Glu Asn Leu Arg Gln Thr
530                 535                 540

Val Lys Asn Thr Val Ser Gln Val Ala Lys Lys Val Leu Thr Thr Gly
545                 550                 555                 560

Val Asn Gly Glu Leu His Pro Ser Arg Phe Cys Glu Lys Asp Leu Leu
                565                 570                 575

Lys Val Val Asp Arg Glu Gln Val Tyr Thr Tyr Ala Asp Asp Pro Cys
                580                 585                 590

Ser Ala Thr Tyr Pro Leu Ile Gln Lys Leu Arg Gln Val Ile Val Asp
                595                 600                 605

His Ala Leu Ile Asn Gly Glu Ser Glu Lys Asn Ala Val Thr Ser Ile
            610                 615                 620

Phe His Lys Ile Gly Ala Phe Glu Glu Leu Lys Ala Val Leu Pro
625                 630                 635                 640

Lys Glu Val Glu Ala Ala Arg Ala Ala Tyr Asp Asn Gly Thr Ser Ala
                645                 650                 655

Ile Pro Asn Arg Ile Lys Glu Cys Arg Ser Tyr Pro Leu Tyr Arg Phe
                660                 665                 670

Val Arg Glu Glu Leu Gly Thr Glu Leu Leu Thr Gly Glu Lys Val Thr
            675                 680                 685

Ser Pro Gly Glu Glu Phe Asp Lys Val Phe Thr Ala Ile Cys Glu Gly
            690                 695                 700

Lys Ile Ile Asp Pro Met Met Glu Cys Leu Asn Glu Trp Asn Gly Ala
705                 710                 715                 720
```

Pro Ile Pro Ile Cys
            725

<210> SEQ ID NO 3
<211> LENGTH: 2154
<212> TYPE: DNA
<213> ORGANISM: Arabidopsis thaliana

<400> SEQUENCE: 3

| | | | | | |
|---|---|---|---|---|---|
| atggatcaaa | tcgaagcaat | gttgtgcggc | ggaggagaga | agacaaaagt | ggcggttact | 60 |
| acgaagactt | tggcagatcc | attgaattgg | ggtttagcag | cggatcaaat | gaaaggaagt | 120 |
| catttagatg | aagtgaagaa | gatggtcgaa | gagtatcgta | gaccagtcgt | gaatcttggc | 180 |
| ggagaaacac | tgacgatcgg | acaagttgct | gccatctcca | ccgtaggagg | cagcgttaag | 240 |
| gttgagttag | cggagacttc | aagagccggt | gtgaaagcta | gcagtgattg | ggttatggag | 300 |
| agcatgaaca | aggtactga | cagttacgga | gtcaccaccg | gctttggtgc | tacttctcac | 360 |
| cggagaacca | aaaacggcac | cgcattacaa | acagaactca | ttagattttt | gaacgccgga | 420 |
| atattcggaa | acacgaagga | gacatgtcac | acactgccgc | aatccgccac | aagagccgcc | 480 |
| atgctcgtca | gagtcaacac | tcttctccaa | ggatactccg | ggatccgatt | cgagatcctc | 540 |
| gaagcgatta | caagtctcct | caaccacaac | atctctccgt | cactacctct | ccgtggaacc | 600 |
| attaccgcct | ccggcgatct | cgttcctctc | tcttacatcg | ccggacttct | caccggccgt | 660 |
| cctaattcca | agccaccgg | tcccgacggt | gaatcgctaa | ccgcgaaaga | agcttttgag | 720 |
| aaagccggaa | tcagtactgg | attcttcgat | tacaacctta | ggaaggtttt | agctctcgtt | 780 |
| aatggcacgg | cggttggatc | tggaatggcg | tcgatggttc | tattcgaagc | gaatgtccaa | 840 |
| gcggtgttag | cggaggtttt | atcagcgatc | ttcgcggagg | ttatgagcgg | aaaacctgag | 900 |
| tttaccgatc | atctgactca | tcgtttaaaa | catcatcccg | acaaatcga | agcggcggcg | 960 |
| ataatggagc | acatactcga | cggaagctca | tacatgaaat | tagctcaaaa | ggttcacgag | 1020 |
| atggatccat | tgcagaaacc | aaaacaagat | cgttacgctc | ttcgtacatc | tcctcaatgg | 1080 |
| ctaggtcctc | aaattgaagt | aatccgtcaa | gctacgaaat | cgatagagcg | tgaaatcaac | 1140 |
| tccgttaacg | ataatccgtt | gatcgatgtt | tcgaggaaca | aggcgattca | cggtggtaac | 1200 |
| ttccaaggaa | caccaatcgg | agtttctatg | gataacacga | gattggcgat | gctgcgatt | 1260 |
| gggaagctaa | tgtttgctca | attctctgag | cttgttaatg | atttctacaa | caatggactt | 1320 |
| ccttcgaatc | taactgcttc | gagtaatcca | agtttggatt | atggattcaa | aggagcagag | 1380 |
| attgctatgg | cttcttattg | ttctgagctt | caatacttgg | ctaatccagt | cacaagccat | 1440 |
| gttcaatcag | ctgagcaaca | taatcaagat | gtgaactctc | ttggtttgat | ctcgtctcgt | 1500 |
| aaaacatctg | aagctgtgga | tattcttaag | ctaatgtcaa | caacgttcct | tgtggggata | 1560 |
| tgtcaagctg | ttgatttgag | acatttggag | gagaatctga | acaaactgt | gaagaacaca | 1620 |
| gtttctcaag | ttgctaagaa | agtgttaacc | actggaatca | acggtgagtt | acatccgtca | 1680 |
| aggttttgcg | agaaggactt | gcttaaggtt | gttgatcgtg | agcaagtgtt | cacgtatgtg | 1740 |
| gatgatcctt | gtagcgctac | gtacccgttg | atgcagagac | taagacaagt | tattgttgat | 1800 |
| cacgctttgt | ccaacggtga | gactgagaag | aatgcagtga | cttcgatctt | tcaaaagatt | 1860 |
| ggagcttttg | aagaggagct | taaggctgtg | cttccaaagg | aagttgaagc | ggctagagcg | 1920 |
| gcttatggga | atggaactgc | gccgattcct | aaccggatta | ggaatgtag | gtcgtatccg | 1980 |
| ttgtataggt | tcgtgaggga | agagcttgga | acgaagttgt | tgactggaga | aaaggttgtg | 2040 |

```
tctccgggag aggagtttga taaggtcttc actgctatgt gtgaaggtaa acttattgat    2100
ccgttgatgg attgtctcaa ggaatggaac ggagctccga ttccgatttg ctaa          2154
```

<210> SEQ ID NO 4
<211> LENGTH: 717
<212> TYPE: PRT
<213> ORGANISM: Arabidopsis thaliana

<400> SEQUENCE: 4

```
Met Asp Gln Ile Glu Ala Met Leu Cys Gly Gly Glu Lys Thr Lys
1               5                   10                  15

Val Ala Val Thr Thr Lys Thr Leu Ala Asp Pro Leu Asn Trp Gly Leu
            20                  25                  30

Ala Ala Asp Gln Met Lys Gly Ser His Leu Asp Glu Val Lys Lys Met
        35                  40                  45

Val Glu Glu Tyr Arg Arg Pro Val Val Asn Leu Gly Gly Glu Thr Leu
    50                  55                  60

Thr Ile Gly Gln Val Ala Ala Ile Ser Thr Val Gly Gly Ser Val Lys
65                  70                  75                  80

Val Glu Leu Ala Glu Thr Ser Arg Ala Gly Val Lys Ala Ser Ser Asp
                85                  90                  95

Trp Val Met Glu Ser Met Asn Lys Gly Thr Asp Ser Tyr Gly Val Thr
            100                 105                 110

Thr Gly Phe Gly Ala Thr Ser His Arg Arg Thr Lys Asn Gly Thr Ala
        115                 120                 125

Leu Gln Thr Glu Leu Ile Arg Phe Leu Asn Ala Gly Ile Phe Gly Asn
    130                 135                 140

Thr Lys Glu Thr Cys His Thr Leu Pro Gln Ser Ala Thr Arg Ala Ala
145                 150                 155                 160

Met Leu Val Arg Val Asn Thr Leu Leu Gln Gly Tyr Ser Gly Ile Arg
                165                 170                 175

Phe Glu Ile Leu Glu Ala Ile Thr Ser Leu Leu Asn His Asn Ile Ser
            180                 185                 190

Pro Ser Leu Pro Leu Arg Gly Thr Ile Thr Ala Ser Gly Asp Leu Val
        195                 200                 205

Pro Leu Ser Tyr Ile Ala Gly Leu Leu Thr Gly Arg Pro Asn Ser Lys
    210                 215                 220

Ala Thr Gly Pro Asp Gly Glu Ser Leu Thr Ala Lys Glu Ala Phe Glu
225                 230                 235                 240

Lys Ala Gly Ile Ser Thr Gly Phe Phe Asp Leu Gln Pro Lys Glu Gly
                245                 250                 255

Leu Ala Leu Val Asn Gly Thr Ala Val Gly Ser Gly Met Ala Ser Met
            260                 265                 270

Val Leu Phe Glu Ala Asn Val Gln Ala Val Leu Ala Glu Val Leu Ser
        275                 280                 285

Ala Ile Phe Ala Glu Val Met Ser Gly Lys Pro Glu Phe Thr Asp His
    290                 295                 300

Leu Thr His Arg Leu Lys His His Pro Gly Gln Ile Glu Ala Ala Ala
305                 310                 315                 320

Ile Met Glu His Ile Leu Asp Gly Ser Ser Tyr Met Lys Leu Ala Gln
                325                 330                 335

Lys Val His Glu Met Asp Pro Leu Gln Lys Pro Lys Gln Asp Arg Tyr
            340                 345                 350
```

Ala Leu Arg Thr Ser Pro Gln Trp Leu Gly Pro Gln Ile Glu Val Ile
        355                 360                 365

Arg Gln Ala Thr Lys Ser Ile Glu Arg Glu Ile Asn Ser Val Asn Asp
    370                 375                 380

Asn Pro Leu Ile Asp Val Ser Arg Asn Lys Ala Ile His Gly Gly Asn
385                 390                 395                 400

Phe Gln Gly Thr Pro Ile Gly Val Ser Met Asp Asn Thr Arg Leu Ala
                405                 410                 415

Ile Ala Ala Ile Gly Lys Leu Met Phe Ala Gln Phe Ser Glu Leu Val
            420                 425                 430

Asn Asp Phe Tyr Asn Asn Gly Leu Pro Ser Asn Leu Thr Ala Ser Ser
        435                 440                 445

Asn Pro Ser Leu Asp Tyr Gly Phe Lys Gly Ala Glu Ile Ala Met Ala
    450                 455                 460

Ser Tyr Cys Ser Glu Leu Gln Tyr Leu Ala Asn Pro Val Thr Ser His
465                 470                 475                 480

Val Gln Ser Ala Glu Gln His Asn Gln Asp Val Asn Ser Leu Gly Leu
                485                 490                 495

Ile Ser Ser Arg Lys Thr Ser Glu Ala Val Asp Ile Leu Lys Leu Met
            500                 505                 510

Ser Thr Thr Phe Leu Val Gly Ile Cys Gln Ala Val Asp Leu Arg His
        515                 520                 525

Leu Glu Glu Asn Leu Arg Gln Thr Val Lys Asn Thr Val Ser Gln Val
    530                 535                 540

Ala Lys Lys Val Leu Thr Thr Gly Ile Asn Gly Glu Leu His Pro Ser
545                 550                 555                 560

Arg Phe Cys Glu Lys Asp Leu Leu Lys Val Val Asp Arg Glu Gln Val
                565                 570                 575

Phe Thr Tyr Val Asp Asp Pro Cys Ser Ala Thr Tyr Pro Leu Met Gln
            580                 585                 590

Arg Leu Arg Gln Val Ile Val Asp His Ala Leu Ser Asn Gly Glu Thr
        595                 600                 605

Glu Lys Asn Ala Val Thr Ser Ile Phe Gln Lys Ile Gly Ala Phe Glu
    610                 615                 620

Glu Glu Leu Lys Ala Val Leu Pro Lys Glu Val Glu Ala Ala Arg Ala
625                 630                 635                 640

Ala Tyr Gly Asn Gly Thr Ala Pro Ile Pro Asn Arg Ile Lys Glu Cys
                645                 650                 655

Arg Ser Tyr Pro Leu Tyr Arg Phe Val Arg Glu Glu Leu Gly Thr Lys
            660                 665                 670

Leu Leu Thr Gly Glu Lys Val Val Ser Pro Gly Glu Glu Phe Asp Lys
        675                 680                 685

Val Phe Thr Ala Met Cys Glu Gly Lys Leu Ile Asp Pro Leu Met Asp
    690                 695                 700

Cys Leu Lys Glu Trp Asn Gly Ala Pro Ile Pro Ile Cys
705                 710                 715

<210> SEQ ID NO 5
<211> LENGTH: 2124
<212> TYPE: DNA
<213> ORGANISM: Arabidopsis thaliana

<400> SEQUENCE: 5
atggagctat gcaatcaaaa caatcacatc accgccgtct cgggcgatcc gttgaactgg    60

```
aacgcgacgg ccgaagcttt gaaagggagc cacctggatg aggtgaaacg aatggtgaaa      120
gagtatagga aagaggcggt gaagttagga ggtgagactt tgacgattgg tcaagtagcc      180
gccgtggcta gaggaggagg aggatctacg gtggagctag cggaggaggc tcgtgccgga      240
gtcaaggcga gtagcgaatg ggtgatggag agcatgaacc gaggaacgga cagttatgga      300
gttaccacag ggtttggtgc aacttcccat agaagaacca acaaggcggt gcacttcaa       360 aatgagctta ttaggttctt gaatgccgga atatttggcc ccggcgccgg ggacacgtca      420
cacacgttgc caaagccgac aacaagagcg gcaatgctcg tccgtgtcaa cactctcctc      480
caaggctact ccggtatacg cttcgagatt ctcgaagcaa ttacaaagct tctcaaccac      540
gaaatcactc cgtgcctccc tctccgtggc accatcaccg cctccggtga ccttgttcct      600
ctctcttaca cgccggact tctcactggc cgtcccaact ccaaagccgt gggtccctct       660
ggtgagactc tcactgcctc tgaggccttt aagctcgccg gagtatcgtc cttttcgag       720 ctgcagccta aggaaggact agcacttgtg aacgggacag cggttggatc gggtttggcc      780
tcaacggttt tgttcgatgc aaatattttg gctgttttat cggaagttat gtctgccatg      840
ttcgcagagg ttatgcaagg gaaaccggag tttacagatc atcttacgca taagctcaag      900
caccatcccg gtcagatcga agccgccgca attatgaaac atatattaga cggaagctct      960
tacgttaaag aagctcaact tctccacgaa atggatcctc ttcaaaaacc taaacaagat     1020
cggtacgctt tacgtacgtc accacaatgg cttgggccgc agattgaagt gatcagagcg     1080
gctactaaaa tgattgagcg tgagatcaac tctgttaatg ataaccctt gatagatgtg      1140 tcgaggaaca aggcgttgca cggtggaaat ttccaaggga caccgatcgg tgttgccatg     1200
gataattccc gtctagccat tgcttccatt gggaaactca tgtttgcgca gttttctgaa     1260
ctagtgaaca atttctacaa caatggtttg ccttctaatc tatctggtgg gagaaaccct     1320
agtcttgatt acgggtttaa aggcgcggaa atagccatgg cttcttattg ctccgagctt     1380
cagttcctgg ctaatcccgt gaccaaccat gtccaaagcg cagagcagca taaccaagac     1440
gttaattccc tagggctaat tctagcaggg aaaactgcag aagcagtgga tatcctcaag     1500
ctaatgtcca caacctactt agtcgcgctt tgccaagccg ttgatctaag acatcttgaa     1560
gagaatctga agaaggcggt taaatcagca gtgagtcagg tggcgaaacg ggtcttaacc     1620
gttggtgcca acggggagct acatccgtca aggttcacag aacgtgatgt cctccaagtg     1680
gttgaccgag agtacgtgtt ctcatacgca gacgatccct gcagcctcac ttacccgcta     1740
atgcagaaac ttagacacat tcttgtagac cacgctttag cggatccaga acgcgaggcc     1800
aattccgcga catcggtttt ccacaaaatc ggagcttttg aagccgagct gaaactgctt     1860
ctccctaaag aagtagaacg cgtccgggtt gaatacgagg aaggaacatc ggctatagct     1920
aaccggatta aggaatgtcg gtcttatcca ttgtatcggt ttgtccgcga tgagctaaat     1980
actgaactgc ttactggaga gaatgttcgg tcgccaggag aggagtttga taaagtgttc     2040
ttagcgattt ctgatggaaa acttattgat ccgttgttgg aatgtctcaa ggagtggaac     2100
ggagctccgg tttcaatctg ttga                                             2124
```

<210> SEQ ID NO 6
<211> LENGTH: 707
<212> TYPE: PRT
<213> ORGANISM: Arabidopsis thaliana

<400> SEQUENCE: 6

Met Glu Leu Cys Asn Gln Asn Asn His Ile Thr Ala Val Ser Gly Asp

```
  1               5                   10                  15
Pro Leu Asn Trp Asn Ala Thr Ala Glu Ala Leu Lys Gly Ser His Leu
                 20                  25                  30

Asp Glu Val Lys Arg Met Val Lys Glu Tyr Arg Lys Glu Ala Val Lys
                 35                  40                  45

Leu Gly Gly Glu Thr Leu Thr Ile Gly Gln Val Ala Ala Val Ala Arg
 50                  55                  60

Gly Gly Gly Gly Ser Thr Val Glu Leu Ala Glu Ala Arg Ala Gly
 65                  70                  75                  80

Val Lys Ala Ser Ser Glu Trp Val Met Glu Ser Met Asn Arg Gly Thr
                 85                  90                  95

Asp Ser Tyr Gly Val Thr Thr Gly Phe Gly Ala Thr Ser His Arg Arg
                 100                 105                 110

Thr Lys Gln Gly Gly Ala Leu Gln Asn Glu Leu Ile Arg Phe Leu Asn
                 115                 120                 125

Ala Gly Ile Phe Gly Pro Gly Ala Gly Asp Thr Ser His Thr Leu Pro
 130                 135                 140

Lys Pro Thr Thr Arg Ala Ala Met Leu Val Arg Val Asn Thr Leu Leu
145                 150                 155                 160

Gln Gly Tyr Ser Gly Ile Arg Phe Glu Ile Leu Glu Ala Ile Thr Lys
                 165                 170                 175

Leu Leu Asn His Glu Ile Thr Pro Cys Leu Pro Leu Arg Gly Thr Ile
                 180                 185                 190

Thr Ala Ser Gly Asp Leu Val Pro Leu Ser Tyr Ile Ala Gly Leu Leu
                 195                 200                 205

Thr Gly Arg Pro Asn Ser Lys Ala Val Gly Pro Ser Gly Glu Thr Leu
 210                 215                 220

Thr Ala Ser Glu Ala Phe Lys Leu Ala Gly Val Ser Ser Phe Phe Glu
225                 230                 235                 240

Leu Gln Pro Lys Glu Gly Leu Ala Leu Val Asn Gly Thr Ala Val Gly
                 245                 250                 255

Ser Gly Leu Ala Ser Thr Val Leu Phe Asp Ala Asn Ile Leu Ala Val
                 260                 265                 270

Leu Ser Glu Val Met Ser Ala Met Phe Ala Glu Val Met Gln Gly Lys
                 275                 280                 285

Pro Glu Phe Thr Asp His Leu Thr His Lys Leu Lys His His Pro Gly
                 290                 295                 300

Gln Ile Glu Ala Ala Ala Ile Met Glu His Ile Leu Asp Gly Ser Ser
305                 310                 315                 320

Tyr Val Lys Glu Ala Gln Leu Leu His Glu Met Asp Pro Leu Gln Lys
                 325                 330                 335

Pro Lys Gln Asp Arg Tyr Ala Leu Arg Thr Ser Pro Gln Trp Leu Gly
                 340                 345                 350

Pro Gln Ile Glu Val Ile Arg Ala Ala Thr Lys Met Ile Glu Arg Glu
                 355                 360                 365

Ile Asn Ser Val Asn Asp Asn Pro Leu Ile Asp Val Ser Arg Asn Lys
                 370                 375                 380

Ala Leu His Gly Gly Asn Phe Gln Gly Thr Pro Ile Gly Val Ala Met
385                 390                 395                 400

Asp Asn Ser Arg Leu Ala Ile Ala Ser Ile Gly Lys Leu Met Phe Ala
                 405                 410                 415

Gln Phe Ser Glu Leu Val Asn Asp Phe Tyr Asn Asn Gly Leu Pro Ser
                 420                 425                 430
```

```
Asn Leu Ser Gly Gly Arg Asn Pro Ser Leu Asp Tyr Gly Phe Lys Gly
            435                 440                 445

Ala Glu Ile Ala Met Ala Ser Tyr Cys Ser Glu Leu Gln Phe Leu Ala
        450                 455                 460

Asn Pro Val Thr Asn His Val Gln Ser Ala Glu Gln His Asn Gln Asp
465                 470                 475                 480

Val Asn Ser Leu Gly Leu Ile Ser Ser Arg Lys Thr Ala Glu Ala Val
                485                 490                 495

Asp Ile Leu Lys Leu Met Ser Thr Thr Tyr Leu Val Ala Leu Cys Gln
            500                 505                 510

Ala Val Asp Leu Arg His Leu Glu Glu Asn Leu Lys Lys Ala Val Lys
        515                 520                 525

Ser Ala Val Ser Gln Val Ala Lys Arg Val Leu Thr Val Gly Ala Asn
    530                 535                 540

Gly Glu Leu His Pro Ser Arg Phe Thr Glu Arg Asp Val Leu Gln Val
545                 550                 555                 560

Val Asp Arg Glu Tyr Val Phe Ser Tyr Ala Asp Pro Cys Ser Leu
                565                 570                 575

Thr Tyr Pro Leu Met Gln Lys Leu Arg His Ile Leu Val Asp His Ala
            580                 585                 590

Leu Ala Asp Pro Glu Arg Glu Ala Asn Ser Ala Thr Ser Val Phe His
        595                 600                 605

Lys Ile Gly Ala Phe Glu Ala Glu Leu Lys Leu Leu Pro Lys Glu
610                 615                 620

Val Glu Arg Val Arg Val Glu Tyr Glu Glu Gly Thr Ser Ala Ile Ala
625                 630                 635                 640

Asn Arg Ile Lys Glu Cys Arg Ser Tyr Pro Leu Tyr Arg Phe Val Arg
                645                 650                 655

Asp Glu Leu Asn Thr Glu Leu Leu Thr Gly Glu Asn Val Arg Ser Pro
            660                 665                 670

Gly Glu Glu Phe Asp Lys Val Phe Leu Ala Ile Ser Asp Gly Lys Leu
        675                 680                 685

Ile Asp Pro Leu Leu Glu Cys Leu Lys Glu Trp Asn Gly Ala Pro Val
    690                 695                 700

Ser Ile Cys
705

<210> SEQ ID NO 7
<211> LENGTH: 1512
<212> TYPE: DNA
<213> ORGANISM: Saccharomyces cerevisiae

<400> SEQUENCE: 7
atgaggaagc taaatccagc tttagaattt agagacttta tccaggtctt aaaagatgaa      60
gatgacttaa tcgaaattac cgaagagatt gatccaaatc tcgaagtagg tgcaattatg     120
aggaaggcct atgaatccca cttaccagcc ccgttattta aaaatctcaa aggtgcttcg     180
aaggatcttt tcagcatttt aggttgccca gccggtttga agtaagga gaaaggagat      240 catggtagaa ttgcccatca tctggggctc gacccaaaaa caactatcaa ggaaatcata     300
gattatttgc tggagtgtaa ggagaaggaa cctctccccc caatcactgt tcctgtgtca     360
tctgcacctt gtaaaacaca tatactttct gaagaaaaaa tacatctaca aagcctgcca     420
acaccatatc tacatgtttc agacggtggc aagtacttac aaacgtacgg aatgtggatt     480
```

-continued

```
cttcaaactc cagataaaaa atggactaat tggtcaattg ctagaggtat ggttgtagat      540
gacaagcata tcactggtct ggtaattaaa ccacaacata ttagacaaat tgctgactct      600
tgggcagcaa ttgaaaaagc aaatgaaatt cctttcgcgt tatgttttgg cgttcccca       660 gcagctattt tagttagttc catgccaatt cctgaaggtg tttctgaatc ggattatgtt      720
ggcgcaatct tgggtgagtc ggttccagta gtaaaatgtg agaccaacga tttaatggtt      780
cctgcaacga gtgagatggt atttgagggt actttgtcct aacagatac acatctggaa       840 ggcccatttg gtgagatgca tggatatgtt ttcaaaagcc aaggtcatcc ttgtccattg      900
tacactgtca aggctatgag ttacagagac aatgctattc tacctgtttc gaacccggt      960 ctttgtacgg atgagacaca taccttgatt ggttcactag tggctactga ggccaaggag     1020
ctggctattg aatctggctt gccaattctg gatgccttta tgccttatga ggctcaggct     1080
ctttggctta tcttaaaggt ggatttgaaa gggctgcaag cattgaagac aacgcctgaa     1140
gaattttgta agaaggtagg tgatatttac tttaggacaa aagttggttt tatagtccat     1200
gaaataattt tggtggcaga tgatatcgac atatttaact tcaaagaagt catctgggcc     1260
tacgttacaa gacatacacc tgttgcagat cagatggctt tgatgatgt cacttcttt       1320 cctttggctc cctttgtttc gcagtcatcc agaagtaaga ctatgaaagg tggaaagtgc     1380
gttactaatt gcatatttag acagcaatat gagcgcagtt ttgactacat aacttgtaat     1440
tttgaaaagg gatatccaaa aggattagtt gacaaagtaa atgaaaattg gaaaaggtac     1500
ggatataaat aa                                                         1512
```

<210> SEQ ID NO 8
<211> LENGTH: 503
<212> TYPE: PRT
<213> ORGANISM: Saccharomyces cerevisiae

<400> SEQUENCE: 8

```
Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
        115                 120                 125

Leu Ser Glu Glu Lys Ile His Leu Gln Ser Leu Pro Thr Pro Tyr Leu
    130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Lys Pro Gln
            180                 185                 190
```

His Ile Arg Gln Ile Ala Asp Ser Trp Ala Ala Ile Gly Lys Ala Asn
            195                 200                 205

Glu Ile Pro Phe Ala Leu Cys Phe Gly Val Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Lys Cys Glu Thr Asn
                245                 250                 255

Asp Leu Met Val Pro Ala Thr Ser Glu Met Val Phe Glu Gly Thr Leu
                260                 265                 270

Ser Leu Thr Asp Thr His Leu Glu Gly Pro Phe Gly Met His Gly
            275                 280                 285

Tyr Val Phe Lys Ser Gln Gly His Pro Cys Pro Leu Tyr Thr Val Lys
        290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
        355                 360                 365

Leu Lys Gly Leu Gln Ala Leu Lys Thr Thr Pro Glu Glu Phe Cys Lys
    370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
        435                 440                 445

Ser Ser Arg Ser Lys Thr Met Lys Gly Gly Lys Cys Val Thr Asn Cys
    450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500

<210> SEQ ID NO 9
<211> LENGTH: 1503
<212> TYPE: DNA
<213> ORGANISM: Aspergillus niger

<400> SEQUENCE: 9
atgtctgcgc aacctgctca cctgtgtttc cgctccttcg tcgaagccct caaggtcgac        60
aacgaccttg ttgaaatcaa taccccaatt gaccccaatc tcgaagctgc tgctattacc       120
cgccgagtat gtgagaccaa cgacaaggct cctttattca caacctcat cggcatgaaa        180 aatggcctct tccgtatact ggggctcct ggctctctca ggaagtcgtc tgctgatcgc        240
tacggccgcc ttgctcgtca cctagccctc ccacctacgg cctcaatgcg tgagattctc       300

```
gataagatgc tctccgccag cgatatgcct cccatccctc cgaccattgt tcccaccggg    360
ccatgcaagg agaacagctt agatgactct gaattcgacc ttaccgaact ccccgttcct    420
cttattcaca aatcggatgg tggtaaatac atccaaacct atggcatgca cattgtgcag    480
tctccggatg gaacctggac caactggtct attgcccgtg cgatggtcca tgacaagaac    540
catctgaccg gcctggttat tccccctcag cacatctggc agattcacca gatgtggaag    600
aaggaaggcc gcagtgacgt tccctgggct ttggcctttg tgtcccacc cgctgccatt     660 atggcctcta gcatgcctat tcccgatggt gtcaccgaag ctgggtacgt gggagctatg    720
acgggatcct ccctggagct tgttaaatgt gatacgaacg atctatatgt ccccgctacc    780
tcagaaatcg ttctcgaggg cacactctct atcagcgaga caggcccaga gggaccttc     840 ggtgagatgc atggttacat cttccccggg gatactcacc tcggcgccaa atacaaggtt    900
aaccggatca cctaccgcaa caacgccatc atgcccatgt cttcttgtgg ccgcttgacg    960
gatgaaacgc acaccatgat cggctctctg gctgcggcgg agatccgtaa gctctgccag   1020
cagaatgacc tccctatcac tgatgccttc gctcctttcg agtctcaagt tacctgggtt   1080
gctctgcggg tcgatactga gaagctacgt gccatgaaga caacgtctga gggattccgc   1140
aagagagtgg gagacgtcgt cttcaaccac aaggccggat acaccattca tcgtctggtg   1200
ttggtcggtg acgacattga tgtctatgaa ggaaaggatg tgctctgggc gttctccacc   1260
cgttgccgtc ctggtatgga cgagactttg tttgaggatg ttcgtggtt ccccttgatt    1320 ccgtatatgg gacacgggaa tgggcccgcc caccgcggcg gaaaggttgt gtccgacgct   1380
cttatgccga ctgagtacac cactggtcgc aactgggagg ctgctgactt caaccaatct   1440
tatcccgagg atctgaagca gaaggtgttg gacaactgga cgaagatggg tttcagcaac   1500
taa                                                                 1503
```

<210> SEQ ID NO 10
<211> LENGTH: 500
<212> TYPE: PRT
<213> ORGANISM: Aspergillus niger

<400> SEQUENCE: 10

Met Ser Ala Gln Pro Ala His Leu Cys Phe Arg Ser Phe Val Glu Ala
1               5                   10                  15

Leu Lys Val Asp Asn Asp Leu Val Glu Ile Asn Thr Pro Ile Asp Pro
            20                  25                  30

Asn Leu Glu Ala Ala Ala Ile Thr Arg Arg Val Cys Glu Thr Asn Asp
        35                  40                  45

Lys Ala Pro Leu Phe Asn Asn Leu Ile Gly Met Lys Asn Gly Leu Phe
    50                  55                  60

Arg Ile Leu Gly Ala Pro Gly Ser Leu Arg Lys Ser Ala Asp Arg
65                  70                  75                  80

Tyr Gly Arg Leu Ala Arg His Leu Ala Leu Pro Pro Thr Ala Ser Met
                85                  90                  95

Arg Glu Ile Leu Asp Lys Met Leu Ser Ala Ser Asp Met Pro Pro Ile
            100                 105                 110

Pro Pro Thr Ile Val Pro Thr Gly Pro Cys Lys Glu Asn Ser Leu Asp
        115                 120                 125

Asp Ser Glu Phe Asp Leu Thr Glu Leu Pro Val Pro Leu Ile His Lys
    130                 135                 140

Ser Asp Gly Gly Lys Tyr Ile Gln Thr Tyr Gly Met His Ile Val Gln
145                 150                 155                 160

Ser Pro Asp Gly Thr Trp Thr Asn Trp Ser Ile Ala Arg Ala Met Val
            165                 170                 175

His Asp Lys Asn His Leu Thr Gly Leu Val Ile Pro Pro Gln His Ile
        180                 185                 190

Trp Gln Ile His Gln Met Trp Lys Lys Glu Gly Arg Ser Asp Val Pro
    195                 200                 205

Trp Ala Leu Ala Phe Gly Val Pro Ala Ala Ile Met Ala Ser Ser
210                 215                 220

Met Pro Ile Pro Asp Gly Val Thr Glu Ala Gly Tyr Val Gly Ala Met
225                 230                 235                 240

Thr Gly Ser Ser Leu Glu Leu Val Lys Cys Asp Thr Asn Asp Leu Tyr
                245                 250                 255

Val Pro Ala Thr Ser Glu Ile Val Leu Glu Gly Thr Leu Ser Ile Ser
            260                 265                 270

Glu Thr Gly Pro Glu Gly Pro Phe Gly Glu Met His Gly Tyr Ile Phe
        275                 280                 285

Pro Gly Asp Thr His Leu Gly Ala Lys Tyr Lys Val Asn Arg Ile Thr
    290                 295                 300

Tyr Arg Asn Asn Ala Ile Met Pro Met Ser Ser Cys Gly Arg Leu Thr
305                 310                 315                 320

Asp Glu Thr His Thr Met Ile Gly Ser Leu Ala Ala Ala Glu Ile Arg
                325                 330                 335

Lys Leu Cys Gln Gln Asn Asp Leu Pro Ile Thr Asp Ala Phe Ala Pro
            340                 345                 350

Phe Glu Ser Gln Val Thr Trp Val Ala Leu Arg Val Asp Thr Glu Lys
        355                 360                 365

Leu Arg Ala Met Lys Thr Thr Ser Glu Gly Phe Arg Lys Arg Val Gly
    370                 375                 380

Asp Val Val Phe Asn His Lys Ala Gly Tyr Thr Ile His Arg Leu Val
385                 390                 395                 400

Leu Val Gly Asp Asp Ile Asp Val Tyr Glu Gly Lys Asp Val Leu Trp
                405                 410                 415

Ala Phe Ser Thr Arg Cys Arg Pro Gly Met Asp Glu Thr Leu Phe Glu
            420                 425                 430

Asp Val Arg Gly Phe Pro Leu Ile Pro Tyr Met Gly His Gly Asn Gly
        435                 440                 445

Pro Ala His Arg Gly Gly Lys Val Ser Asp Ala Leu Met Pro Thr
    450                 455                 460

Glu Tyr Thr Thr Gly Arg Asn Trp Glu Ala Ala Asp Phe Asn Gln Ser
465                 470                 475                 480

Tyr Pro Glu Asp Leu Lys Gln Lys Val Leu Asp Asn Trp Thr Lys Met
                485                 490                 495

Gly Phe Ser Asn
            500

<210> SEQ ID NO 11
<211> LENGTH: 3774
<212> TYPE: DNA
<213> ORGANISM: Artificial Sequence
<220> FEATURE:
<223> OTHER INFORMATION: Synthetic

<400> SEQUENCE: 11
atgtcgtact accatcacca tcaccatcac ctcgaatcaa caagtttgta caaaaaagca      60

```
ggctccgcgg ccgccccctt caccatgagg aagctaaatc cagctttaga atttagagac    120
tttatccagg tcttaaaaga tgaagatgac ttaatcgaaa ttaccgaaga gattgatcca    180
aatctcgaag taggtgcaat tatgaggaag gcctatgaat cccacttacc agccccgtta    240
tttaaaaatc tcaaaggtgc ttcgaaggat cttttcagca ttttaggttg cccagccggt    300
ttgagaagta aggagaaagg agatcatggt agaattgccc atcatctggg gctcgaccca    360
aaaacaacta tcaaggaaat catagattat tgctggagt gtaaggagaa ggaacctctc     420
cccccaatca ctgttcctgt gtcatctgca ccttgtaaaa cacatatact ttctgaagaa    480
aaaatacatc tacaaagcct gccaacacca tatctacatg tttcagacgg tggcaagtac    540
ttacaaacgt acggaatgtg gattcttcaa actccagata aaaaatggac taattggtca    600
attgctagag gtatggttgt agatgacaag catatcactg gtctggtaat taaaccacaa    660
catattagac aaattgctga ctcttgggca gcaattggaa aagcaaatga aattcctttc    720
gcgttatgtt ttggcgttcc cccagcagct attttagtta gttccatgcc aattcctgaa    780
ggtgtttctg aatcggatta tgttggcgca atccttgggtg agtcggttcc agtagtaaaa    840
tgtgagacca acgatttaat ggttcctgca acgagtgaga tggtatttga gggtactttg    900
tccttaacag atacacatct ggaaggccca tttggtgaga tgcatggata tgttttcaaa    960
agccaaggtc atccttgtcc attgtacact gtcaaggcta tgagttacag agacaatgct   1020
attctacctg tttcgaaccc cggtctttgt acggatgaga cacataccct gattggttca   1080
ctagtggcta ctgaggccaa ggagctggct attgaatctg cttgccaat tctggatgcc    1140 tttatgcctt atgaggctca ggctctttgg cttatcttaa aggtggattt gaaagggctg   1200
caagcattga agacaacgcc tgaagaattt tgtaagaagg taggtgatat ttactttagg   1260
acaaaagttg gttttatagt ccatgaaata attttggtgg cagatgatat cgacatattt   1320
aacttcaaag aagtcatctg gcctacgtt acaagacata cacctgttgc agatcagatg    1380
gcttttgatg atgtcacttc ttttccttttg gctccctttg tttcgcagtc atccagaagt   1440
aagactatga aggtggaaa gtgcgttact aattgcatat ttagacagca atatgagcgc    1500
agttttgact acataacttg taattttgaa aagggatatc caaaaggatt agttgacaaa   1560
gtaaatgaaa attggaaaag gtacggatat aaatctggtg gctcaggagg ctctggagcc   1620
atggatcaaa tcgaagcaat gttgtgcggc ggaggagaga agacaaaagt ggcggttact   1680
acgaagactt tggcagatcc attgaattgg ggtttagcag cggatcaaat gaaaggaagt   1740
catttagatg aagtgaagaa gatggtcgaa gagtatcgta gaccagtcgt gaatcttggc   1800
ggagaaacac tgacgatcgg acaagttgct gccatctcca ccgtaggagg cagcgttaag   1860
gttgagttag cggagacttc aagagccggt gtgaaagcta gcagtgattg ggttatggag   1920
agcatgaaca aggtactgaa cagttacgga gtcaccaccg gctttggtgc tacttctcac   1980
cggagaacca aaaacggcac cgcattacaa acagaactca ttagattttt gaacgccgga   2040
atattcggaa acacgaagga gacatgtcac acactgccgc aatccgccac aagagccgcc   2100
atgctcgtca gagtcaacac tcttctccaa ggatactccg ggatccgatt cgagatcctc   2160
gaagcgatta caagtctcct caaccacaac atctctccgt cactacctct ccgtggaacc   2220
attaccgcct ccggcgatct cgttcctctc tcttacatcg ccggacttct caccggccgt   2280
cctaattcca aagccaccgg tcccgacggt gaatcgctaa ccgcgaaaga agcttttgag   2340
aaagccggaa tcagtactgg attcttcgat ttacaaccta aggaaggttt agctctcgtt   2400
aatggcacgg cggttggatc tggaatggcg tcgatggttc tattcgaagc gaatgtccaa   2460
```

```
gcggtgttag cggaggtttt atcagcgatc ttcgcggagg ttatgagcgg gaaacctgag    2520
tttaccgatc atctgactca tcgtttaaaa catcatcccg gacaaatcga agcggcggcg    2580
ataatggagc acatactcga cggaagctca tacatgaaat tagctcaaaa ggttcacgag    2640
atggatccat tgcagaaacc aaaacaagat cgttacgctc ttcgtacatc tcctcaatgg    2700
ctaggtcctc aaattgaagt aatccgtcaa gctacgaaat cgatagagcg tgaaatcaac    2760
tccgttaacg ataatccgtt gatcgatgtt tcgaggaaca aggcgattca cggtggtaac    2820
ttccaaggaa caccaatcgg agtttctatg gataacacga gattggcgat gctgcgatt     2880 gggaagctaa tgtttgctca attctctgag cttgttaatg atttctacaa caatggactt    2940
ccttcgaatc taactgcttc gagtaatcca agtttggatt atggattcaa aggagcagag    3000
attgctatgg cttcttattg ttctgagctt caatacttgg ctaatccagt cacaagccat    3060
gttcaatcag ctgagcaaca taatcaagat gtgaactctc ttggtttgat ctcgtctcgt    3120
aaaacatctg aagctgtgga tattcttaag ctaatgtcaa caacgttcct tgtggggata    3180
tgtcaagctg ttgatttgag acatttggag gagaatctga caaactgt gaagaacaca     3240 gtttctcaag ttgctaagaa agtgttaacc actggaatca acggtgagtt acatccgtca    3300
aggttttgcg agaaggactt gcttaaggtt gttgatcgtg agcaagtgtt cacgtatgtg    3360
gatgatcctt gtagcgctac gtacccgttg atgcagagac taagacaagt tattgttgat    3420
cacgctttgt ccaacggtga gactgagaag aatgcagtga cttcgatctt tcaaaagatt    3480
ggagcttttg aagaggagct taaggctgtg cttccaaagg aagttgaagc ggctagagcg    3540
gcttatggga atggaactgc gccgattcct aaccggatta aggaatgtag gtcgtatccg    3600
ttgtataggt tcgtgaggga agagcttgga acgaagttgt tgactggaga aaaggttgtg    3660
tctccgggag aggagtttga taaggtcttc actgctatgt gtgaaggtaa acttattgat    3720
ccgttgatgg attgtctcaa ggaatggaac ggagctccga ttccgatttg ctaa          3774
```

<210> SEQ ID NO 12
<211> LENGTH: 1257
<212> TYPE: PRT
<213> ORGANISM: Artificial Sequence
<220> FEATURE:
<223> OTHER INFORMATION: Synthetic

<400> SEQUENCE: 12

```
Met Ser Tyr Tyr His His His His His His Leu Glu Ser Thr Ser Leu
1               5                   10                  15

Tyr Lys Lys Ala Gly Ser Ala Ala Ala Pro Phe Thr Met Arg Lys Leu
            20                  25                  30

Asn Pro Ala Leu Glu Phe Arg Asp Phe Ile Gln Val Leu Lys Asp Glu
        35                  40                  45

Asp Asp Leu Ile Glu Ile Thr Glu Glu Ile Asp Pro Asn Leu Glu Val
    50                  55                  60

Gly Ala Ile Met Arg Lys Ala Tyr Glu Ser His Leu Pro Ala Pro Leu
65                  70                  75                  80

Phe Lys Asn Leu Lys Gly Ala Ser Lys Asp Leu Phe Ser Ile Leu Gly
                85                  90                  95

Cys Pro Ala Gly Leu Arg Ser Lys Glu Lys Gly Asp His Gly Arg Ile
            100                 105                 110

Ala His His Leu Gly Leu Asp Pro Lys Thr Thr Ile Lys Glu Ile Ile
        115                 120                 125
```

-continued

```
Asp Tyr Leu Leu Glu Cys Lys Glu Lys Glu Pro Leu Pro Pro Ile Thr
130                 135                 140

Val Pro Val Ser Ser Ala Pro Cys Lys Thr His Ile Leu Ser Glu Glu
145                 150                 155                 160

Lys Ile His Leu Gln Ser Leu Pro Thr Pro Tyr Leu His Val Ser Asp
            165                 170                 175

Gly Gly Lys Tyr Leu Gln Thr Tyr Gly Met Trp Ile Leu Gln Thr Pro
        180                 185                 190

Asp Lys Lys Trp Thr Asn Trp Ser Ile Ala Arg Gly Met Val Val Asp
    195                 200                 205

Asp Lys His Ile Thr Gly Leu Val Ile Lys Pro Gln His Ile Arg Gln
210                 215                 220

Ile Ala Asp Ser Trp Ala Ala Ile Gly Lys Ala Asn Glu Ile Pro Phe
225                 230                 235                 240

Ala Leu Cys Phe Gly Val Pro Pro Ala Ala Ile Leu Val Ser Ser Met
                245                 250                 255

Pro Ile Pro Glu Gly Val Ser Glu Ser Asp Tyr Val Gly Ala Ile Leu
            260                 265                 270

Gly Glu Ser Val Pro Val Lys Cys Glu Thr Asn Asp Leu Met Val
        275                 280                 285

Pro Ala Thr Ser Glu Met Val Phe Glu Gly Thr Leu Ser Leu Thr Asp
290                 295                 300

Thr His Leu Glu Gly Pro Phe Gly Glu Met His Gly Tyr Val Phe Lys
305                 310                 315                 320

Ser Gln Gly His Pro Cys Pro Leu Tyr Thr Val Lys Ala Met Ser Tyr
                325                 330                 335

Arg Asp Asn Ala Ile Leu Pro Val Ser Asn Pro Gly Leu Cys Thr Asp
            340                 345                 350

Glu Thr His Thr Leu Ile Gly Ser Leu Val Ala Thr Glu Ala Lys Glu
        355                 360                 365

Leu Ala Ile Glu Ser Gly Leu Pro Ile Leu Asp Ala Phe Met Pro Tyr
370                 375                 380

Glu Ala Gln Ala Leu Trp Leu Ile Leu Lys Val Asp Leu Lys Gly Leu
385                 390                 395                 400

Gln Ala Leu Lys Thr Thr Pro Glu Glu Phe Cys Lys Lys Val Gly Asp
                405                 410                 415

Ile Tyr Phe Arg Thr Lys Val Gly Phe Ile Val His Glu Ile Ile Leu
            420                 425                 430

Val Ala Asp Asp Ile Asp Ile Phe Asn Phe Lys Glu Val Ile Trp Ala
        435                 440                 445

Tyr Val Thr Arg His Thr Pro Val Ala Asp Gln Met Ala Phe Asp Asp
450                 455                 460

Val Thr Ser Phe Pro Leu Ala Pro Phe Val Ser Gln Ser Ser Arg Ser
465                 470                 475                 480

Lys Thr Met Lys Gly Gly Lys Cys Val Thr Asn Cys Ile Phe Arg Gln
                485                 490                 495

Gln Tyr Glu Arg Ser Phe Asp Tyr Ile Thr Cys Asn Phe Glu Lys Gly
            500                 505                 510

Tyr Pro Lys Gly Leu Val Asp Lys Val Asn Glu Asn Trp Lys Arg Tyr
        515                 520                 525

Gly Tyr Lys Ser Gly Gly Ser Gly Ser Ala Met Asp Gln Ile
    530                 535                 540

Glu Ala Met Leu Cys Gly Gly Gly Glu Lys Thr Lys Val Ala Val Thr
```

```
               545                 550                 555                 560
        Thr Lys Thr Leu Ala Asp Pro Leu Asn Trp Gly Leu Ala Ala Asp Gln
                        565                 570                 575
        Met Lys Gly Ser His Leu Asp Glu Val Lys Lys Met Val Glu Glu Tyr
                        580                 585                 590
        Arg Arg Pro Val Val Asn Leu Gly Glu Thr Leu Thr Ile Gly Gln
                    595                 600                 605
        Val Ala Ala Ile Ser Thr Val Gly Gly Ser Val Lys Val Glu Leu Ala
                    610                 615                 620
        Glu Thr Ser Arg Ala Gly Val Lys Ala Ser Ser Asp Trp Val Met Glu
        625                 630                 635                 640
        Ser Met Asn Lys Gly Thr Asp Ser Tyr Gly Val Thr Thr Gly Phe Gly
                        645                 650                 655
        Ala Thr Ser His Arg Arg Thr Lys Asn Gly Thr Ala Leu Gln Thr Glu
                        660                 665                 670
        Leu Ile Arg Phe Leu Asn Ala Gly Ile Phe Gly Asn Thr Lys Glu Thr
                        675                 680                 685
        Cys His Thr Leu Pro Gln Ser Ala Thr Arg Ala Ala Met Leu Val Arg
                        690                 695                 700
        Val Asn Thr Leu Leu Gln Gly Tyr Ser Gly Ile Arg Phe Glu Ile Leu
        705                 710                 715                 720
        Glu Ala Ile Thr Ser Leu Leu Asn His Asn Ile Ser Pro Ser Leu Pro
                        725                 730                 735
        Leu Arg Gly Thr Ile Thr Ala Ser Gly Asp Leu Val Pro Leu Ser Tyr
                        740                 745                 750
        Ile Ala Gly Leu Leu Thr Gly Arg Pro Asn Ser Lys Ala Thr Gly Pro
                    755                 760                 765
        Asp Gly Glu Ser Leu Thr Ala Lys Glu Ala Phe Glu Lys Ala Gly Ile
                770                 775                 780
        Ser Thr Gly Phe Phe Asp Leu Gln Pro Lys Glu Gly Leu Ala Leu Val
        785                 790                 795                 800
        Asn Gly Thr Ala Val Gly Ser Gly Met Ala Ser Met Val Leu Phe Glu
                        805                 810                 815
        Ala Asn Val Gln Ala Val Leu Ala Glu Val Leu Ser Ala Ile Phe Ala
                        820                 825                 830
        Glu Val Met Ser Gly Lys Pro Glu Phe Thr Asp His Leu Thr His Arg
                    835                 840                 845
        Leu Lys His His Pro Gly Gln Ile Glu Ala Ala Ile Met Glu His
                    850                 855                 860
        Ile Leu Asp Gly Ser Ser Tyr Met Lys Leu Ala Gln Lys Val His Glu
        865                 870                 875                 880
        Met Asp Pro Leu Gln Lys Pro Lys Gln Asp Arg Tyr Ala Leu Arg Thr
                        885                 890                 895
        Ser Pro Gln Trp Leu Gly Pro Gln Ile Glu Val Ile Arg Gln Ala Thr
                    900                 905                 910
        Lys Ser Ile Glu Arg Glu Ile Asn Ser Val Asn Asp Asn Pro Leu Ile
                    915                 920                 925
        Asp Val Ser Arg Asn Lys Ala Ile His Gly Gly Asn Phe Gln Gly Thr
                    930                 935                 940
        Pro Ile Gly Val Ser Met Asp Asn Thr Arg Leu Ala Ile Ala Ala Ile
        945                 950                 955                 960
        Gly Lys Leu Met Phe Ala Gln Phe Ser Glu Leu Val Asn Asp Phe Tyr
                        965                 970                 975
```

Asn Asn Gly Leu Pro Ser Asn Leu Thr Ala Ser Ser Asn Pro Ser Leu
            980                 985                 990

Asp Tyr Gly Phe Lys Gly Ala Glu Ile Ala Met Ala Ser Tyr Cys Ser
            995                1000                1005

Glu Leu Gln Tyr Leu Ala Asn Pro Val Thr Ser His Val Gln Ser
       1010                1015                1020

Ala Glu Gln His Asn Gln Asp Val Asn Ser Leu Gly Leu Ile Ser
       1025                1030                1035

Ser Arg Lys Thr Ser Glu Ala Val Asp Ile Leu Lys Leu Met Ser
       1040                1045                1050

Thr Thr Phe Leu Val Gly Ile Cys Gln Ala Val Asp Leu Arg His
       1055                1060                1065

Leu Glu Glu Asn Leu Arg Gln Thr Val Lys Asn Thr Val Ser Gln
       1070                1075                1080

Val Ala Lys Lys Val Leu Thr Thr Gly Ile Asn Gly Glu Leu His
       1085                1090                1095

Pro Ser Arg Phe Cys Glu Lys Asp Leu Leu Lys Val Val Asp Arg
       1100                1105                1110

Glu Gln Val Phe Thr Tyr Val Asp Asp Pro Cys Ser Ala Thr Tyr
       1115                1120                1125

Pro Leu Met Gln Arg Leu Arg Gln Val Ile Val Asp His Ala Leu
       1130                1135                1140

Ser Asn Gly Glu Thr Glu Lys Asn Ala Val Thr Ser Ile Phe Gln
       1145                1150                1155

Lys Ile Gly Ala Phe Glu Glu Glu Leu Lys Ala Val Leu Pro Lys
       1160                1165                1170

Glu Val Glu Ala Ala Arg Ala Ala Tyr Gly Asn Gly Thr Ala Pro
       1175                1180                1185

Ile Pro Asn Arg Ile Lys Glu Cys Arg Ser Tyr Pro Leu Tyr Arg
       1190                1195                1200

Phe Val Arg Glu Glu Leu Gly Thr Lys Leu Leu Thr Gly Glu Lys
       1205                1210                1215

Val Val Ser Pro Gly Glu Glu Phe Asp Lys Val Phe Thr Ala Met
       1220                1225                1230

Cys Glu Gly Lys Leu Ile Asp Pro Leu Met Asp Cys Leu Lys Glu
       1235                1240                1245

Trp Asn Gly Ala Pro Ile Pro Ile Cys
       1250                1255

<210> SEQ ID NO 13
<211> LENGTH: 3774
<212> TYPE: DNA
<213> ORGANISM: Artificial Sequence
<220> FEATURE:
<223> OTHER INFORMATION: Synthetic

<400> SEQUENCE: 13
atgtcgtact accatcacca tcaccatcac ctcgaatcaa caagtttgta caaaaaagca      60
ggctccgcgg ccgccccctt caccatgagg aagctaaatc cagctttaga atttagagac     120
tttatccagg tcttaaaaga tgaagatgac ttaatcgaaa ttaccgaaga gattgatcca     180
aatctcgaag taggtgcaat tatgaggaag cctatgaat cccacttacc agccccgtta     240
tttaaaaatc tcaaaggtgc ttcgaaggat ctttttcagca tttttaggttg cccagccggt     300 ttgagaagta aggagaaagg agatcatggt agaattgccc atcatctggg gctcgaccca     360

```
aaaacaacta tcaaggaaat catagattat ttgctggagt gtaaggagaa ggaacctctc    420 ccccccaatca ctgttcctgt gtcatctgca ccttgtaaaa cacatatact ttctgaagaa    480
aaaatacatc tacaaagcct gccaacacca tatctacatg tttcagacgg tggcaagtac    540
ttacaaacgt acggaatgtg gattcttcaa actccagata aaaaatggac taattggtca    600
attgctagag gtatggttgt agatgacaag catatcactg gtctggtaat tgagccacaa    660
catattagac aaaattgctga ctcttgggca gcaattggaa aagcaaatga aattcctttc    720
gcgttatgtt ttggcgttcc cccagcagct atttagtta gttccatgcc aattcctgaa    780
ggtgtttctg aatcggatta tgttggcgca atcttgggtg agtcggttcc agtagtaaaa    840
tgtgagacca acgatttaat ggttcctgca acgagtgaga tggtatttga gggtactttg    900
tccttaacag atacacatct ggaaggccca tttggtgaga tgcatggata tgttttcaaa    960
agccaaggtc atccttgtcc attgtacact gtcaaggcta tgagttacag agacaatgct    1020
attctacctg tttcgaaccc cggtctttgt acggatgaga cacataccct gattggttca    1080
ctagtggcta ctgaggccaa ggagctggct attgaatctg gcttgccaat tctggatgcc    1140
tttatgcctt atgaggctca ggctctttgg cttatcttaa aggtggattt gaaagggctg    1200
caagcattga agacaacgcc tgaagaattt tgtaagaagg taggtgatat ttactttagg    1260
acaaaagttg gttttatagt ccatgaaata attttggtgg cagatgatat cgacatattt    1320
aacttcaaag aagtcatctg ggcctacgtt acaagacata cacctgttgc agatcagatg    1380
gcttttgatg atgtcacttc ttttccttg gctccctttg tttcgcagtc atccagaagt    1440
aagactatga aggtggaaa gtgcgttact aattgcatat ttagacagca atatgagcgc    1500
agttttgact acataacttg taattttgaa aagggatatc caaaaggatt agttgacaaa    1560
gtaaatgaaa attggaaaag gtacggatat aaatctggtg gctcaggagg ctctggagcc    1620
atggatcaaa tcgaagcaat gttgtgcggc ggaggagaga agacaaaagt ggcggttact    1680
acgaagactt tggcagatcc attgaattgg ggtttagcag cggatcaaat gaaaggaagt    1740
catttagatg aagtgaagaa gatggtcgaa gagtatcgta gaccagtcgt gaatcttggc    1800
ggagaaacac tgacgatcgg acaagttgct gccatctcca ccgtaggagg cagcgttaag    1860
gttgagttag cggagacttc aagagccggt gtgaaagcta gcagtgattg ggttatggag    1920
agcatgaaca aggtactga cagttacgga gtcaccaccg gctttggtgc tacttctcac    1980
cggagaacca aaaacggcac cgcattacaa acagaactca ttagattttt gaacgccgga    2040
atattcggaa acacgaagga gacatgtcac acactgccgc aatccgccac aagagccgcc    2100
atgctcgtca gagtcaacac tcttctccaa ggatactccg ggatccgatt cgagatcctc    2160
gaagcgatta caagtctcct caaccacaac atctctccgt cactacctct ccgtggaacc    2220
attaccgcct ccggcgatct cgttcctctc tcttacatcg ccggacttct caccggccgt    2280
cctaattcca aagccaccgg tcccgacggt gaatcgctaa ccgcgaaaga agcttttgag    2340
aaagccggaa tcagtactgg attcttcgat ttacaaccta aggaaggttt agctctcgtt    2400
aatggcacgg cggttggatc tggaatggcg tcgatggttc tattcgaagc gaatgtccaa    2460
gcggtgttag cggaggtttt atcagcgatc ttcgcgagg ttatgagcgg gaaacctgag    2520
tttaccgatc atctgactca tcgttaaaaa catcatcccg gacaaatcga agcggcggcg    2580
ataatggagc acatactcga cggaagctca tacatgaaat tagctcaaaa ggttcacgag    2640
atggatccat tgcagaaacc aaaacaagat cgttacgctc ttcgtacatc tcctcaatgg    2700
```

-continued

```
ctaggtcctc aaattgaagt aatccgtcaa gctacgaaat cgatagagcg tgaaatcaac    2760
tccgttaacg ataatccgtt gatcgatgtt tcgaggaaca aggcgattca cggtggtaac    2820
ttccaaggaa caccaatcgg agtttctatg gataacacga gattggcgat tgctgcgatt    2880
gggaagctaa tgtttgctca attctctgag cttgttaatg atttctacaa caatggactt    2940
ccttcgaatc taactgcttc gagtaatcca agtttggatt atggattcaa aggagcagag    3000
attgctatgg cttcttattg ttctgagctt caatacttgg ctaatccagt cacaagccat    3060
gttcaatcag ctgagcaaca taatcaagat gtgaactctc ttggtttgat ctcgtctcgt    3120
aaaacatctg aagctgtgga tattcttaag ctaatgtcaa caacgttcct tgtggggata    3180
tgtcaagctg ttgatttgag acatttggag gagaatctga caaaactgt gaagaacaca    3240 gtttctcaag ttgctaagaa agtgttaacc actggaatca acggtgagtt acatccgtca    3300
aggttttgcg agaaggactt gcttaaggtt gttgatcgtg agcaagtgtt cacgtatgtg    3360
gatgatcctt gtagcgctac gtaccccgttg atgcagagac taagacaagt tattgttgat    3420
cacgctttgt ccaacggtga gactgagaag aatgcagtga cttcgatctt tcaaaagatt    3480
ggagcttttg aagaggagct taaggctgtg cttccaaagg aagttgaagc ggctagagcg    3540
gcttatggga atgaactgc gccgattcct aaccggatta aggaatgtag gtcgtatccg    3600
ttgtataggt tcgtgaggga agagcttgga acgaagttgt tgactggaga aaaggttgtg    3660
tctccgggag aggagtttga taaggtcttc actgctatgt gtgaaggtaa acttattgat    3720
ccgttgatgg attgtctcaa ggaatggaac ggagctccga ttccgatttg ctaa          3774
```

```
<210> SEQ ID NO 14
<211> LENGTH: 1257
<212> TYPE: PRT
<213> ORGANISM: Artificial Sequence
<220> FEATURE:
<223> OTHER INFORMATION: Synthetic

<400> SEQUENCE: 14
```

```
Met Ser Tyr Tyr His His His His His His Leu Glu Ser Thr Ser Leu
1               5                   10                  15

Tyr Lys Lys Ala Gly Ser Ala Ala Ala Pro Phe Thr Met Arg Lys Leu
            20                  25                  30

Asn Pro Ala Leu Glu Phe Arg Asp Phe Ile Gln Val Leu Lys Asp Glu
        35                  40                  45

Asp Asp Leu Ile Glu Ile Thr Glu Glu Ile Asp Pro Asn Leu Glu Val
    50                  55                  60

Gly Ala Ile Met Arg Lys Ala Tyr Glu Ser His Leu Pro Ala Pro Leu
65                  70                  75                  80

Phe Lys Asn Leu Lys Gly Ala Ser Lys Asp Leu Phe Ser Ile Leu Gly
                85                  90                  95

Cys Pro Ala Gly Leu Arg Ser Lys Glu Lys Gly Asp His Gly Arg Ile
            100                 105                 110

Ala His His Leu Gly Leu Asp Pro Lys Thr Thr Ile Lys Glu Ile Ile
        115                 120                 125

Asp Tyr Leu Leu Glu Cys Lys Glu Lys Pro Leu Pro Pro Ile Thr
    130                 135                 140

Val Pro Val Ser Ser Ala Pro Cys Lys Thr His Ile Leu Ser Glu Glu
145                 150                 155                 160

Lys Ile His Leu Gln Ser Leu Pro Thr Pro Tyr Leu His Val Ser Asp
                165                 170                 175
```

```
Gly Gly Lys Tyr Leu Gln Thr Tyr Gly Met Trp Ile Leu Gln Thr Pro
            180                 185                 190

Asp Lys Lys Trp Thr Asn Trp Ser Ile Ala Arg Gly Met Val Val Asp
            195                 200                 205

Asp Lys His Ile Thr Gly Leu Val Ile Glu Pro Gln His Ile Arg Gln
            210                 215                 220

Ile Ala Asp Ser Trp Ala Ile Gly Lys Ala Asn Glu Ile Pro Phe
225                 230                 235                 240

Ala Leu Cys Phe Gly Val Pro Ala Ala Ile Leu Val Ser Ser Met
            245                 250                 255

Pro Ile Pro Glu Gly Val Ser Glu Ser Asp Tyr Val Gly Ala Ile Leu
            260                 265                 270

Gly Glu Ser Val Pro Val Val Lys Cys Glu Thr Asn Asp Leu Met Val
            275                 280                 285

Pro Ala Thr Ser Glu Met Val Phe Glu Gly Thr Leu Ser Leu Thr Asp
            290                 295                 300

Thr His Leu Glu Gly Pro Phe Gly Glu Met His Gly Tyr Val Phe Lys
305                 310                 315                 320

Ser Gln Gly His Pro Cys Pro Leu Tyr Thr Val Lys Ala Met Ser Tyr
            325                 330                 335

Arg Asp Asn Ala Ile Leu Pro Val Ser Asn Pro Gly Leu Cys Thr Asp
            340                 345                 350

Glu Thr His Thr Leu Ile Gly Ser Leu Val Ala Thr Glu Ala Lys Glu
            355                 360                 365

Leu Ala Ile Glu Ser Gly Leu Pro Ile Leu Asp Ala Phe Met Pro Tyr
            370                 375                 380

Glu Ala Gln Ala Leu Trp Leu Ile Leu Lys Val Asp Leu Lys Gly Leu
385                 390                 395                 400

Gln Ala Leu Lys Thr Thr Pro Glu Glu Phe Cys Lys Lys Val Gly Asp
            405                 410                 415

Ile Tyr Phe Arg Thr Lys Val Gly Phe Ile Val His Glu Ile Ile Leu
            420                 425                 430

Val Ala Asp Asp Ile Asp Ile Phe Asn Phe Lys Glu Val Ile Trp Ala
            435                 440                 445

Tyr Val Thr Arg His Thr Pro Val Ala Asp Gln Met Ala Phe Asp Asp
            450                 455                 460

Val Thr Ser Phe Pro Leu Ala Pro Phe Val Ser Gln Ser Ser Arg Ser
465                 470                 475                 480

Lys Thr Met Lys Gly Gly Lys Cys Val Thr Asn Cys Ile Phe Arg Gln
            485                 490                 495

Gln Tyr Glu Arg Ser Phe Asp Tyr Ile Thr Cys Asn Phe Glu Lys Gly
            500                 505                 510

Tyr Pro Lys Gly Leu Val Asp Lys Val Asn Glu Asn Trp Lys Arg Tyr
            515                 520                 525

Gly Tyr Lys Ser Gly Gly Ser Gly Gly Ser Gly Ala Met Asp Gln Ile
            530                 535                 540

Glu Ala Met Leu Cys Gly Gly Glu Lys Thr Lys Val Ala Val Thr
545                 550                 555                 560

Thr Lys Thr Leu Ala Asp Pro Leu Asn Trp Gly Leu Ala Ala Asp Gln
            565                 570                 575

Met Lys Gly Ser His Leu Asp Glu Val Lys Lys Met Val Glu Glu Tyr
            580                 585                 590

Arg Arg Pro Val Val Asn Leu Gly Gly Glu Thr Leu Thr Ile Gly Gln
```

```
                595                 600                 605
    Val Ala Ala Ile Ser Thr Val Gly Ser Val Lys Val Glu Leu Ala
    610                 615                 620

Glu Thr Ser Arg Ala Gly Val Lys Ala Ser Ser Asp Trp Val Met Glu
    625                 630                 635                 640

Ser Met Asn Lys Gly Thr Asp Ser Tyr Gly Val Thr Thr Gly Phe Gly
                    645                 650                 655

Ala Thr Ser His Arg Arg Thr Lys Asn Gly Thr Ala Leu Gln Thr Glu
                    660                 665                 670

Leu Ile Arg Phe Leu Asn Ala Gly Ile Phe Gly Asn Thr Lys Glu Thr
                    675                 680                 685

Cys His Thr Leu Pro Gln Ser Ala Thr Arg Ala Ala Met Leu Val Arg
                    690                 695                 700

Val Asn Thr Leu Leu Gln Gly Tyr Ser Gly Ile Arg Phe Glu Ile Leu
    705                 710                 715                 720

Glu Ala Ile Thr Ser Leu Leu Asn His Asn Ile Ser Pro Ser Leu Pro
                    725                 730                 735

Leu Arg Gly Thr Ile Thr Ala Ser Gly Asp Leu Val Pro Leu Ser Tyr
                    740                 745                 750

Ile Ala Gly Leu Leu Thr Gly Arg Pro Asn Ser Lys Ala Thr Gly Pro
                    755                 760                 765

Asp Gly Glu Ser Leu Thr Ala Lys Glu Ala Phe Glu Lys Ala Gly Ile
                    770                 775                 780

Ser Thr Gly Phe Phe Asp Leu Gln Pro Lys Glu Gly Leu Ala Leu Val
    785                 790                 795                 800

Asn Gly Thr Ala Val Gly Ser Gly Met Ala Ser Met Val Leu Phe Glu
                    805                 810                 815

Ala Asn Val Gln Ala Val Leu Ala Glu Val Leu Ser Ala Ile Phe Ala
                    820                 825                 830

Glu Val Met Ser Gly Lys Pro Glu Phe Thr Asp His Leu Thr His Arg
                    835                 840                 845

Leu Lys His His Pro Gly Gln Ile Glu Ala Ala Ala Ile Met Glu His
                    850                 855                 860

Ile Leu Asp Gly Ser Ser Tyr Met Lys Leu Ala Gln Lys Val His Glu
    865                 870                 875                 880

Met Asp Pro Leu Gln Lys Pro Lys Gln Asp Arg Tyr Ala Leu Arg Thr
                    885                 890                 895

Ser Pro Gln Trp Leu Gly Pro Gln Ile Glu Val Ile Arg Gln Ala Thr
                    900                 905                 910

Lys Ser Ile Glu Arg Glu Ile Asn Ser Val Asn Asp Asn Pro Leu Ile
                    915                 920                 925

Asp Val Ser Arg Asn Lys Ala Ile His Gly Gly Asn Phe Gln Gly Thr
                    930                 935                 940

Pro Ile Gly Val Ser Met Asp Asn Thr Arg Leu Ala Ile Ala Ala Ile
    945                 950                 955                 960

Gly Lys Leu Met Phe Ala Gln Phe Ser Glu Leu Val Asn Asp Phe Tyr
                    965                 970                 975

Asn Asn Gly Leu Pro Ser Asn Leu Thr Ala Ser Ser Asn Pro Ser Leu
                    980                 985                 990

Asp Tyr Gly Phe Lys Gly Ala Glu Ile Ala Met Ala Ser Tyr Cys Ser
                    995                 1000                1005

Glu Leu Gln Tyr Leu Ala Asn Pro Val Thr Ser His Val Gln Ser
                    1010                1015                1020
```

| | | | | | | | | | | |
|---|---|---|---|---|---|---|---|---|---|---|
| Ala | Glu | Gln | His | Asn | Gln | Asp | Val | Asn | Ser | Leu | Gly | Leu | Ile | Ser |
| | 1025 | | | | 1030 | | | | 1035 | |

Ala Glu Gln His Asn Gln Asp Val Asn Ser Leu Gly Leu Ile Ser
    1025                1030                1035

Ser Arg Lys Thr Ser Glu Ala Val Asp Ile Leu Lys Leu Met Ser
    1040                1045                1050

Thr Thr Phe Leu Val Gly Ile Cys Gln Ala Val Asp Leu Arg His
    1055                1060                1065

Leu Glu Glu Asn Leu Arg Gln Thr Val Lys Asn Thr Val Ser Gln
    1070                1075                1080

Val Ala Lys Lys Val Leu Thr Thr Gly Ile Asn Gly Glu Leu His
    1085                1090                1095

Pro Ser Arg Phe Cys Glu Lys Asp Leu Leu Lys Val Val Asp Arg
    1100                1105                1110

Glu Gln Val Phe Thr Tyr Val Asp Asp Pro Cys Ser Ala Thr Tyr
    1115                1120                1125

Pro Leu Met Gln Arg Leu Arg Gln Val Ile Val Asp His Ala Leu
    1130                1135                1140

Ser Asn Gly Glu Thr Glu Lys Asn Ala Val Thr Ser Ile Phe Gln
    1145                1150                1155

Lys Ile Gly Ala Phe Glu Glu Glu Leu Lys Ala Val Leu Pro Lys
    1160                1165                1170

Glu Val Glu Ala Ala Arg Ala Ala Tyr Gly Asn Gly Thr Ala Pro
    1175                1180                1185

Ile Pro Asn Arg Ile Lys Glu Cys Arg Ser Tyr Pro Leu Tyr Arg
    1190                1195                1200

Phe Val Arg Glu Glu Leu Gly Thr Lys Leu Leu Thr Gly Glu Lys
    1205                1210                1215

Val Val Ser Pro Gly Glu Glu Phe Asp Lys Val Phe Thr Ala Met
    1220                1225                1230

Cys Glu Gly Lys Leu Ile Asp Pro Leu Met Asp Cys Leu Lys Glu
    1235                1240                1245

Trp Asn Gly Ala Pro Ile Pro Ile Cys
    1250                1255

```
<210> SEQ ID NO 15
<211> LENGTH: 1512
<212> TYPE: DNA
<213> ORGANISM: Artificial Sequence
<220> FEATURE:
<223> OTHER INFORMATION: Synthetic

<400> SEQUENCE: 15
```

| | |
|---|---|
| atgaggaagc taaatccagc tttagaattt agagacttta tccaggtctt aaaagatgaa | 60 |
| gatgacttaa tcgaaattac cgaagagatt gatccaaatc tcgaagtagg tgcaattatg | 120 |
| aggaaggcct atgaatccca cttaccagcc ccgttattta aaatctcaa aggtgcttcg | 180 |
| aaggatcttt tcagcatttt aggttgccca gccggtttga agtaagga aaaggagat | 240 |
| catggtagaa ttgcccatca tctggggctc gacccaaaaa caactatcaa ggaaatcata | 300 |
| gattatttgc tggagtgtaa ggagaaggaa cctctccccc caatcactgt tcctgtgtca | 360 |
| tctgcacctt gtaaaacaca tatactttct gaagaaaaaa tacatctaca aagcctgcca | 420 |
| acaccatatc tacatgtttc agacggtggc aagtacttac aaacgtacgg aatgtggatt | 480 |
| cttcaaactc cagataaaaa atggactaat tggtcaattg ctagaggtat ggttgtagat | 540 |
| gacaagcata tcactggtct ggtaattgag ccacaacata ttagacaaat tgctgactct | 600 |

```
tgggcagcaa ttggaaaagc aaatgaaatt cctttcgcgt tatgttttgg cgttcccca     660 gcagctattt tagttagttc catgccaatt cctgaaggtg tttctgaatc ggattatgtt     720
ggcgcaatct tgggtgagtc ggttccagta gtaaaatgtg agaccaacga tttaatggtt     780
cctgcaacga gtgagatggt atttgagggt actttgtcct taacagatac acatctggaa     840
ggcccatttg gtgagatgca tggatatgtt ttcaaaagcc aaggtcatcc ttgtccattg     900
tacactgtca aggctatgag ttacagagac aatgctattc tacctgtttc gaacccccggt    960 ctttgtacgg atgagacaca taccttgatt ggttcactag tggctactga ggccaaggag    1020
ctggctattg aatctggctt gccaattctg gatgccttta tgccttatga ggctcaggct    1080
ctttggctta tcttaaaggt ggatttgaaa gggctgcaag cattgaagac aacgcctgaa    1140
gaattttgta agaaggtagg tgatatttac tttaggacaa agttggtttt tatagtccat    1200
gaaataattt tggtggcaga tgatatcgac atatttaact tcaaagaagt catctgggcc    1260
tacgttacaa gacatacacc tgttgcagat cagatggctt ttgatgatgt cacttctttt    1320
cctttggctc cctttgtttc gcagtcatcc agaagtaaga ctatgaaagg tggaaagtgc    1380
gttactaatt gcatatttag acagcaatat gagcgcagtt ttgactacat aacttgtaat    1440
tttgaaaagg gatatccaaa aggattagtt gacaaagtaa atgaaaattg gaaaggtac     1500 ggatataaat aa                                                        1512
```

<210> SEQ ID NO 16
<211> LENGTH: 503
<212> TYPE: PRT
<213> ORGANISM: Artificial Sequence
<220> FEATURE:
<223> OTHER INFORMATION: Synthetic

<400> SEQUENCE: 16

```
Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
        115                 120                 125

Leu Ser Glu Glu Lys Ile His Leu Gln Ser Leu Pro Thr Pro Tyr Leu
    130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Glu Pro Gln
            180                 185                 190

His Ile Arg Gln Ile Ala Asp Ser Trp Ala Ala Ile Gly Lys Ala Asn
```

```
                    195                 200                 205
Glu Ile Pro Phe Ala Leu Cys Phe Gly Val Pro Ala Ala Ile Leu
    210                 215                 220
Val Ser Ser Met Pro Ile Pro Glu Gly Val Ser Glu Ser Asp Tyr Val
225                 230                 235                 240
Gly Ala Ile Leu Gly Glu Ser Val Pro Val Lys Cys Glu Thr Asn
            245                 250                 255
Asp Leu Met Val Pro Ala Thr Ser Glu Met Val Phe Glu Gly Thr Leu
            260                 265                 270
Ser Leu Thr Asp Thr His Leu Glu Gly Pro Phe Gly Glu Met His Gly
            275                 280                 285
Tyr Val Phe Lys Ser Gln Gly His Pro Cys Pro Leu Tyr Thr Val Lys
            290                 295                 300
Ala Met Ser Tyr Arg Asp Asn Ala Ile Leu Pro Val Ser Asn Pro Gly
305                 310                 315                 320
Leu Cys Thr Asp Glu Thr His Thr Leu Ile Gly Ser Leu Val Ala Thr
                325                 330                 335
Glu Ala Lys Glu Leu Ala Ile Glu Ser Gly Leu Pro Ile Leu Asp Ala
            340                 345                 350
Phe Met Pro Tyr Glu Ala Gln Ala Leu Trp Leu Ile Leu Lys Val Asp
            355                 360                 365
Leu Lys Gly Leu Gln Ala Leu Lys Thr Thr Pro Glu Glu Phe Cys Lys
            370                 375                 380
Lys Val Gly Asp Ile Tyr Phe Arg Thr Lys Val Gly Phe Ile Val His
385                 390                 395                 400
Glu Ile Ile Leu Val Ala Asp Asp Ile Asp Ile Phe Asn Phe Lys Glu
                405                 410                 415
Val Ile Trp Ala Tyr Val Thr Arg His Thr Pro Val Ala Asp Gln Met
            420                 425                 430
Ala Phe Asp Asp Val Thr Ser Phe Pro Leu Ala Pro Phe Val Ser Gln
            435                 440                 445
Ser Ser Arg Ser Lys Thr Met Lys Gly Gly Lys Cys Val Thr Asn Cys
450                 455                 460
Ile Phe Arg Gln Gln Tyr Glu Arg Ser Phe Asp Tyr Ile Thr Cys Asn
465                 470                 475                 480
Phe Glu Lys Gly Tyr Pro Lys Gly Leu Val Asp Lys Val Asn Glu Asn
                485                 490                 495
Trp Lys Arg Tyr Gly Tyr Lys
                500

<210> SEQ ID NO 17
<211> LENGTH: 1512
<212> TYPE: DNA
<213> ORGANISM: Artificial Sequence
<220> FEATURE:
<223> OTHER INFORMATION: Synthetic

<400> SEQUENCE: 17
atgaggaagc taaatccagc tttagaattt agagacttta tccaggtctt aaaagatgaa    60
gatgacttaa tcgaaattac cgaagagatt gatccaaatc tcgaagtagg tgcaattatg   120
aggaaggcct atgaatccca cttaccagcc ccgttattta aaatctcaa aggtgcttcg    180 aaggatcttt tcagcatttt aggttgccca gccggtttga agtaagga gaaaggagat    240 catggtagaa ttgcccatca tctggggctc gacccaaaaa caactatcaa ggaaatcata   300
```

```
gattatttgc tggagtgtaa ggagaaggaa cctctccccc caatcactgt tcctgtgtca    360 tctgcaccit gtaaaacaca tatactitct gaagaaaaaa tacatctaca aagcctgcca    420
acaccatatc tacatgttic agacggtggc aagtacttac aaacgtacgg aatgtggatt    480
cttcaaactc cagataaaaa atggactaat tggtcaattg ctagaggtat ggttgtagat    540
gacaagcata tcactggtct ggtaatttgt ccacaacata ttagacaaat tgctgactct    600
tgggcagcaa ttggaaaagc aaatgaaatt cctttcgcgt tatgttttgg cgttccccca    660
gcagctattt tagttagttc catgccaatt cctgaaggtg tttctgaatc ggattatgtt    720
ggcgcaatct tgggtgagtc ggttccagta gtaaaatgtg agaccaacga tttaatggtt    780
cctgcaacga gtgagatggt atttgagggt actttgtcct aacagatac acatctggaa     840 ggcccatttg gtgagatgca tggatatgtt ttcaaaagcc aaggtcatcc ttgtccattg    900
tacactgtca aggctatgag ttacagagac aatgctattc tacctgtttc gaaccccggt    960
ctttgtacgg atgagacaca taccttgatt ggttcactag tggctactga ggccaaggag   1020
ctggctattg aatctggctt gccaattctg gatgcctttta tgccttatga ggctcaggct   1080
ctttggctta tcttaaaggt ggatttgaaa gggctgcaag cattgaagac aacgcctgaa   1140
gaattttgta agaaggtagg tgatatttac tttaggacaa agttggtttt tatagtccat   1200
gaaataattt tggtggcaga tgatatcgac atatttaact tcaaagaagt catctgggcc   1260
tacgttacaa gacatacacc tgttgcagat cagatggctt ttgatgatgt cacttctttt   1320
cctttggctc cctttgtttc gcagtcatcc agaagtaaga ctatgaaagg tggaaagtgc   1380
gttactaatt gcatatttag acagcaatat gagcgcagtt ttgactacat aacttgtaat   1440
tttgaaaagg gatatccaaa aggattagtt gacaaagtaa atgaaaattg gaaaaggtac   1500
ggatataaat aa                                                       1512
```

<210> SEQ ID NO 18
<211> LENGTH: 503
<212> TYPE: PRT
<213> ORGANISM: Artificial Sequence
<220> FEATURE:
<223> OTHER INFORMATION: Synthetic

<400> SEQUENCE: 18

```
Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
        115                 120                 125

Leu Ser Glu Glu Lys Ile His Leu Gln Ser Leu Pro Thr Pro Tyr Leu
    130                 135                 140
```

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
            165                 170                 175

Met Val Asp Asp Lys His Ile Thr Gly Leu Val Ile Cys Pro Gln
        180                 185                 190

His Ile Arg Gln Ile Ala Asp Ser Trp Ala Ala Ile Gly Lys Ala Asn
        195                 200                 205

Glu Ile Pro Phe Ala Leu Cys Phe Gly Val Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Val Lys Cys Glu Thr Asn
                245                 250                 255

Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
        275                 280                 285

Tyr Val Phe Lys Ser Gln Gly His Pro Cys Pro Leu Tyr Thr Val Lys
290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
        355                 360                 365

Leu Lys Gly Leu Gln Ala Leu Lys Thr Thr Pro Glu Glu Phe Cys Lys
    370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
        435                 440                 445

Ser Ser Arg Ser Lys Thr Met Lys Gly Gly Lys Cys Val Thr Asn Cys
    450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500

<210> SEQ ID NO 19
<211> LENGTH: 1512
<212> TYPE: DNA
<213> ORGANISM: Artificial Sequence
<220> FEATURE:
<223> OTHER INFORMATION: Synthetic

<400> SEQUENCE: 19

```
atgaggaagc taaatccagc tttagaattt agagacttta tccaggtctt aaaagatgaa      60
gatgacttaa tcgaaattac cgaagagatt gatccaaatc tcgaagtagg tgcaattatg     120
aggaaggcct atgaatccca cttaccagcc ccgttattta aaaatctcaa aggtgcttcg     180
aaggatcttt tcagcatttt aggttgccca gccggtttga agtaagga gaaaggagat      240 catggtagaa ttgcccatca tctggggctc gacccaaaaa caactatcaa ggaaatcata     300
gattatttgc tggagtgtaa ggagaaggaa cctctccccc caatcactgt tcctgtgtca     360
tctgcacctt gtaaaacaca tatactttct gaagaaaaaa tacatctaca aagcctgcca     420
acaccatatc tacatgtttc agacggtggc aagtacttac aaacgtacgg aatgtggatt     480
cttcaaactc cagataaaaa atggactaat tggtcaattg ctagaggtat ggttgtagat     540
gacaagcata tcactggtct ggtaattcat ccacaacata ttagacaaat tgctgactct     600
tgggcagcaa ttggaaaagc aaatgaaatt cctttcgcgt tatgttttgg cgttccccca     660
gcagctattt tagttagttc catgccaatt cctgaaggtg tttctgaatc ggattatgtt     720
ggcgcaatct gggtgagtc ggttccagta gtaaaatgtg agaccaacga tttaatggtt     780
cctgcaacga gtgagatggt atttgagggt actttgtcct taacagatac acatctggaa     840
ggcccatttg gtgagatgca tggatatgtt ttcaaaagcc aaggtcatcc ttgtccattg     900
tacactgtca aggctatgag ttacagagac aatgctattc tacctgtttc gaaccccggt     960
ctttgtacgg atgagacaca taccttgatt ggttcactag tggctactga ggccaaggag    1020
ctggctattg aatctggctt gccaattctg gatgccttta tgccttatga ggctcaggct    1080
ctttggctta tcttaaaggt ggatttgaaa gggctgcaag cattgaagac aacgcctgaa    1140
gaattttgta agaaggtagg tgatatttac tttaggacaa aagttggttt tatagtccat    1200
gaaataattt tggtggcaga tgatatcgac atatttaact tcaaagaagt catctgggcc    1260
tacgttacaa gacatacacc tgttgcagat cagatggctt ttgatgatgt cacttctttt    1320
cctttggctc cctttgtttc gcagtcatcc agaagtaaga ctatgaaagg tggaaagtgc    1380
gttactaatt gcatatttag acagcaatat gagcgcagtt ttgactacat aacttgtaat    1440
tttgaaaagg gatatccaaa aggattagtt gacaaagtaa atgaaaattg gaaaaggtac    1500
ggatataaat aa                                                        1512
```

<210> SEQ ID NO 20
<211> LENGTH: 503
<212> TYPE: PRT
<213> ORGANISM: Artificial Sequence
<220> FEATURE:
<223> OTHER INFORMATION: Synthetic

<400> SEQUENCE: 20

```
Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
            85                  90                  95
```

-continued

```
Lys Glu Ile Ile Asp Tyr Leu Leu Glu Cys Lys Glu Lys Glu Pro Leu
            100                 105                 110
Pro Pro Ile Thr Val Pro Val Ser Ser Ala Pro Cys Lys Thr His Ile
            115                 120                 125
Leu Ser Glu Glu Lys Ile His Leu Gln Ser Leu Pro Thr Pro Tyr Leu
130                 135                 140
His Val Ser Asp Gly Gly Lys Tyr Leu Gln Thr Tyr Gly Met Trp Ile
145                 150                 155                 160
Leu Gln Thr Pro Asp Lys Lys Trp Thr Asn Trp Ser Ile Ala Arg Gly
                165                 170                 175
Met Val Val Asp Asp Lys His Ile Thr Gly Leu Val Ile His Pro Gln
            180                 185                 190
His Ile Arg Gln Ile Ala Asp Ser Trp Ala Ala Ile Gly Lys Ala Asn
            195                 200                 205
Glu Ile Pro Phe Ala Leu Cys Phe Gly Val Pro Pro Ala Ala Ile Leu
            210                 215                 220
Val Ser Ser Met Pro Ile Pro Glu Gly Val Ser Glu Ser Asp Tyr Val
225                 230                 235                 240
Gly Ala Ile Leu Gly Glu Ser Val Pro Val Val Lys Cys Glu Thr Asn
                245                 250                 255
Asp Leu Met Val Pro Ala Thr Ser Glu Met Val Phe Glu Gly Thr Leu
            260                 265                 270
Ser Leu Thr Asp Thr His Leu Glu Gly Pro Phe Gly Glu Met His Gly
            275                 280                 285
Tyr Val Phe Lys Ser Gln Gly His Pro Cys Pro Leu Tyr Thr Val Lys
            290                 295                 300
Ala Met Ser Tyr Arg Asp Asn Ala Ile Leu Pro Val Ser Asn Pro Gly
305                 310                 315                 320
Leu Cys Thr Asp Glu Thr His Thr Leu Ile Gly Ser Leu Val Ala Thr
                325                 330                 335
Glu Ala Lys Glu Leu Ala Ile Glu Ser Gly Leu Pro Ile Leu Asp Ala
            340                 345                 350
Phe Met Pro Tyr Glu Ala Gln Ala Leu Trp Leu Ile Leu Lys Val Asp
            355                 360                 365
Leu Lys Gly Leu Gln Ala Leu Lys Thr Thr Pro Glu Glu Phe Cys Lys
            370                 375                 380
Lys Val Gly Asp Ile Tyr Phe Arg Thr Lys Val Gly Phe Ile Val His
385                 390                 395                 400
Glu Ile Ile Leu Val Ala Asp Asp Ile Asp Ile Phe Asn Phe Lys Glu
                405                 410                 415
Val Ile Trp Ala Tyr Val Thr Arg His Thr Pro Val Ala Asp Gln Met
            420                 425                 430
Ala Phe Asp Asp Val Thr Ser Phe Pro Leu Ala Pro Phe Val Ser Gln
            435                 440                 445
Ser Ser Arg Ser Lys Thr Met Lys Gly Gly Lys Cys Val Thr Asn Cys
            450                 455                 460
Ile Phe Arg Gln Gln Tyr Glu Arg Ser Phe Asp Tyr Ile Thr Cys Asn
465                 470                 475                 480
Phe Glu Lys Gly Tyr Pro Lys Gly Leu Val Asp Lys Val Asn Glu Asn
                485                 490                 495
Trp Lys Arg Tyr Gly Tyr Lys
            500
```

<210> SEQ ID NO 21
<211> LENGTH: 1512
<212> TYPE: DNA
<213> ORGANISM: Artificial Sequence
<220> FEATURE:
<223> OTHER INFORMATION: Synthetic

<400> SEQUENCE: 21

| | |
|---|---|
| atgaggaagc taaatccagc tttagaattt agagacttta tccaggtctt aaaagatgaa | 60 |
| gatgacttaa tcgaaattac cgaagagatt gatccaaatc tcgaagtagg tgcaattatg | 120 |
| aggaaggcct atgaatccca cttaccagcc ccgttattta aaaatctcaa aggtgcttcg | 180 |
| aaggatcttt tcagcatttt aggttgccca gccggtttga agtaagga gaaaggagat | 240 |
| catggtagaa ttgcccatca tctggggctc gacccaaaaa caactatcaa ggaaatcata | 300 |
| gattatttgc tggagtgtaa ggagaaggaa cctctccccc caatcactgt tcctgtgtca | 360 |
| tctgcacctt gtaaaacaca tatactttct gaagaaaaaa tacatctaca agcctgcca | 420 |
| acaccatatc tacatgtttc agacggtggc aagtacttac aaacgtacgg aatgtggatt | 480 |
| cttcaaactc cagataaaaa atggactaat tggtcaattg ctagaggtat ggttgtagat | 540 |
| gacaagcata tcactggtct ggtaattcct ccacaacata ttagacaaat tgctgactct | 600 |
| tgggcagcaa ttggaaaagc aaatgaaatt cctttcgcgt tatgttttgg cgttcccca | 660 |
| gcagctattt tagttagttc catgccaatt cctgaaggtg tttctgaatc ggattatgtt | 720 |
| ggcgcaatct gggtgagtc ggttccagta gtaaaatgtg agaccaacga tttaatggtt | 780 |
| cctgcaacga gtgagatggt atttgagggt actttgtcct taacagatac acatctggaa | 840 |
| ggcccatttg gtgagatgca tggatatgtt ttcaaaagcc aaggtcatcc ttgtccattg | 900 |
| tacactgtca aggctatgag ttacagagac aatgctattc tacctgtttc gaaccccggt | 960 |
| ctttgtacgg atgagacaca taccttgatt ggttcactag tggctactga ggccaaggag | 1020 |
| ctggctattg aatctggctt gccaattctg gatgccttta tgccttatga ggctcaggct | 1080 |
| ctttggctta tcttaaaggt ggatttgaaa gggctgcaag cattgaagac aacgcctgaa | 1140 |
| gaattttgta agaaggtagg tgatatttac tttaggacaa agttggttt tatagtccat | 1200 |
| gaaataattt tggtggcaga tgatatcgac atatttaact tcaaagaagt catctgggcc | 1260 |
| tacgttacaa gacatacacc tgttgcagat cagatggctt ttgatgatgt cacttctttt | 1320 |
| cctttggctc cctttgtttc gcagtcatcc agaagtaaga ctatgaaagg tggaaagtgc | 1380 |
| gttactaatt gcatatttag acagcaatat gagcgcagtt ttgactacat aacttgtaat | 1440 |
| tttgaaaagg gatatccaaa aggattagtt gacaaagtaa atgaaaattg gaaaaggtac | 1500 |
| ggatataaat aa | 1512 |

<210> SEQ ID NO 22
<211> LENGTH: 503
<212> TYPE: PRT
<213> ORGANISM: Artificial Sequence
<220> FEATURE:
<223> OTHER INFORMATION: Synthetic

<400> SEQUENCE: 22

Met Arg Lys Leu Asn Pro Ala Leu Glu Phe Arg Asp Phe Ile Gln Val
1               5                   10                  15

Leu Lys Asp Glu Asp Asp Leu Ile Glu Ile Thr Glu Glu Ile Asp Pro
            20                  25                  30

Asn Leu Glu Val Gly Ala Ile Met Arg Lys Ala Tyr Glu Ser His Leu

```
                35                  40                  45
Pro Ala Pro Leu Phe Lys Asn Leu Lys Gly Ala Ser Lys Asp Leu Phe
 50                  55                  60
Ser Ile Leu Gly Cys Pro Ala Gly Leu Arg Ser Lys Glu Lys Gly Asp
 65                  70                  75                  80
His Gly Arg Ile Ala His His Leu Gly Leu Asp Pro Lys Thr Thr Ile
                 85                  90                  95
Lys Glu Ile Ile Asp Tyr Leu Leu Glu Cys Lys Glu Lys Glu Pro Leu
                100                 105                 110
Pro Pro Ile Thr Val Pro Val Ser Ser Ala Pro Cys Lys Thr His Ile
                115                 120                 125
Leu Ser Glu Glu Lys Ile His Leu Gln Ser Leu Pro Thr Pro Tyr Leu
                130                 135                 140
His Val Ser Asp Gly Gly Lys Tyr Leu Gln Thr Tyr Gly Met Trp Ile
145                 150                 155                 160
Leu Gln Thr Pro Asp Lys Lys Trp Thr Asn Trp Ser Ile Ala Arg Gly
                165                 170                 175
Met Val Val Asp Asp Lys His Ile Thr Gly Leu Val Ile Pro Pro Gln
                180                 185                 190
His Ile Arg Gln Ile Ala Asp Ser Trp Ala Ala Ile Gly Lys Ala Asn
                195                 200                 205
Glu Ile Pro Phe Ala Leu Cys Phe Gly Val Pro Pro Ala Ala Ile Leu
                210                 215                 220
Val Ser Ser Met Pro Ile Pro Glu Gly Val Ser Glu Ser Asp Tyr Val
225                 230                 235                 240
Gly Ala Ile Leu Gly Glu Ser Val Pro Val Lys Cys Glu Thr Asn
                245                 250                 255
Asp Leu Met Val Pro Ala Thr Ser Glu Met Val Phe Glu Gly Thr Leu
                260                 265                 270
Ser Leu Thr Asp Thr His Leu Glu Gly Pro Phe Gly Glu Met His Gly
                275                 280                 285
Tyr Val Phe Lys Ser Gln Gly His Pro Cys Pro Leu Tyr Thr Val Lys
                290                 295                 300
Ala Met Ser Tyr Arg Asp Asn Ala Ile Leu Pro Val Ser Asn Pro Gly
305                 310                 315                 320
Leu Cys Thr Asp Glu Thr His Thr Leu Ile Gly Ser Leu Val Ala Thr
                325                 330                 335
Glu Ala Lys Glu Leu Ala Ile Glu Ser Gly Leu Pro Ile Leu Asp Ala
                340                 345                 350
Phe Met Pro Tyr Glu Ala Gln Ala Leu Trp Leu Ile Leu Lys Val Asp
                355                 360                 365
Leu Lys Gly Leu Gln Ala Leu Lys Thr Thr Pro Glu Glu Phe Cys Lys
                370                 375                 380
Lys Val Gly Asp Ile Tyr Phe Arg Thr Lys Val Gly Phe Ile Val His
385                 390                 395                 400
Glu Ile Ile Leu Val Ala Asp Asp Ile Asp Ile Phe Asn Phe Lys Glu
                405                 410                 415
Val Ile Trp Ala Tyr Val Thr Arg His Thr Pro Val Ala Asp Gln Met
                420                 425                 430
Ala Phe Asp Asp Val Thr Ser Phe Pro Leu Ala Pro Phe Val Ser Gln
                435                 440                 445
Ser Ser Arg Ser Lys Thr Met Lys Gly Gly Lys Cys Val Thr Asn Cys
                450                 455                 460
```

```
Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500
```

<210> SEQ ID NO 23
<211> LENGTH: 1512
<212> TYPE: DNA
<213> ORGANISM: Artificial Sequence
<220> FEATURE:
<223> OTHER INFORMATION: Synthetic

<400> SEQUENCE: 23

```
atgaggaagc taaatccagc tttagaattt agagacttta tccaggtctt aaaagatgaa      60
gatgacttaa tcgaaattac cgaagagatt gatccaaatc tcgaagtagg tgcaattatg     120
aggaaggcct atgaatccca cttaccagcc ccgttattta aaaatctcaa aggtgcttcg     180
aaggatcttt tcagcatttt aggttgccca gccggtttga aagtaagga gaaaggagat     240
catggtagaa ttgcccatca tctggggctc gacccaaaaa caactatcaa ggaaatcata     300
gattatttgc tggagtgtaa ggagaaggaa cctctccccc caatcactgt tcctgtgtca     360
tctgcacctt gtaaaacaca tactttctt gaagaaaaaa tacatctaca aagcctgcca     420
acaccatatc tacatgtttc agacggtggc aagtacttac aaacgtacgg aatgtggatt     480
cttcaaactc cagataaaaa atggactaat tggtcaattg ctagaggtat ggttgtagat     540
gacaagcata tcactggtct ggtaattctg ccacaacata ttagacaaat tgctgactct     600
tgggcagcaa ttggaaaagc aaatgaaatt cctttcgcgt tatgttttgg cgttccccca     660
gcagctattt tagttagttc catgccaatt cctgaaggtg tttctgaatc ggattatgtt     720
ggcgcaatct gggtgagtc ggttccagta gtaaaatgtg agaccaacga tttaatggtt     780
cctgcaacga gtgagatggt atttgagggt actttgtcct aacagatac acatctggaa     840
ggcccatttg gtgagatgca tggatatgtt ttcaaaagcc aaggtcatcc ttgtccattg     900
tacactgtca aggctatgag ttacagagac aatgctattc tacctgtttc gaaccccggt     960
ctttgtacgg atgagacaca taccttgatt ggttcactag tggctactga ggccaaggag    1020
ctggctattg aatctggctt gccaattctg gatgccttta tgccttatga ggctcaggct    1080
ctttggctta tcttaaaggt ggatttgaaa gggctgcaag cattgaagac aacgcctgaa    1140
gaattttgta agaaggtagg tgatatttac tttaggacaa aagttggttt tatagtccat    1200
gaaataattt tggtggcaga tgatatcgac atatttaact tcaaagaagt catctgggcc    1260
tacgttacaa gacatacacc tgttgcagat cagatggctt ttgatgatgt cacttctttt    1320
cctttggctc cctttgtttc gcagtcatcc agaagtaaga ctatgaaagg tggaaagtgc    1380
gttactaatt gcatatttag acagcaatat gagcgcagtt ttgactacat aacttgtaat    1440
tttgaaaagg gatatccaaa aggattagtt gacaaagtaa atgaaaattg gaaaaggtac    1500
ggatataaat aa                                                        1512
```

<210> SEQ ID NO 24
<211> LENGTH: 503
<212> TYPE: PRT
<213> ORGANISM: Artificial Sequence
<220> FEATURE:
<223> OTHER INFORMATION: Synthetic

<400> SEQUENCE: 24

Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
                100                 105                 110

Pro Pro Ile Thr Val Pro Val Ser Ser Ala Pro Cys Lys Thr His Ile
            115                 120                 125

Leu Ser Glu Glu Lys Ile His Leu Gln Ser Leu Pro Thr Pro Tyr Leu
130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Leu Pro Gln
            180                 185                 190

His Ile Arg Gln Ile Ala Asp Ser Trp Ala Ala Ile Gly Lys Ala Asn
        195                 200                 205

Glu Ile Pro Phe Ala Leu Cys Phe Gly Val Pro Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Lys Cys Glu Thr Asn
                245                 250                 255

Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
        275                 280                 285

Tyr Val Phe Lys Ser Gln Gly His Pro Cys Pro Leu Tyr Thr Val Lys
    290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
        355                 360                 365

Leu Lys Gly Leu Gln Ala Leu Lys Thr Thr Pro Glu Glu Phe Cys Lys
    370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu

```
            405                 410                 415
Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
            435                 440                 445

Ser Ser Arg Ser Lys Thr Met Lys Gly Gly Lys Cys Val Thr Asn Cys
            450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
            485                 490                 495

Trp Lys Arg Tyr Gly Tyr Lys
            500

<210> SEQ ID NO 25
<211> LENGTH: 1512
<212> TYPE: DNA
<213> ORGANISM: Artificial Sequence
<220> FEATURE:
<223> OTHER INFORMATION: Synthetic

<400> SEQUENCE: 25
atgaggaagc taaatccagc tttagaattt agagacttta tccaggtctt aaaagatgaa      60
gatgacttaa tcgaaattac cgaagagatt gatccaaatc tcgaagtagg tgcaattatg     120
aggaaggcct atgaatccca cttaccagcc ccgttattta aaaatctcaa aggtgcttcg     180
aaggatcttt tcagcatttt aggttgccca gccggtttga aagtaaggaa aaggagat     240 catggtagaa ttgcccatca tctggggctc gacccaaaaa caactatcaa ggaaatcata     300
gattatttgc tggagtgtaa ggagaaggaa cctctccccc aatcactgt tcctgtgtca     360 tctgcacctt gtaaaacaca tatactttct gaagaaaaaa tacatctaca aagcctgcca     420
acaccatatc tacatgtttc agacggtggc aagtacttac aaacgtacgg aatgtggatt     480
cttcaaactc cagataaaaa atggactaat tggtcaattg ctagaggtat ggttgtagat     540
gacaagcata tcactggtct ggtaattggg ccacaacata ttagacaaat tgctgactct     600
tgggcagcaa ttggaaaagc aaatgaaatt cctttcgcgt tatgttttgg cgttcccca     660 gcagctattt tagttagttc catgccaatt cctgaaggtg tttctgaatc ggattatgtt     720
ggcgcaatct gggtgagtc ggttccagta gtaaaatgtg agaccaacga tttaatggtt     780
cctgcaacga gtgagatggt atttgagggt actttgtcct taacagatac acatctggaa     840
ggcccatttg gtgagatgca tggatatgtt ttcaaaagcc aaggtcatcc ttgtccattg     900
tacactgtca aggctatgag ttacagagac aatgctattc tacctgtttc gaaccccggt     960
ctttgtacgg atgagacaca taccttgatt ggttcactag tggctactga ggccaaggag    1020
ctggctattg aatctggctt gccaattctg gatgccttta tgccttatga ggctcaggct    1080
ctttggctta tcttaaaggt ggatttgaaa gggctgcaag cattgaagac aacgcctgaa    1140
gaattttgta agaaggtagg tgatatttac tttaggacaa agttggttt tatagtccat    1200 gaaataattt tggtggcaga tgatatcgac atatttaact tcaaagaagt catctgggcc    1260
tacgttacaa gacatacacc tgttgcagat cagatggctt ttgatgatgt cacttcttt    1320 cctttggctc cctttgtttc gcagtcatcc agaagtaaga ctatgaaagg tggaaagtgc    1380
gttactaatt gcatatttag acagcaatat gagcgcagtt ttgactacat aacttgtaat    1440
tttgaaaagg gatatccaaa aggattagtt gacaaagtaa atgaaaattg gaaaaggtac    1500
```
ggatataaat aa                                                     1512

<210> SEQ ID NO 26
<211> LENGTH: 503
<212> TYPE: PRT
<213> ORGANISM: Artificial Sequence
<220> FEATURE:
<223> OTHER INFORMATION: Synthetic

<400> SEQUENCE: 26

Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ala Pro Cys Lys Thr His Ile
        115                 120                 125

Leu Ser Glu Glu Lys Ile His Leu Gln Ser Leu Pro Thr Pro Tyr Leu
130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Arg Pro Gln
            180                 185                 190

His Ile Arg Gln Ile Ala Asp Ser Trp Ala Ala Ile Gly Lys Ala Asn
        195                 200                 205

Glu Ile Pro Phe Ala Leu Cys Phe Gly Val Pro Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Lys Cys Glu Thr Asn
                245                 250                 255

Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
        275                 280                 285

Tyr Val Phe Lys Ser Gln Gly His Pro Cys Pro Leu Tyr Thr Val Lys
    290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

```
Phe Met Pro Tyr Glu Ala Gln Ala Leu Trp Leu Ile Leu Lys Val Asp
        355                 360                 365
Leu Lys Gly Leu Gln Ala Leu Lys Thr Thr Pro Glu Glu Phe Cys Lys
370                 375                 380
Lys Val Gly Asp Ile Tyr Phe Arg Thr Lys Val Gly Phe Ile Val His
385                 390                 395                 400
Glu Ile Ile Leu Val Ala Asp Asp Ile Asp Ile Phe Asn Phe Lys Glu
                405                 410                 415
Val Ile Trp Ala Tyr Val Thr Arg His Thr Pro Val Ala Asp Gln Met
            420                 425                 430
Ala Phe Asp Asp Val Thr Ser Phe Pro Leu Ala Pro Phe Val Ser Gln
        435                 440                 445
Ser Ser Arg Ser Lys Thr Met Lys Gly Gly Lys Cys Val Thr Asn Cys
    450                 455                 460
Ile Phe Arg Gln Gln Tyr Glu Arg Ser Phe Asp Tyr Ile Thr Cys Asn
465                 470                 475                 480
Phe Glu Lys Gly Tyr Pro Lys Gly Leu Val Asp Lys Val Asn Glu Asn
                485                 490                 495
Trp Lys Arg Tyr Gly Tyr Lys
            500
```

<210> SEQ ID NO 27
<211> LENGTH: 1512
<212> TYPE: DNA
<213> ORGANISM: Artificial Sequence
<220> FEATURE:
<223> OTHER INFORMATION: Synthetic

<400> SEQUENCE: 27

| | | | | | |
|---|---|---|---|---|---|
| atgaggaagc | taaatccagc | tttagaattt | agagactttta | tccaggtctt | aaaagatgaa | 60 |
| gatgacttaa | tcgaaattac | cgaagagatt | gatccaaatc | tcgaagtagg | tgcaattatg | 120 |
| aggaaggcct | atgaatccca | cttaccagcc | ccgttattta | aaaatctcaa | aggtgcttcg | 180 |
| aaggatcttt | tcagcatttt | aggttgccca | gccggtttga | aagtaagga | aaaggagat | 240 |
| catggtagaa | ttgcccatca | tctggggctc | gacccaaaaa | caactatcaa | ggaaatcata | 300 |
| gattatttgc | tggagtgtaa | ggagaaggaa | cctctcccc | caatcactgt | tcctgtgtca | 360 |
| tctgcacctt | gtaaaacaca | tatactttct | gaagaaaaaa | tacatctaca | aagcctgcca | 420 |
| acaccatatc | tacatgtttc | agacggtggc | aagtacttac | aaacgtacgg | aatgtggatt | 480 |
| cttcaaactc | cagataaaaa | atggactaat | tggtcaattg | ctagaggtat | ggttgtagat | 540 |
| gacaagcata | tcactggtct | ggtaattgat | ccacaacata | ttagacaaat | tgctgactct | 600 |
| tgggcagcaa | ttggaaaagc | aaatgaaatt | cctttcgcgt | tatgtttgg | cgttcccca | 660 |
| gcagctattt | tagttagttc | catgccaatt | cctgaaggtg | tttctgaatc | ggattatgtt | 720 |
| ggcgcaatct | tgggtgagtc | ggttccagta | gtaaaatgtg | agaccaacga | tttaatggtt | 780 |
| cctgcaacga | gtgagatggt | atttgagggt | actttgtcct | taacagatac | acatctggaa | 840 |
| ggcccatttg | gtgagatgca | tggatatgtt | ttcaaaagcc | aaggtcatcc | ttgtccattg | 900 |
| tacactgtca | aggctatgag | ttacagagac | aatgctattc | tacctgtttc | gaaccccggt | 960 |
| ctttgtacgg | atgagacaca | taccttgatt | ggttcactag | tggctactga | ggccaaggag | 1020 |
| ctggctattg | aatctggctt | gccaattctg | gatgccttta | tgccttatga | ggctcaggct | 1080 |
| ctttggctta | tcttaaaggt | tgggattgaa | agggctgcaag | cattgaagac | aacgcctgaa | 1140 |
| gaattttgta | agaaggtagg | tgatatttac | tttaggacaa | aagttggttt | tatagtccat | 1200 |

-continued

```
gaaataattt tggtggcaga tgatatcgac atatttaact tcaaagaagt catctgggcc    1260
tacgttacaa gacatacacc tgttgcagat cagatggctt ttgatgatgt cacttctttt    1320
cctttggctc cctttgtttc gcagtcatcc agaagtaaga ctatgaaagg tggaaagtgc    1380
gttactaatt gcatatttag acagcaatat gagcgcagtt ttgactacat aacttgtaat    1440
tttgaaaagg gatatccaaa aggattagtt gacaaagtaa atgaaaattg gaaaaggtac    1500
ggatataaat aa                                                        1512
```

<210> SEQ ID NO 28
<211> LENGTH: 503
<212> TYPE: PRT
<213> ORGANISM: Artificial Sequence
<220> FEATURE:
<223> OTHER INFORMATION: Synthetic

<400> SEQUENCE: 28

```
Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His Leu Gly Leu Asp Pro Lys Thr Thr Ile
                85                  90                  95

Lys Glu Ile Ile Asp Tyr Leu Leu Glu Cys Lys Glu Lys Glu Pro Leu
                100                 105                 110

Pro Pro Ile Thr Val Pro Val Ser Ser Ala Pro Cys Lys Thr His Ile
            115                 120                 125

Leu Ser Glu Glu Lys Ile His Leu Gln Ser Leu Pro Thr Pro Tyr Leu
    130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Asp Pro Gln
                180                 185                 190

His Ile Arg Gln Ile Ala Asp Ser Trp Ala Ala Ile Gly Lys Ala Asn
            195                 200                 205

Glu Ile Pro Phe Ala Leu Cys Phe Gly Val Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Lys Cys Glu Thr Asn
                245                 250                 255

Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
        275                 280                 285

Tyr Val Phe Lys Ser Gln Gly His Pro Cys Pro Leu Tyr Thr Val Lys
    290                 295                 300
```

```
Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
        355                 360                 365

Leu Lys Gly Leu Gln Ala Leu Lys Thr Thr Pro Glu Glu Phe Cys Lys
    370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
        435                 440                 445

Ser Ser Arg Ser Lys Thr Met Lys Gly Lys Cys Val Thr Asn Cys
    450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500
```

<210> SEQ ID NO 29
<211> LENGTH: 1512
<212> TYPE: DNA
<213> ORGANISM: Artificial Sequence
<220> FEATURE:
<223> OTHER INFORMATION: Synthetic

<400> SEQUENCE: 29

```
atgaggaagc taaatccagc tttagaattt agagacttta tccaggtctt aaaagatgaa    60
gatgacttaa tcgaaattac cgaagagatt gatccaaatc tcgaagtagg tgcaattatg   120
aggaaggcct atgaatccca cttaccagcc ccgttattta aaaatctcaa aggtgcttcg   180
aaggatcttt tcagcatttt aggttgccca gccggtttga agtaagga gaaaggagat   240
catggtagaa ttgcccatca tctggggctc gacccaaaaa caactatcaa ggaaatcata   300
gattatttgc tggagtgtaa ggagaaggaa cctctccccc caatcactgt tcctgtgtca   360
tctgcacctt gtaaaacaca tatactttct gaagaaaaaa tacatctaca aagcctgcca   420
acaccatatc tacatgtttc agacggtggc aagtacttac aaacgtacgg aatgtggatt   480
cttcaaactc cagataaaaa atggactaat tggtcaattg ctagaggtat ggttgtagat   540
gacaagcata tcactggtct ggtaattgtt ccacaacata ttagacaaat tgctgactct   600
tgggcagcaa ttggaaaagc aaatgaaatt cctttcgcgt tatgttttgg cgttccccca   660
gcagctattt tagttagttc catgccaatt cctgaaggtg tttctgaatc ggattatgtt   720
ggcgcaatct gggtgagtc ggttccagta gtaaatgtg agaccaacga tttaatggtt   780
cctgcaacga gtgagatggt atttgagggt actttgtcct taacagatac acatctggaa   840
ggcccatttg gtgagatgca tggatatgtt ttcaaaagcc aaggtcatcc ttgtccattg   900
```

```
tacactgtca aggctatgag ttacagagac aatgctattc tacctgtttc gaacccggt      960 ctttgtacgg atgagacaca taccttgatt ggttcactag tggctactga ggccaaggag    1020
ctggctattg aatctggctt gccaattctg gatgccttta tgccttatga ggctcaggct    1080
ctttggctta tcttaaaggt ggatttgaaa gggctgcaag cattgaagac aacgcctgaa    1140
gaattttgta agaaggtagg tgatatttac tttaggacaa agttggtttt tatagtccat    1200
gaaataattt tggtggcaga tgatatcgac atatttaact tcaaagaagt catctgggcc    1260
tacgttacaa gacatacacc tgttgcagat cagatggctt ttgatgatgt cacttctttt    1320
cctttggctc cctttgtttc gcagtcatcc agaagtaaga ctatgaaagg tggaaagtgc    1380
gttactaatt gcatatttag acagcaatat gagcgcagtt ttgactacat aacttgtaat    1440
tttgaaaagg gatatccaaa aggattagtt gacaaagtaa atgaaaattg gaaaggtac    1500 ggatataaat aa                                                        1512

<210> SEQ ID NO 30
<211> LENGTH: 503
<212> TYPE: PRT
<213> ORGANISM: Artificial Sequence
<220> FEATURE:
<223> OTHER INFORMATION: Synthetic

<400> SEQUENCE: 30

Met Arg Lys Leu Asn Pro Ala Leu Glu Phe Arg Asp Phe Ile Gln Val
1               5                   10                  15

Leu Lys Asp Glu Asp Leu Ile Glu Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ala Pro Cys Lys Thr His Ile
        115                 120                 125

Leu Ser Glu Glu Lys Ile His Leu Gln Ser Leu Pro Thr Pro Tyr Leu
    130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Val Pro Gln
            180                 185                 190

His Ile Arg Gln Ile Ala Asp Ser Trp Ala Ala Ile Gly Lys Ala Asn
        195                 200                 205

Glu Ile Pro Phe Ala Leu Cys Phe Gly Val Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Val Lys Cys Glu Thr Asn
```

```
                    245                 250                 255
Asp Leu Met Val Pro Ala Thr Ser Glu Met Val Phe Glu Gly Thr Leu
                260                 265                 270

Ser Leu Thr Asp Thr His Leu Glu Gly Pro Phe Gly Glu Met His Gly
            275                 280                 285

Tyr Val Phe Lys Ser Gln Gly His Pro Cys Pro Leu Tyr Thr Val Lys
        290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
        355                 360                 365

Leu Lys Gly Leu Gln Ala Leu Lys Thr Thr Pro Glu Glu Phe Cys Lys
        370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
        435                 440                 445

Ser Ser Arg Ser Lys Thr Met Lys Gly Gly Lys Cys Val Thr Asn Cys
        450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
                500

<210> SEQ ID NO 31
<211> LENGTH: 1512
<212> TYPE: DNA
<213> ORGANISM: Artificial Sequence
<220> FEATURE:
<223> OTHER INFORMATION: Synthetic

<400> SEQUENCE: 31
atgaggaagc taaatccagc tttagaattt agagacttta tccaggtctt aaaagatgaa      60
gatgacttaa tcgaaattac cgaagagatt gatccaaatc tcgaagtagg tgcaattatg     120
aggaaggcct atgaatccca cttaccagcc ccgttattta aaatctcaa aggtgcttcg      180 aaggatcttt tcagcatttt aggttgccca gccggtttga agtaagga gaaggagat        240 catggtagaa ttgcccatca tctggggctc gacccaaaaa caactatcaa ggaaatcata    300
gattatttgc tggagtgtaa ggagaaggaa cctctccccc caatcactgt tcctgtgtca     360
tctgcacctt gtaaaacaca tatactttct gaagaaaaaa tacatctaca aagcctgcca     420
acaccatatc tacatgtttc agacggtggc aagtacttac aaacgtacgg aatgtggatt    480
cttcaaactc cagataaaaa atggactaat tggtcaattg ctagaggtat ggttgtagat    540
gacaagcata tcactggtct ggtaatttcg ccacaacata ttagacaaat tgctgactct    600
```

```
tgggcagcaa ttggaaaagc aaatgaaatt cctttcgcgt tatgttttgg cgttccccca    660
gcagctattt tagttagttc catgccaatt cctgaaggtg tttctgaatc ggattatgtt    720
ggcgcaatct tgggtgagtc ggttccagta gtaaatgtg agaccaacga tttaatggtt    780
cctgcaacga gtgagatggt atttgagggt actttgtcct taacagatac acatctggaa    840
ggcccatttg gtgagatgca tggatatgtt ttcaaaagcc aaggtcatcc ttgtccattg    900
tacactgtca aggctatgag ttacagagac aatgctattc tacctgtttc gaaccccggt    960
ctttgtacgg atgagacaca taccttgatt ggttcactag tggctactga ggccaaggag    1020
ctggctattg aatctggctt gccaattctg gatgccttta tgccttatga ggctcaggct    1080
ctttggctta tcttaaaggt ggatttgaaa gggctgcaag cattgaagac aacgcctgaa    1140
gaattttgta agaaggtagg tgatatttac tttaggacaa agttggtttt atagtccat     1200 gaaataattt tggtggcaga tgatatcgac atatttaact tcaaagaagt catctgggcc    1260
tacgttacaa gacatacacc tgttgcagat cagatggctt ttgatgatgt cacttctttt    1320
cctttggctc cctttgtttc gcagtcatcc agaagtaaga ctatgaaagg tggaaagtgc    1380
gttactaatt gcatatttag acagcaatat gagcgcagtt ttgactacat aacttgtaat    1440
tttgaaaagg gatatccaaa aggattagtt gacaaagtaa atgaaaattg gaaaaggtac    1500
ggatataaat aa                                                        1512
```

<210> SEQ ID NO 32
<211> LENGTH: 503
<212> TYPE: PRT
<213> ORGANISM: Artificial Sequence
<220> FEATURE:
<223> OTHER INFORMATION: Synthetic

<400> SEQUENCE: 32

```
Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
        115                 120                 125

Leu Ser Glu Glu Lys Ile His Leu Gln Ser Leu Pro Thr Pro Tyr Leu
    130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Ser Pro Gln
            180                 185                 190
```

His Ile Arg Gln Ile Ala Asp Ser Trp Ala Ala Ile Gly Lys Ala Asn
            195                 200                 205

Glu Ile Pro Phe Ala Leu Cys Phe Gly Val Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Lys Cys Glu Thr Asn
                245                 250                 255

Asp Leu Met Val Pro Ala Thr Ser Glu Met Val Phe Glu Gly Thr Leu
                260                 265                 270

Ser Leu Thr Asp Thr His Leu Glu Gly Pro Phe Gly Glu Met His Gly
            275                 280                 285

Tyr Val Phe Lys Ser Gln Gly His Pro Cys Pro Leu Tyr Thr Val Lys
    290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
                340                 345                 350

Phe Met Pro Tyr Glu Ala Gln Ala Leu Trp Leu Ile Leu Lys Val Asp
            355                 360                 365

Leu Lys Gly Leu Gln Ala Leu Lys Thr Thr Pro Glu Glu Phe Cys Lys
    370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
    435                 440                 445

Ser Ser Arg Ser Lys Thr Met Lys Gly Gly Lys Cys Val Thr Asn Cys
450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500

<210> SEQ ID NO 33
<211> LENGTH: 1512
<212> TYPE: DNA
<213> ORGANISM: Artificial Sequence
<220> FEATURE:
<223> OTHER INFORMATION: Synthetic

<400> SEQUENCE: 33
atgaggaagc taaatccagc tttagaattt agagacttta tccaggtctt aaaagatgaa      60
gatgacttaa tcgaaattac cgaagagatt gatccaaatc tcgaagtagg tgcaattatg     120
aggaaggcct atgaatccca cttaccagcc ccgttattta aaaatctcaa aggtgcttcg     180
aaggatcttt tcagcatttt aggttgccca gccggtttga gaagtaagga gaaggagat      240 catggtagaa ttgcccatca tctgggggctc gacccaaaaa caactatcaa ggaaatcata     300

```
gattatttgc tggagtgtaa ggagaaggaa cctctccccc caatcactgt tcctgtgtca      360
tctgcacctt gtaaaacaca tatactttct gaagaaaaaa tacatctaca aagcctgcca      420
acaccatatc tacatgtttc agacggtggc aagtacttac aaacgtacgg aatgtggatt      480
cttcaaactc cagataaaaa atggactaat tggtcaattg ctagaggtat ggttgtagat      540
gacaagcata tcactggtct ggtaattaat ccacaacata ttagacaaat tgctgactct      600
tgggcagcaa ttgaaaagc aaatgaaatt cctttcgcgt tatgttttgg cgttccccca       660
gcagctattt tagttagttc catgccaatt cctgaaggtg tttctgaatc ggattatgtt      720
ggcgcaatct gggtgagtc ggttccagta gtaaaatgtg agaccaacga tttaatggtt       780
cctgcaacga gtgagatggt atttgagggt actttgtcct aacagatac acatctggaa       840 ggcccatttg gtgagatgca tggatatgtt ttcaaaagcc aaggtcatcc ttgtccattg      900
tacactgtca aggctatgag ttacagagac aatgctattc tacctgtttc gaaccccggt      960
ctttgtacgg atgagacaca taccttgatt ggttcactag tggctactga ggccaaggag     1020
ctggctattg aatctggctt gccaattctg gatgccttta tgccttatga ggctcaggct     1080
ctttggctta tcttaaaggt ggatttgaaa gggctgcaag cattgaagac aacgcctgaa     1140
gaattttgta agaaggtagg tgatatttac tttaggacaa aagttggttt tatagtccat     1200
gaaataattt tggtggcaga tgatatcgac atatttaact tcaaagaagt catctgggcc     1260
tacgttacaa gacatacacc tgttgcagat cagatggctt ttgatgatgt cacttctttt     1320
cctttggctc cctttgtttc gcagtcatcc agaagtaaga ctatgaaagg tggaaagtgc     1380
gttactaatt gcatatttag acagcaatat gagcgcagtt ttgactacat aacttgtaat     1440
tttgaaaagg gatatccaaa aggattagtt gacaaagtaa atgaaaattg gaaaaggtac     1500
ggatataaat aa                                                         1512
```

<210> SEQ ID NO 34
<211> LENGTH: 503
<212> TYPE: PRT
<213> ORGANISM: Artificial Sequence
<220> FEATURE:
<223> OTHER INFORMATION: Synthetic

<400> SEQUENCE: 34

```
Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
        115                 120                 125

Leu Ser Glu Glu Lys Ile His Leu Gln Ser Leu Pro Thr Pro Tyr Leu
    130                 135                 140
```

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
            165                 170                 175

Met Val Val Asp Asp Lys His Ile Thr Gly Leu Val Ile Asn Pro Gln
        180                 185                 190

His Ile Arg Gln Ile Ala Asp Ser Trp Ala Ala Ile Gly Lys Ala Asn
    195                 200                 205

Glu Ile Pro Phe Ala Leu Cys Phe Gly Val Pro Ala Ala Ile Leu
210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Lys Cys Glu Thr Asn
            245                 250                 255

Asp Leu Met Val Pro Ala Thr Ser Glu Met Val Phe Glu Gly Thr Leu
        260                 265                 270

Ser Leu Thr Asp Thr His Leu Glu Gly Pro Phe Gly Glu Met His Gly
    275                 280                 285

Tyr Val Phe Lys Ser Gln Gly His Pro Cys Pro Leu Tyr Thr Val Lys
290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
            325                 330                 335

Glu Ala Lys Glu Leu Ala Ile Glu Ser Gly Leu Pro Ile Leu Asp Ala
        340                 345                 350

Phe Met Pro Tyr Glu Ala Gln Ala Leu Trp Leu Ile Leu Lys Val Asp
    355                 360                 365

Leu Lys Gly Leu Gln Ala Leu Lys Thr Thr Pro Glu Glu Phe Cys Lys
370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Phe Asn Phe Lys Glu
            405                 410                 415

Val Ile Trp Ala Tyr Val Thr Arg His Thr Pro Val Ala Asp Gln Met
        420                 425                 430

Ala Phe Asp Asp Val Thr Ser Phe Pro Leu Ala Pro Phe Val Ser Gln
    435                 440                 445

Ser Ser Arg Ser Lys Thr Met Lys Gly Gly Lys Cys Val Thr Asn Cys
450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
            485                 490                 495

Trp Lys Arg Tyr Gly Tyr Lys
        500

<210> SEQ ID NO 35
<211> LENGTH: 1512
<212> TYPE: DNA
<213> ORGANISM: Artificial Sequence
<220> FEATURE:
<223> OTHER INFORMATION: Synthetic

<400> SEQUENCE: 35

```
atgaggaagc taaatccagc tttagaattt agagacttta tccaggtctt aaaagatgaa      60
gatgacttaa tcgaaattac cgaagagatt gatccaaatc tcgaagtagg tgcaattatg     120
aggaaggcct atgaatccca cttaccagcc ccgttattta aaaatctcaa aggtgcttcg     180
aaggatcttt tcagcatttt aggttgccca gccggtttga agtaagga gaaaggagat       240
catggtagaa ttgcccatca tctgggctc gacccaaaaa caactatcaa ggaaatcata     300
gattatttgc tggagtgtaa ggagaaggaa cctctccccc caatcactgt tcctgtgtca     360
tctgcacctt gtaaaacaca tatactttct gaagaaaaaa tacatctaca aagcctgcca     420
acaccatatc tacatgtttc agacggtggc aagtacttac aaacgtacgg aatgtggatt     480
cttcaaactc cagataaaaa atggactaat tggtcaattg ctattggtat ggttgtagat     540
gacaagcata tcactggtct ggtaattaaa ccacaacata ttagacaaat tgctgactct     600
tgggcagcaa ttggaaaagc aaatgaaatt cctttcgcgt tatgttttgg cgttccccca     660
gcagctattt tagttagttc catgccaatt cctgaaggtg tttctgaatc ggattatgtt     720
ggcgcaatct gggtgagtc ggttccagta gtaaaatgtg agaccaacga tttaatggtt      780
cctgcaacga gtgagatggt atttgagggt actttgtcct taacagatac acatctggaa     840
ggcccatttg gtgagatgca tggatatgtt ttcaaaagcc aaggtcatcc ttgtccattg     900
tacactgtca aggctatgag ttacagagac aatgctattc tacctgtttc gaaccccggt     960
ctttgtacgg atgagacaca taccttgatt ggttcactag tggctactga ggccaaggag    1020
ctggctattg aatctggctt gccaattctg gatgccttta tgccttatga ggctcaggct    1080
ctttggctta tcttaaaggt ggatttgaaa gggctgcaag cattgaagac aacgcctgaa    1140
gaattttgta agaaggtagg tgatatttac tttaggacaa agttggtttt atagtccat     1200
gaaataattt tggtggcaga tgatatcgac atatttaact tcaaagaagt catctgggcc    1260
tacgttacaa gacatacacc tgttgcagat cagatggctt ttgatgatgt cacttctttt    1320
cctttggctc cctttgtttc gcagtcatcc agaagtaaga ctatgaaagg tggaaagtgc    1380
gttactaatt gcatatttag acagcaatat gagcgcagtt ttgactacat aacttgtaat    1440
tttgaaaagg gatatccaaa aggattagtt gacaagtaa atgaaaattg gaaaaggtac    1500
ggatataaat aa                                                       1512
```

<210> SEQ ID NO 36
<211> LENGTH: 503
<212> TYPE: PRT
<213> ORGANISM: Artificial Sequence
<220> FEATURE:
<223> OTHER INFORMATION: Synthetic

<400> SEQUENCE: 36

```
Met Arg Lys Leu Asn Pro Ala Leu Glu Phe Arg Asp Phe Ile Gln Val
1               5                   10                  15

Leu Lys Asp Glu Asp Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
```

```
                85                  90                  95
Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
            115                 120                 125

Leu Ser Glu Glu Lys Ile His Leu Gln Ser Leu Pro Thr Pro Tyr Leu
130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Ile Gly
            165                 170                 175

Met Val Val Asp Asp Lys His Ile Thr Gly Leu Val Ile Lys Pro Gln
            180                 185                 190

His Ile Arg Gln Ile Ala Asp Ser Trp Ala Ala Ile Gly Lys Ala Asn
            195                 200                 205

Glu Ile Pro Phe Ala Leu Cys Phe Gly Val Pro Pro Ala Ala Ile Leu
210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Lys Cys Glu Thr Asn
            245                 250                 255

Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
            275                 280                 285

Tyr Val Phe Lys Ser Gln Gly His Pro Cys Pro Leu Tyr Thr Val Lys
            290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
            325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
            355                 360                 365

Leu Lys Gly Leu Gln Ala Leu Lys Thr Thr Pro Glu Glu Phe Cys Lys
            370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
            405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
            435                 440                 445

Ser Ser Arg Ser Lys Thr Met Lys Gly Gly Lys Cys Val Thr Asn Cys
450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
            485                 490                 495

Trp Lys Arg Tyr Gly Tyr Lys
            500
```

<210> SEQ ID NO 37
<211> LENGTH: 1512
<212> TYPE: DNA
<213> ORGANISM: Artificial Sequence
<220> FEATURE:
<223> OTHER INFORMATION: Synthetic

<400> SEQUENCE: 37

```
atgaggaagc taaatccagc tttagaattt agagacttta tccaggtctt aaaagatgaa      60
gatgacttaa tcgaaattac cgaagagatt gatccaaatc tcgaagtagg tgcaattatg     120
aggaaggcct atgaatccca cttaccagcc ccgttattta aaaatctcaa aggtgcttcg     180
aaggatcttt tcagcatttt aggttgccca gccggtttga agtaagga gaaaggagat       240
catggtagaa ttgcccatca tctggggctc gacccaaaaa caactatcaa ggaaatcata     300
gattatttgc tggagtgtaa ggagaaggaa cctctccccc aatcactgt tcctgtgtca      360
tctgcaccctt gtaaaacaca tatctttct gaagaaaaaa tacatctaca aagcctgcca    420
acaccatatc tacatgtttc agacggtggc aagtacttac aaacgtacgg aatgtggatt     480
cttcaaactc cagataaaaa atggactaat tggtcaattg ctagaggtat ggttgtagat     540
gacaagcata tcactggtct ggtaattaaa ccacaaccta ttagacaaat tgctgactct     600
tgggcagcaa ttggaaaagc aaatgaaatt ccttcgcgt tatgttttgg cgttccccca     660
gcagctattt tagttagttc catgccaatt cctgaaggtg tttctgaatc ggattatgtt     720
ggcgcaatct gggtgagtc ggttccagta gtaaaatgtg agaccaacga tttaatggtt     780
cctgcaacga gtgagatggt atttgagggt actttgtcct aacagatac acatctggaa     840
ggcccatttg gtgagatgca tggatatgtt ttcaaaagcc aaggtcatcc ttgtccattg     900
tacactgtca aggctatgag ttacagagac aatgctattc tacctgtttc gaaccccggt     960
ctttgtacgg atgagacaca taccttgatt ggttcactag tggctactga ggccaaggag    1020
ctggctattg aatctggctt gccaattctg gatgcctttta tgccttatga ggctcaggct    1080
ctttggctta tcttaaaggt ggatttgaaa gggctgcaag cattgaagac aacgcctgaa    1140
gaattttgta agaaggtagg tgatatttac tttaggacaa aagttggttt tatagtccat    1200
gaaataattt tggtggcaga tgatatcgac atatttaact tcaaagaagt catctgggcc    1260
tacgttacaa gacatacacc tgttgcagat cagatggctt ttgatgatgt cacttctttt    1320
cctttggctc cctttgtttc gcagtcatcc agaagtaaga ctatgaaagg tggaaagtgc    1380
gttactaatt gcatatttag acagcaatat gagcgcagtt ttgactacat aacttgtaat    1440
tttgaaaagg gatatccaaa aggattagtt gacaaagtaa atgaaaattg gaaaaggtac    1500
ggatataaat aa                                                        1512
```

<210> SEQ ID NO 38
<211> LENGTH: 503
<212> TYPE: PRT
<213> ORGANISM: Artificial Sequence
<220> FEATURE:
<223> OTHER INFORMATION: Synthetic

<400> SEQUENCE: 38

```
Met Arg Lys Leu Asn Pro Ala Leu Glu Phe Arg Asp Phe Ile Gln Val
1               5                   10                  15
Leu Lys Asp Glu Asp Asp Leu Ile Glu Ile Thr Glu Glu Ile Asp Pro
            20                  25                  30
```

-continued

```
Asn Leu Glu Val Gly Ala Ile Met Arg Lys Ala Tyr Glu Ser His Leu
             35                  40                  45

Pro Ala Pro Leu Phe Lys Asn Leu Lys Gly Ala Ser Lys Asp Leu Phe
 50                  55                  60

Ser Ile Leu Gly Cys Pro Ala Gly Leu Arg Ser Lys Glu Lys Gly Asp
 65                  70                  75                  80

His Gly Arg Ile Ala His His Leu Gly Leu Asp Pro Lys Thr Thr Ile
                 85                  90                  95

Lys Glu Ile Ile Asp Tyr Leu Leu Glu Cys Lys Glu Lys Glu Pro Leu
                100                 105                 110

Pro Pro Ile Thr Val Pro Val Ser Ser Ala Pro Cys Lys Thr His Ile
            115                 120                 125

Leu Ser Glu Glu Lys Ile His Leu Gln Ser Leu Pro Thr Pro Tyr Leu
130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Asp Asp Lys His Ile Thr Gly Leu Val Ile Lys Pro Gln
            180                 185                 190

Pro Ile Arg Gln Ile Ala Asp Ser Trp Ala Ala Ile Gly Lys Ala Asn
            195                 200                 205

Glu Ile Pro Phe Ala Leu Cys Phe Gly Val Pro Pro Ala Ala Ile Leu
210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Val Lys Cys Glu Thr Asn
                245                 250                 255

Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
            275                 280                 285

Tyr Val Phe Lys Ser Gln Gly His Pro Cys Pro Leu Tyr Thr Val Lys
290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
            355                 360                 365

Leu Lys Gly Leu Gln Ala Leu Lys Thr Thr Pro Glu Glu Phe Cys Lys
370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
            435                 440                 445

Ser Ser Arg Ser Lys Thr Met Lys Gly Gly Lys Cys Val Thr Asn Cys
```

```
                450                 455                 460
Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500

<210> SEQ ID NO 39
<211> LENGTH: 4
<212> TYPE: PRT
<213> ORGANISM: Artificial Sequence
<220> FEATURE:
<223> OTHER INFORMATION: Synthetic

<400> SEQUENCE: 39

Gly Gly Ser Gly
1

<210> SEQ ID NO 40
<211> LENGTH: 6
<212> TYPE: PRT
<213> ORGANISM: Artificial Sequence
<220> FEATURE:
<223> OTHER INFORMATION: Synthetic

<400> SEQUENCE: 40

Gly Ser Gly Ser Gly Ser
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic

<400> SEQUENCE: 41

Gly Gly Ser Gly Gly Gly Ser Gly
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic

<400> SEQUENCE: 42

Ser Gly Gly Ser Gly Gly Ser Gly Gly
1               5

<210> SEQ ID NO 43
<211> LENGTH: 12
<212> TYPE: PRT
<213> ORGANISM: Artificial Sequence
<220> FEATURE:
<223> OTHER INFORMATION: Synthetic

<400> SEQUENCE: 43

Gly Gly Ser Gly Gly Gly Ser Gly Gly Gly Ser Gly
1               5                   10

<210> SEQ ID NO 44
<211> LENGTH: 15
```

```
<212> TYPE: PRT
<213> ORGANISM: Artificial Sequence
<220> FEATURE:
<223> OTHER INFORMATION: Synthetic

<400> SEQUENCE: 44

Gly Gly Gly Gly Ser Gly Gly Gly Gly Ser Gly Gly Gly Gly Ser
1               5                   10                  15
```

ENZYMES AND METHODS FOR STYRENE SYNTHESIS

CROSS-REFERENCE TO RELATED APPLICATIONS

This Application is a divisional of U.S. application Ser. No. 14/409,600, entitled "ENZYMES AND METHODS FOR STYRENE SYNTHESIS" filed on Dec. 19, 2014, which is a national stage filing under U.S.C. § 371 of PCT International Application No. PCT/US2013/047098 with an international filing date of Jun. 21, 2013, which claims priority under 35 U.S.C. § 119(e) to U.S. Provisional Application Ser. No. 61/663,500, entitled "ENZYMATIC SYSTEM FOR MONOMER SYNTHESIS" filed on Jun. 22, 2012. The entire contents of each of these applications are incorporated herein by reference in their entirety.

INCORPORATION OF SEQUENCE LISTING

A computer readable form of the Sequence Listing named "C149770018US02-SEQ-AM.txt", which is 151,674 bytes in size (as measured in MICROSOFT WINDOWS® EXPLORER), is provided herein and is herein incorporated by reference. This Sequence Listing consists of SEQ ID Nos: 1-44.

BACKGROUND

The subject technology generally relates to enzymes and methods for biosynthesis of styrene.

Styrene (vinyl benzene) is an organic compound with a chemical formula of $C_8H_8$. This cyclic hydrocarbon is a colorless, oily liquid that evaporates easily and has a sweet rubber-like smell. At higher concentrations, styrene confers a less pleasant odor. Styrene is named after the *styrax* trees (*Styrax platanifolius*) from which sap (a type of benzoin resin) can be extracted. Low levels of styrene occur naturally in several plant species. A variety of foods such as fruits, vegetables, nuts, beverages, and meats also contain styrene.

Industrially, styrene is the precursor to polystyrene and several copolymers. The presence of the vinyl group allows styrene to polymerize. Approximately 15 billion pounds are produced annually. The production of styrene in the United States increased dramatically during the 1940s, when it was popularized as a feedstock for synthetic rubber. Today, commercially significant products include polystyrene, acrylonitrile butadiene styrene (ABS), styrene-butadiene (SBR) rubber, styrene-butadiene latex, SIS (styrene-isoprene-styrene), S-EB-S (styrene-ethylene/butylene-styrene), styrene-divinylbenzene (S-DVB), styrene-acrylonitrile resin (SAN) and unsaturated polyesters. These materials are used in rubber, plastic, insulation, fiberglass, pipes, automobile and boat parts, food containers, and carpet backing.

Styrene is produced in industrial quantities mostly from ethylbenzene, which is in turn prepared on a large scale by alkylation of benzene with ethylene. It is one of the most important petrochemical products. There are several methods to produce styrene. Dehydrogenation of ethylbenzene is the most common way of production. Ethylbenzene is mixed in the gas phase with 10-15 times its volume in high-temperature steam, and passed over a solid catalyst bed. Most ethylbenzene dehydrogenation catalysts are based on iron(III) oxide, promoted by several percent potassium oxide or potassium carbonate. Steam serves several roles in this reaction. It is the source of heat for powering the endothermic reaction, and it removes coke that tends to form on the iron oxide catalyst through the water gas shift reaction. The potassium promoter enhances this decoking reaction. The steam also dilutes the reactant and products, shifting the position of chemical equilibrium towards products. A typical styrene plant consists of two or three reactors in series, which operate under vacuum to enhance the conversion and selectivity. Typical per-pass conversions are ca. 65% for two reactors and 70-75% for three reactors. Selectivity to styrene is 93-97%. The main byproducts are benzene and toluene. Because styrene and ethylbenzene have similar boiling points (145 and 136° C., respectively), their separation requires tall distillation towers and high return/reflux ratios. At its distillation temperatures, styrene tends to polymerize. To minimize this problem, early styrene plants added elemental sulfur to inhibit the polymerization. During the 1970s, new free radical inhibitors consisting of nitrated phenol-based retarders were developed. More recently, a number of additives have been developed that exhibit superior inhibition against polymerization.

Since styrene is an essential petrochemical used in many chemical products, alternative production methods, especially ones that do not require fossil fuels as feed stock, are urgently needed. Hence, despite the availability of methods for producing styrene, there is a continuing need for new methods for producing styrene monomers that are efficient and less expensive.

SUMMARY

The subject technology generally relates to the biosynthesis of styrene. Some embodiments of the subject technology are based, in part, on the recognition that phenylalanine can be converted to styrene by a two-step pathway of deamination and decarboxylation, with trans-cinnamic acid (tCA) as the intermediate. Two types of enzymes are directly involved in this process, phenylalanine ammonia lyase (PAL), which converts phenylalanine to tCA, and cinnamic acid decarboxylase, which coverts tCA to styrene. Host cells expressing these two types of enzymes can be cultured in a bioreactor to produce styrene from renewable substrates such as glucose.

In one aspect, the subject technology relates to a fusion protein comprising: (a) a first domain that comprises a phenylalanine ammonia lyase, and (b) a second domain that comprises a cinnamic acid decarboxylase.

In certain embodiments, the phenylalanine ammonia lyase is derived from an organism selected from the group consisting of: an *Arabidopsis*, an *Anabaena*, a *Nostoc*, and a *Saccharomyces*. In an exemplary embodiment, the phenylalanine ammonia lyase comprises an amino acid sequence selected from the group consisting of: SEQ ID NO:2, SEQ ID NO:4, SEQ ID NO:6, and a functional fragment or variant thereof.

In certain embodiments, the cinnamic acid decarboxylase is derived from an organism selected from the group consisting of: an *Arabidopsis*, an *Anabaena*, a *Nostoc*, and a *Saccharomyces*. In an exemplary embodiment, the cinnamic acid decarboxylase comprises an amino acid sequence selected from the group consisting of: SEQ ID NO:8; SEQ ID NO:10; SEQ ID NO:16; SEQ ID NO:18; SEQ ID NO:20; SEQ ID NO:22; SEQ ID NO:24; SEQ ID NO:26; SEQ ID NO:28; SEQ ID NO:30; SEQ ID NO:32; SEQ ID NO:34; SEQ ID NO:36; SEQ ID NO:38; and a functional fragment or variant thereof. For example, the cinnamic acid decarboxylase may comprise an amino acid sequence selected from the group consisting of: SEQ ID NO:8; SEQ ID NO:10; SEQ ID NO:16; SEQ ID NO:18; SEQ ID NO:20;

SEQ ID NO:22; SEQ ID NO:24; SEQ ID NO:26; SEQ ID NO:28; SEQ ID NO:30; SEQ ID NO:32; SEQ ID NO:34; SEQ ID NO:36; and SEQ ID NO:38.

A functional variant of a cinnamic acid decarboxylase may comprise an amino acid sequence that is about 85%, about 90%, about 95%, about 96%, about 97%, about 98%, about 99%, or even 100% identical to any one of SEQ ID NO:8; SEQ ID NO:10; SEQ ID NO:16; SEQ ID NO:18; SEQ ID NO:20; SEQ ID NO:22; SEQ ID NO:24; SEQ ID NO:26; SEQ ID NO:28; SEQ ID NO:30; SEQ ID NO:32; SEQ ID NO:34; SEQ ID NO:36; and SEQ ID NO:38. Alternatively, or in addition, a functional variant of a cinnamic acid decarboxylase can comprise: I at a position corresponding to residue 173 of SEQ ID NO: 8, A at a position corresponding to residue 174 of SEQ ID NO: 8, R at a position corresponding to residue 175 of SEQ ID NO: 8, V at a position corresponding to residue 188 of SEQ ID NO: 8, I at a position corresponding to residue 189 of SEQ ID NO: 8, K at a position corresponding to residue 190 of SEQ ID NO: 8, I at a position corresponding to residue 194 of SEQ ID NO: 8, E at a position corresponding to residue 280 of SEQ ID NO: 8, M at a position corresponding to residue 286 of SEQ ID NO: 8, F at a position corresponding to residue 291 of SEQ ID NO: 8, and F at a position corresponding to residue 440 of SEQ ID NO: 8.

In certain embodiments, the cinnamic acid decarboxylase can comprise a mutant cinnamic acid decarboxylase that comprises a mutation at an amino acid residue position corresponding to one of the following: 155, 156, 159, 162, 163, 164, 172, 173, 174, 175, 187, 188, 189, 190, 191, 192, 193, 194, 195, 196, 226, 227, 280, 285, 286, 287, 291, 326, 331, 360, 361, 395, 396, 398, 440, 441 of SEQ ID NO:8, or a combination thereof. For example, the mutant cinnamic acid decarboxylase can comprise a mutation at an amino acid residue position corresponding to one of the following positions: 175, 190, 193 of SEQ ID NO:8, and a combination thereof.

In certain embodiments, the cinnamic acid decarboxylase can comprise a mutant cinnamic acid decarboxylase that comprises a deletion, a substitution, or an addition of an amino acid residue at one of the positions of SEQ ID NO:8 selected from: 155, 156, 159, 162, 163, 164, 172, 173, 174, 175, 187, 188, 189, 190, 191, 192, 193, 194, 195, 196, 226, 227, 280, 285, 286, 287, 291, 326, 331, 360, 361, 395, 396, 398, 440, 441, and a combination thereof. For example, an amino acid residue at one the of the following positions: 155, 156, 159, 162, 163, 164, 172, 173, 174, 175, 187, 188, 189, 190, 191, 192, 193, 194, 195, 196, 226, 227, 280, 285, 286, 287, 291, 326, 331, 360, 361, 395, 396, 398, 440, or 441 of SEQ ID NO:8 can be substituted with another amino acid residue. In another example, the mutant cinnamic acid decarboxylase comprises a deletion, a substitution, or an addition of an amino acid residue at one of the positions of SEQ ID NO:8: 175, 190, 193, and a combination thereof.

In one embodiment, the fusion protein of the subject technology further comprises a linker covalently linking the first domain and the second domain. The linker of the fusion protein described herein may be a peptide linker, e.g., a peptide linker comprising 2 to 15 amino acids. Peptide linkers can include those shown in Table 1, for example.

Also provided are nucleic acids encoding the fusion proteins described herein, a vector comprising the nucleic acid encoding the fusion protein, and host cells comprising the vector described herein.

In one aspect, the subject technology relates to a method for producing styrene comprising (a) contacting a host cell with a fermentable substrate (preferably carbon substrate or nitrogen substrate), the host cell comprises a fusion protein comprising: (i) a first domain that comprises a phenylalanine ammonia lyase, and (ii) a second domain that comprises a cinnamic acid decarboxylase; and (b) culturing the cell in a culture medium for a time sufficient to produce styrene. The method can further comprise harvesting styrene from the cell culture. Any one of the fusion proteins described herein can be used to produce styrene.

In one aspect, the subject technology relates to a cinnamic acid decarboxylase comprising (a) any one of SEQ ID NO:16; SEQ ID NO:18; SEQ ID NO:20; SEQ ID NO:22; SEQ ID NO:24; SEQ ID NO:26; SEQ ID NO:28; SEQ ID NO:30; SEQ ID NO:32; SEQ ID NO:34; SEQ ID NO:36; and SEQ ID NO:38; (b) an amino acid sequence that is about 85%, about 90%, about 95%, about 97%, about 98%, about 99%, or even 100% identical to any one of SEQ ID NO:16; SEQ ID NO:18; SEQ ID NO:20; SEQ ID NO:22; SEQ ID NO:24; SEQ ID NO:26; SEQ ID NO:28; SEQ ID NO:30; SEQ ID NO:32; SEQ ID NO:34; SEQ ID NO:36; and SEQ ID NO:38, with the proviso that said amino acid sequence is not SEQ ID NO: 8; or (c) a functional fragment of (a) or (b).

In certain embodiments, the cinnamic acid decarboxylase comprises: I at a position corresponding to residue 173 of SEQ ID NO: 8, A at a position corresponding to residue 174 of SEQ ID NO: 8, R at a position corresponding to residue 175 of SEQ ID NO: 8, V at a position corresponding to residue 188 of SEQ ID NO: 8, I at a position corresponding to residue 189 of SEQ ID NO: 8, K at a position corresponding to residue 190 of SEQ ID NO: 8, I at a position corresponding to residue 194 of SEQ ID NO: 8, E at a position corresponding to residue 280 of SEQ ID NO: 8, M at a position corresponding to residue 286 of SEQ ID NO: 8, F at a position corresponding to residue 291 of SEQ ID NO: 8, and F at a position corresponding to residue 440 of SEQ ID NO: 8.

In certain embodiments, the cinnamic acid decarboxylase comprises any one of SEQ ID NO:16; SEQ ID NO:18; SEQ ID NO:20; SEQ ID NO:22; SEQ ID NO:24; SEQ ID NO:26; SEQ ID NO:28; SEQ ID NO:30; SEQ ID NO:32; SEQ ID NO:34; SEQ ID NO:36; and SEQ ID NO:38.

The subject technology also relates to a mutant cinnamic acid decarboxylase comprising a mutation at an amino acid residue position corresponding to one of the following positions: 155, 156, 159, 162, 163, 164, 172, 173, 174, 175, 187, 188, 189, 190, 191, 192, 193, 194, 195, 196, 226, 227, 280, 285, 286, 287, 291, 326, 331, 360, 361, 395, 396, 398, 440, 441 of SEQ ID NO:8, and a combination thereof. For example, the mutant cinnamic acid decarboxylase can comprise a mutation at an amino acid residue position corresponding to one of the following positions: 175, 190, 193 of SEQ ID NO:8, and a combination thereof.

In certain embodiments, the mutant cinnamic acid decarboxylase comprises a deletion, a substitution, or an addition of an amino acid residue at one of the positions of SEQ ID NO:8: 155, 156, 159, 162, 163, 164, 172, 173, 174, 175, 187, 188, 189, 190, 191, 192, 193, 194, 195, 196, 226, 227, 280, 285, 286, 287, 291, 326, 331, 360, 361, 395, 396, 398, 440, 441, and a combination thereof. In certain embodiments, the mutation is a substitution.

In certain embodiments, the mutant cinnamic acid decarboxylase comprises a deletion, a substitution, or an addition of an amino acid residue at one of the positions of SEQ ID NO:8: 175, 190, 193, and a combination thereof.

Also provided are nucleic acids encoding the cinnamic acid decarboxylases described herein, host cells comprising the cinnamic acid decarboxylases described herein, and host cells comprising the nucleic acids described herein.

The subject technology also relates to a method for the production of styrene comprising: (a) contacting a host cell with a fermentable substrate (preferably carbon substrate or nitrogen substrate), the host cell comprising (i) a phenylalanine ammonia lyase as described herein; and (ii) a cinnamic acid decarboxylase as described herein; and (b) culturing the cell in a culture medium for a time sufficient to produce styrene.

The subject technology also relates to a host cell comprising: (a) a recombinantly expressed phenylalanine ammonia lyase as described herein; (b) a recombinantly expressed cinnamic acid decarboxylase as described herein; and (c) a recombinantly expressed membrane-bound transporter as described herein. The phenylalanine ammonia lyase and the cinnamic acid decarboxylase can be expressed as two separate proteins, or can be covalently linked by a linker as described herein.

In one embodiment, the membrane-bound transporter is an ATP-binding cassette transporter (ABC transporter). For example, the ABC transporter is a bacterial ABC transporter, such as one derived from *Pseudomonas putida*. Preferably, the ABC transporter is a solvent resistance efflux pump, such as the SrpABC pump derived from *Pseudomonas putida* S12.

The subject technology also provides a method for screening candidate proteins for mutated cinnamic acid decarboxylase activity, the method comprising: (a) providing a protein sample comprising a candidate protein, and a substrate selected from the group consisting of phenylalanine, trans-cinnamic acid, tyrosine, coumaric acid, and combinations thereof; (b) combining the protein sample and the substrate sample to form a mixture, and incubating the mixture under a condition that allows a mutated cinnamic acid decarboxylase to convert the substrate to a product selected from the group consisting of styrene, 4-hydroxystyrene, and combination thereof; and (c) exposing the mixture to a detection material that comprises a polymeric resin that absorbs the product vapor. In one embodiment, the mutated cinnamic acid decarboxylase is capable of converting trans-cinnamic acid to styrene, at a rate that is comparable to or higher than the wild type enzyme (e.g. FDC1). In another embodiment, the mutated cinnamic acid decarboxylase is capable of converting coumaric acid to 4-hydroxystyrene, at a rate that is comparable to higher than the wild type enzyme. In certain embodiments, the candidate protein comprises a fusion protein comprising a mutated cinnamic acid decarboxylase.

In one embodiment, the subject technology also relates to a method for screening candidate proteins for cinnamic acid decarboxylase activity, comprising: (a) providing a protein sample comprising the candidate protein, and a substrate sample comprising trans-cinnamic acid; (b) combining the protein sample and substrate sample to form a mixture, and incubating the mixture under a condition that allows a cinnamic acid decarboxylase to convert trans-cinnamic acid to styrene; and (c) exposing the mixture to a detection material that comprises a polymeric resin that absorbs styrene vapor.

In certain embodiments, the detection material further comprises a detectable marker that causes a color change in the presence of styrene. For example, the detectable marker can be 4-nitrobenzyl-pyridine. The detection material can be attached to a solid support. In certain embodiments, the polymeric resin comprises an aromatic functional group.

In certain embodiments, the change of color can be detected by spectrophotometry. For example, the change of color can be detected by measuring the absorbance of the sample at about 600 nm wavelength.

The screening method described herein can be used to simultaneously screen a plurality of candidate proteins.

The subject technology also relates to a method of isolating a recombinantly produced cinnamic acid decarboxylase, comprising (a) providing a bacterial host comprising a nucleic acid that encodes a cinnamic acid decarboxylase operably linked to a promoter sequence; (b) culturing the bacterial host in a culture medium to express the cinnamic acid decarboxylase in the host cell, therein the host cell is cultured at a temperature that is from about 10° C. to about 25° C.; and (c) isolating the cinnamic acid decarboxylase from the host cell, wherein the isolation is conducted in an anaerobic environment.

In certain embodiments, one or more buffer solutions used for isolating the cinnamic acid decarboxylase comprises a reducing agent, such as Tris(2-carboxyethyl) phosphine (TCEP), β-mercaptoethanol, and a combination thereof.

The subject technology also relates to a method of crystallizing a cinnamic acid decarboxylase, the method comprising: (a) providing a cinnamic acid decarboxylase solution at a concentration of from about 1 mg/ml to about 50 mg/ml; (b) mixing the cinnamic acid decarboxylase solution with a reservoir solution at a volume ratio of from about 1:10 to about 10:1; and (c) maintaining the mixture of the cinnamic acid decarboxylase solution and the reservoir solution at a temperature suitable for the formation of the cinnamic acid decarboxylase crystals.

The subject technology also relates to a crystal of cinnamic acid decarboxylase, wherein the cinnamic acid decarboxylase is in a complex with 3-hydroxyl cinnamic acid.

The subject technology also relates to a method for producing styrene, the method comprising: (a) contacting a host cell with a fermentable carbon substrate, the host cell comprising (i) a phenylalanine ammonia lyase; and (ii) a cinnamic acid decarboxylase; and (b) culturing the host cell in a culture medium for a time sufficient to produce styrene, wherein the vapor of the styrene product is absorbed by an absorbing material.

A method for simultaneously screening phenylalanine ammonia lyase and cinnamic acid decarboxylase activities, the method comprising: (a) providing a fusion protein comprising: (i) a first domain comprising a phenylalanine ammonia lyase, and (ii) a second domain comprising a cinnamic acid decarboxylase; (b) mixing the fusion protein with a substrate under a condition that allows the fusion protein to convert the substrate to a product; and (c) detecting the amount of the remaining substrate, or the amount of the product, or a combination thereof. In certain embodiments, the screening comprises detecting the loss of the substrate, or the amount of a product, such as trans-cinnami acid, styrene, and the downstream derivatives of styrene. For example, the screening can comprise detecting the amount of trans-cinnamic acid, or styrene, or a combination thereof.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 17. The other clauses can be presented in a similar manner.

1. A fusion protein comprising: (i) a first domain that comprises a phenylalanine ammonia lyase, and (ii) a second domain that comprises a cinnamic acid decarboxylase; and (iii) a linker that covalently links the first domain and the second domain.

2. The fusion protein of clause 1, wherein said phenylalanine ammonia lyase is derived from an organism selected from the group consisting of: an *Arabidopsis*, an *Anabaena*, a *Nostoc*, and a *Saccharomyces*.

3. The fusion protein of clause 1 or 2, wherein said phenylalanine ammonia lyase comprises an amino acid sequence selected from the group consisting of: SEQ ID NO:2, SEQ ID NO:4, SEQ ID NO:6, and a functional fragment or variant thereof.

4. The fusion protein of any one of clauses 1-3, wherein said cinnamic acid decarboxylase is derived from an organism selected from the group consisting of: an *Arabidopsis*, an *Anabaena*, a *Nostoc*, and a *Saccharomyces*.

5. The fusion protein of any one of clauses 1-4, wherein said cinnamic acid decarboxylase comprises an amino acid sequence selected from the group consisting of: SEQ ID NOs: 8, 10, 16, 18, 20, 22, 24, 26, 28, 30, 32, 34, 36, 38, and a functional fragment or variant thereof.

6. The fusion protein of clause 5, wherein said cinnamic acid decarboxylase comprises an amino acid sequence selected from the group consisting of: SEQ ID NOs: 8, 10, 16, 18, 20, 22, 24, 26, 28, 30, 32, 34, 36, and 38.

7. The fusion protein of clause 5, wherein said functional variant comprises an amino acid sequence that is about 85% identical to any one of SEQ ID NOs: 8, 10, 16, 18, 20, 22, 24, 26, 28, 30, 32, 34, 36, and 38.

8. The fusion protein of clause 5 or 7, wherein said functional variant comprises: I at a position corresponding to residue 173 of SEQ ID NO: 8, A at a position corresponding to residue 174 of SEQ ID NO: 8, R at a position corresponding to residue 175 of SEQ ID NO: 8, V at a position corresponding to residue 188 of SEQ ID NO: 8, T at a position corresponding to residue 189 of SEQ ID NO: 8, K at a position corresponding to residue 190 of SEQ ID NO: 8, I at a position corresponding to residue 194 of SEQ ID NO: 8, E at a position corresponding to residue 280 of SEQ ID NO: 8, M at a position corresponding to residue 286 of SEQ ID NO: 8, F at a position corresponding to residue 291 of SEQ ID NO: 8, and F at a position corresponding to residue 440 of SEQ ID NO: 8.

9. The fusion protein of any one of clauses 1-4, wherein said cinnamic acid decarboxylase is a mutant cinnamic acid decarboxylase that comprises a mutation at an amino acid residue position corresponding to one of the following: 155, 156, 159, 162, 163, 164, 172, 173, 174, 175, 187, 188, 189, 190, 191, 192, 193, 194, 195, 196, 226, 227, 285, 286, 287, 291, 326, 331, 360, 361, 395, 396, 398, 440, or 441 of SEQ ID NO: 8.

10. The fusion protein of any one of clauses 1-4, wherein said cinnamic acid decarboxylase is a mutant cinnamic acid decarboxylase that comprises a mutation at an amino acid residue position corresponding to one of the following positions: 175 or 190 of SEQ ID NO:8.

11. The fusion protein of any one of clauses 1-4, wherein said cinnamic acid decarboxylase is a mutant cinnamic acid decarboxylase that comprises a deletion, a substitution, or an addition of an amino acid residue at one of the positions of SEQ ID NO:8: 155, 156, 159, 162, 163, 164, 172, 173, 174, 175, 187, 188, 189, 190, 191, 192, 193, 194, 195, 196, 226, 227, 285, 286, 287, 291, 326, 331, 360, 361, 395, 396, 398, 440, or 441.

12. The fusion protein of any one of clauses 1-4, wherein said cinnamic acid decarboxylase is a mutant cinnamic acid decarboxylase that comprises a substitution of an amino acid residue at one of the positions of SEQ ID NO:8: 155, 156, 159, 162, 163, 164, 172, 173, 174, 175, 187, 188, 189, 190, 191, 192, 193, 194, 195, 196, 226, 227, 285, 286, 287, 291, 326, 331, 360, 361, 395, 396, 398, 440, or 441.

13. The fusion protein of any one of clauses 1-4, wherein said cinnamic acid decarboxylase is a mutant cinnamic acid decarboxylase that comprises a deletion, a substitution, or an addition of an amino acid residue at one of the positions of SEQ ID NO:8:175 or 190.

14. The fusion protein of any one of clauses 1-13, wherein said linker is a peptide linker comprising 2 to 15 amino acids.

15. The fusion protein of any one of clauses 1-14, wherein said linker is a peptide linker consisting essentially of glycine and serine.

16. The fusion protein of any one of clauses 1-15, wherein said linker comprises an amino acid sequence as set forth in any one of SEQ ID NOs. 39-44.

17. A nucleic acid encoding any one of the fusion protein of clauses 1-16.

18. A host cell comprising any one of the fusion protein of clauses 1-16.

19. A host cell comprising the nucleic acid of clause 17.

20. A method for the producing styrene comprising: (a) contacting a host cell with a fermentable carbon substrate, said host cell comprises a fusion protein comprising: (i) a first domain that comprises a phenylalanine ammonia lyase; (ii) a second domain that comprises a cinnamic acid decarboxylase; and (iii) a linker that covalently links the first domain and the second domain; (b) culturing said cell in a culture medium for a time sufficient to produce styrene.

21. The method of clause 20, further comprising harvesting styrene from said cell culture.

22. The method of clause 20 or 21, wherein said phenylalanine ammonia lyase is derived from an organism selected from the group consisting of: an *Arabidopsis*, an *Anabaena*, a *Nostoc*, and a *Saccharomyces*.

23. The method of any one of clauses 20-22, wherein said phenylalanine ammonia lyase comprises an amino acid sequence selected from the group consisting of: SEQ ID NO:2, SEQ ID NO:4, SEQ ID NO:6, and a functional fragment or variant thereof.

24. The method of any one of clauses 20-23, wherein said cinnamic acid decarboxylase is derived from an organism selected from the group consisting of: an *Arabidopsis*, an *Anabaena*, a *Nostoc*, and a *Saccharomyces*.

25. The method of any one of clauses 20-24, wherein said cinnamic acid decarboxylase comprises an amino acid sequence selected from the group consisting of: SEQ ID NOs: 8, 10, 16, 18, 20, 22, 24, 26, 28, 30, 32, 34, 36, 38, and a functional fragment or variant thereof.

26. The method of clause 25, wherein said cinnamic acid decarboxylase comprises an amino acid sequence selected from the group consisting of: SEQ ID NOs: 8, 10, 16, 18, 20, 22, 24, 26, 28, 30, 32, 34, 36, and 38.

27. The method of clause 25, wherein said functional variant comprises an amino acid sequence that is about 85% identical to any one of SEQ ID NOs: 8, 10, 16, 18, 20, 22, 24, 26, 28, 30, 32, 34, 36, and 38.

28. The method of clause 25 or 27, wherein said functional variant comprises: I at a position corresponding to residue 173 of SEQ ID NO: 8, A at a position corresponding to residue 174 of SEQ ID NO: 8, R at a position corresponding to residue 175 of SEQ ID NO: 8, V at a position corresponding to residue 188 of SEQ ID NO: 8, I at a position corresponding to residue 189 of SEQ ID NO: 8, K at a position corresponding to residue 190 of SEQ ID NO:

8, I at a position corresponding to residue 194 of SEQ ID NO: 8, E at a position corresponding to residue 280 of SEQ ID NO: 8, M at a position corresponding to residue 286 of SEQ ID NO: 8, F at a position corresponding to residue 291 of SEQ ID NO: 8, and F at a position corresponding to residue 440 of SEQ ID NO: 8.

29. The method of any one of clauses 20-24, wherein said cinnamic acid decarboxylase is a mutant cinnamic acid decarboxylase that comprises a mutation at an amino acid residue position corresponding to one of the following: 155, 156, 159, 162, 163, 164, 172, 173, 174, 175, 187, 188, 189, 190, 191, 192, 193, 194, 195, 196, 226, 227, 285, 286, 287, 291, 326, 331, 360, 361, 395, 396, 398, 440, or 441 of SEQ ID NO: 8.

30. The method of any one of clauses 20-24, wherein said cinnamic acid decarboxylase is a mutant cinnamic acid decarboxylase that comprises a mutation at an amino acid residue position corresponding to one of the following positions: 175 or 190 of SEQ ID NO: 8.

31. The method of any one of clauses 20-24, wherein said cinnamic acid decarboxylase is a mutant cinnamic acid decarboxylase that comprises a deletion, a substitution, or an addition of an amino acid residue at one of the positions of SEQ ID NO:8: 155, 156, 159, 162, 163, 164, 172, 173, 174, 175, 187, 188, 189, 190, 191, 192, 193, 194, 195, 196, 226, 227, 285, 286, 287, 291, 326, 331, 360, 361, 395, 396, 398, 440, or 441.

32. The method of any one of clauses 20-24, wherein said cinnamic acid decarboxylase is a mutant cinnamic acid decarboxylase that comprises a substitution of an amino acid residue at one of the positions of SEQ ID NO:8: 155, 156, 159, 162, 163, 164, 172, 173, 174, 175, 187, 188, 189, 190, 191, 192, 193, 194, 195, 196, 226, 227, 285, 286, 287, 291, 326, 331, 360, 361, 395, 396, 398, 440, or 441.

33. The method of any one of clauses 20-24, wherein said cinnamic acid decarboxylase is a mutant cinnamic acid decarboxylase that comprises a deletion, a substitution, or an addition of an amino acid residue at one of the positions of SEQ ID NO:8: 175 or 190.

34. The method of any one of clauses 20-33, wherein said linker is a peptide linker comprising 2 to 15 amino acids.

35. The method of any one of clauses 20-34, wherein said linker is a peptide linker consisting essentially of glycine and serine.

36. The method of any one of clauses 20-35, wherein said linker comprises an amino acid sequence as set forth in any one of SEQ ID NOs. 39-44.

37. A cinnamic acid decarboxylase comprising (i) any one of SEQ ID NOs: 16, 18, 20, 22, 24, 26, 28, 30, 32, 34, 36, and 38; (ii) an amino acid sequence that is about 85% identical to any one of SEQ ID NOs: 16, 18, 20, 22, 24, 26, 28, 30, 32, 34, 36, and 38, with the proviso that said amino acid sequence is not SEQ ID NO: 8; or (iii) a functional fragment of (i) or (ii).

38. The cinnamic acid decarboxylase of clause 37, wherein said amino acid sequence comprises: I at a position corresponding to residue 173 of SEQ ID NO: 8, A at a position corresponding to residue 174 of SEQ ID NO: 8, R at a position corresponding to residue 175 of SEQ ID NO: 8, V at a position corresponding to residue 188 of SEQ ID NO: 8, I at a position corresponding to residue 189 of SEQ ID NO: 8, K at a position corresponding to residue 190 of SEQ ID NO: 8, I at a position corresponding to residue 194 of SEQ ID NO: 8, E at a position corresponding to residue 280 of SEQ ID NO: 8, M at a position corresponding to residue 286 of SEQ ID NO: 8, F at a position corresponding to residue 291 of SEQ ID NO: 8, and F at a position corresponding to residue 440 of SEQ ID NO: 8.

39. The cinnamic acid decarboxylase of clause 37 or 38, comprising any one of SEQ ID NOs: 16, 18, 20, 22, 24, 26, 28, 30, 32, 34, 36, and 38.

40. A mutant cinnamic acid decarboxylase comprising a mutation at an amino acid residue position corresponding to one of the following positions: 155, 156, 159, 162, 163, 164, 172, 173, 174, 175, 187, 188, 189, 190, 191, 192, 193, 194, 195, 196, 226, 227, 285, 286, 287, 291, 326, 331, 360, 361, 395, 396, 398, 440, or 441 of SEQ ID NO:8.

41. The mutant cinnamic acid decarboxylase of clause 40, comprising a mutation at an amino acid residue position corresponding to one of the following positions: 175 or 190 of SEQ ID NO: 8.

42. A mutant cinnamic acid decarboxylase comprising a deletion, a substitution, or an addition of an amino acid residue at one of the positions of SEQ ID NO:8: 155, 156, 159, 162, 163, 164, 172, 173, 174, 175, 187, 188, 189, 190, 191, 192, 193, 194, 195, 196, 226, 227, 285, 286, 287, 291, 326, 331, 360, 361, 395, 396, 398, 440, or 441.

43. The mutant cinnamic acid decarboxylase of clause 42, comprising a substitution of an amino acid residue at one of the positions of SEQ ID NO:8: 155, 156, 159, 162, 163, 164, 172, 173, 174, 175, 187, 188, 189, 190, 191, 192, 193, 194, 195, 196, 226, 227, 285, 286, 287, 291, 326, 331, 360, 361, 395, 396, 398, 440, or 441.

44. The mutant cinnamic acid decarboxylase of clause 42, comprising a deletion, a substitution, or an addition of an amino acid residue at one of the positions of SEQ ID NO:8: 175 or 190.

45. A nucleic acid encoding the cinnamic acid decarboxylase of clause 37-44.

46. A host cell comprising the cinnamic acid decarboxylase of clause 37-44.

47. A host cell comprising the nucleic acid of clause 45.

48. A method for the production of styrene comprising: (a) contacting a host cell with a fermentable carbon substrate, said host comprises (i) a phenylalanine ammonia lyase; and (ii) a cinnamic acid decarboxylase of any one of clauses 37-44; (b) culturing said cell in a culture medium for a time sufficient to produce styrene.

49. The method of clause 48, further comprising harvesting styrene from said cell culture.

50. The method of clause 48 or 49, wherein said phenylalanine ammonia lyase is derived from an organism selected from the group consisting of: an *Arabidopsis*, an *Anabaena*, a *Nostoc*, and a *Saccharomyces*.

51. The method of any one of clauses 48-50, wherein said phenylalanine ammonia lyase comprises an amino acid sequence selected from the group consisting of: SEQ ID NO:2, SEQ ID NO:4, SEQ ID NO:6, and a functional fragment or variant thereof.

52. A host cell comprising: (i) a recombinantly expressed phenylalanine ammonia lyase; (ii) a recombinantly expressed cinnamic acid decarboxylase; and (iii) a recombinantly expressed ABC-transporter.

53. The host cell of clause 52, wherein said phenylalanine ammonia lyase is derived from an organism selected from the group consisting of: an *Arabidopsis*, an *Anabaena*, a *Nostoc*, and a *Saccharomyces*.

54. The host cell of clause 52 or 53, wherein said phenylalanine ammonia lyase comprises an amino acid sequence selected from the group consisting of: SEQ ID NO:2, SEQ ID NO:4, SEQ ID NO:6, and a functional fragment or variant thereof.

55. The host cell of any one of clauses 52-54, wherein said cinnamic acid decarboxylase is derived from an organism selected from the group consisting of: an *Arabidopsis*, an *Anabaena*, a *Nostoc*, and a *Saccharomyces*.

56. The host cell of any one of clauses 52-55, wherein said cinnamic acid decarboxylase comprises an amino acid sequence selected from the group consisting of: SEQ ID NOs: 8, 10, 16, 18, 20, 22, 24, 26, 28, 30, 32, 34, 36, 38, and a functional fragment or variant thereof.

57. The host cell of clause 56, wherein said cinnamic acid decarboxylase comprises an amino acid sequence selected from the group consisting of: SEQ ID NOs: 8, 10, 16, 18, 20, 22, 24, 26, 28, 30, 32, 34, 36, and 38.

58. The host cell of clause 56, wherein said functional variant comprises an amino acid sequence that is about 85% identical to any one of SEQ ID NOs: 8, 10, 16, 18, 20, 22, 24, 26, 28, 30, 32, 34, 36, and 38.

59. The host cell of clause 56 or 58, wherein said functional variant comprises: I at a position corresponding to residue 173 of SEQ ID NO: 8, A at a position corresponding to residue 174 of SEQ ID NO: 8, R at a position corresponding to residue 175 of SEQ ID NO: 8, V at a position corresponding to residue 188 of SEQ ID NO: 8, T at a position corresponding to residue 189 of SEQ ID NO: 8, K at a position corresponding to residue 190 of SEQ ID NO: 8, I at a position corresponding to residue 194 of SEQ ID NO: 8, E at a position corresponding to residue 280 of SEQ ID NO: 8, M at a position corresponding to residue 286 of SEQ ID NO: 8, F at a position corresponding to residue 291 of SEQ ID NO: 8, and F at a position corresponding to residue 440 of SEQ ID NO: 8.

60. The host cell of any one of clauses 52-55, wherein said cinnamic acid decarboxylase is a mutant cinnamic acid decarboxylase that comprises a mutation at an amino acid residue position corresponding to one of the following positions: 155, 156, 159, 162, 163, 164, 172, 173, 174, 175, 187, 188, 189, 190, 191, 192, 193, 194, 195, 196, 226, 227, 285, 286, 287, 291, 326, 331, 360, 361, 395, 396, 398, 440, or 441 of SEQ ID NO:8.

61. The host cell of any one of clauses 52-55, wherein said cinnamic acid decarboxylase is a mutant cinnamic acid decarboxylase that comprises a mutation at an amino acid residue position corresponding to one of the following: 155, 156, 159, 162, 163, 164, 172, 173, 174, 175, 187, 188, 189, 190, 191, 192, 193, 194, 195, 196, 226, 227, 285, 286, 287, 291, 326, 331, 360, 361, 395, 396, 398, 440, or 441 of SEQ ID NO: 8.

62. The host cell of any one of clauses 52-55, wherein said cinnamic acid decarboxylase is a mutant cinnamic acid decarboxylase that comprises a mutation at an amino acid residue position corresponding to one of the following positions: 175 or 190 of SEQ ID NO: 8.

63. The host cell of any one of clauses 52-55, wherein said cinnamic acid decarboxylase is a mutant cinnamic acid decarboxylase that comprises a deletion, a substitution, or an addition of an amino acid residue at one of the positions of SEQ ID NO:8: 155, 156, 159, 162, 163, 164, 172, 173, 174, 175, 187, 188, 189, 190, 191, 192, 193, 194, 195, 196, 226, 227, 285, 286, 287, 291, 326, 331, 360, 361, 395, 396, 398, 440, or 441.

64. The host cell of any one of clauses 52-55, wherein said cinnamic acid decarboxylase is a mutant cinnamic acid decarboxylase that comprises a substitution of an amino acid residue at one of the positions of SEQ ID NO:8: 155, 156, 159, 162, 163, 164, 172, 173, 174, 175, 187, 188, 189, 190, 191, 192, 193, 194, 195, 196, 226, 227, 285, 286, 287, 291, 326, 331, 360, 361, 395, 396, 398, 440, or 441.

65. The host cell of any one of clauses 52-55, wherein said cinnamic acid decarboxylase is a mutant cinnamic acid decarboxylase that comprises a deletion, a substitution, or an addition of an amino acid residue at one of the positions of SEQ ID NO:8: 175 or 190.

66. The host cell of any one of clauses 52-65, wherein said phenylalanine ammonia lyase and said cinnamic acid decarboxylase are covalently linked by a linker.

67. The host cell of clause 66, wherein said linker is a peptide linker comprising 2 to 15 amino acids.

68. The host cell of clause 66 or 67, wherein said linker is a peptide linker consisting essentially of glycine and serine.

69. The host cell of any one of clauses 66-68, wherein said linker comprises an amino acid sequence as set forth in SEQ ID NOs. 39-44.

70. The host cell of any one of clauses 52-69, wherein said ABC transporter is a bacterial ABC transporter.

71. The host cell of clause any one of clauses 52-70, wherein said ABC transporter is derived from *Pseudomonas putida*.

72. The host cell of clause any one of clauses 52-71, wherein said ABC transporter is a solvent resistance efflux pump.

73. The host cell of clause any one of clauses 52-72, wherein said ABC transporter is SrpABC pump derived from *Pseudomonas putida* S12.

74. A method for screening a candidate proteins for cinnamic acid decarboxylase activity, comprising: (a) providing a protein sample comprising said candidate protein, and a substrate sample comprising trans-cinnamic acid; (b) combining said protein sample and substrate sample to form a mixture, and incubating said mixture under a condition that allows a cinnamic acid decarboxylase to convert trans-cinnamic acid to styrene; and (c) exposing said mixture to a detection material that comprises (i) polymeric resin that absorbs styrene vapor; and (ii) a detectable marker that causes a color change in the presence of styrene; wherein a change of the color of said detection material indicates that said candidate protein has cinnamic acid decarboxylase activity.

75. The method of clause 74, further comprising comparing the activity of said candidate protein with a control.

76. The method of clause 74 or 75, wherein said detection material is attached to a solid support.

77. The method of any one of clauses 74-76, said polymeric resin comprises an aromatic functional group.

78. The method of any one of clauses 74-77, wherein said change of color is detected by spectrophotometry.

79. The method of any one of clauses 74-78, wherein said detectable marker is 4-nitrobenzyl-pyridine.

80. The method of clause 79, wherein said change of color is detected by measuring the absorbance of the sample at about 600 nm wavelength.

81. The method of any one of clauses 74-80, wherein a plurality of candidate proteins are screening simultaneously.

82. A method of isolating a recombinantly produced cinnamic acid decarboxylase, comprising: (a) providing a bacterial host comprising a nucleic acid that encodes a cinnamic acid decarboxylase operably linked to a promoter sequence; (b) culturing said bacterial host in a culture medium to express said cinnamic acid decarboxylase in said host cell, therein said host cell is cultured at a temperature that is from about 10° C. to about 25° C.; and (c) isolating said cinnamic acid decarboxylase from said host cell, wherein said isolation is conducted in an anaerobic environment.

83. The method of clause 82, wherein one or more buffer solutions used for isolating said cinnamic acid decarboxylase comprises a reducing agent.

84. The method of clause 83, wherein said reducing agent is Tris(2-carboxyethyl) phosphine (TCEP) or β-mercaptoethanol.

DETAILED DESCRIPTION

A. Overview

Figure 1A:
FIG. 1A is a schematic illustration of the predicted structure of yeast FDC1.

The subject technology generally relates to biosynthesis of styrene. Certain embodiments of the subject technology is based, in part, on the recognition that phenylalanine can be converted to styrene by a two-step pathway of deamination and decarboxylation, with trans-cinnamic acid (tCA) as the intermediate. Two types of enzymes are directly involved in this process, phenylalanine ammonia lyase (PAL), which converts phenylalanine to tCA, and cinnamic acid decarboxylase, which coverts tCA to styrene. Host cells expressing these two types of enzymes can be cultured in bioreactor to produce styrene from renewable substrates such as glucose.

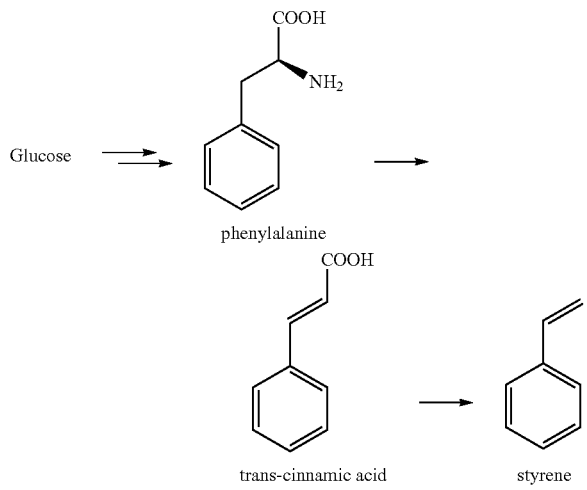

In particular, several approaches have been adopted to enhance the bioproduction of styrene. For example, as described and exemplified herein, fusion proteins have been designed in which phenylalanine ammonia lyase and cinnamic acid decarboxylase are covalently linked by a linker. The fusion protein takes advantage of the "substrate channeling" phenomenon. Substrate channeling refers to a phenomenon in which substrates are efficiently delivered from enzyme to enzyme without equilibration with other pools of the same substrates. In effect, this creates local pools of metabolites at high concentrations relative to those found in other areas of the cell. Because the product of phenylalanine ammonia lyase (trans-cinnamic acid) is consumed by cinnamic acid decarboxylase, proximity between these two enzymes (by covalently linking the two enzymes in the form of a fusion protein) would provide for a more efficient use of the substrate. As such, fusion proteins linking these two enzymes benefit from the substrate channeling phenomenon, and can reduce production costs and increase the number of enzymatic reactions that occur during a given time period. Alternatively, a protein complex in which the phenylalanine ammonia lyase and cinnamic acid decarboxylase form a protein complex via non-covalent interaction can also be used.

Accordingly, in one aspect, the subject technology provides a fusion protein comprising: (i) a first domain that comprises a phenylalanine ammonia lyase, and (ii) a second domain that comprises a cinnamic acid decarboxylase. Host cells comprising fusion proteins described herein, as well as method of using the fusion protein for styrene production are also provided.

In another approach, a library of mutant cinnamic acid decarboxylases have been designed, and screened for their respective activities. Mutant cinnamic acid decarboxylases showing higher catalytic activities, as compared to that of wild type, were identified. Some of the mutant cinnamic acid decarboxylases described herein increased the styrene production by two- to three-fold. These mutant cinnamic acid decarboxylases can be introduced to host cells to promote the bioproduction of styrene.

In another aspect, a high throughput, colorimetric screening method can allow for large-scale screening of mutant cinnamic acid decarboxylases or fusion proteins. The colorimetric screening described herein is highly reproducible and can screen about 1,000 mutant cinnamic acid decarboxylases and fusion proteins in a single day. This can provide fast and recursive screening of enzymes involved in biosynthesis of styrene and related compounds, providing an important method for improvement of styrene biosynthesis.

Accordingly, in another aspect, the subject technology provides mutant cinnamic acid decarboxylases, host cells comprising a mutant cinnamic acid decarboxylase, as well as method of using the mutant cinnamic acid decarboxylases for styrene production. Also provided herein are libraries of mutant cinnamic acid decarboxylases, and method of screening a candidate protein for cinnamic acid decarboxylase activity.

Another issue that limits the bioproduction of styrene is the toxicity of styrene to host cells. The accumulation of hydrophobic aromatics within the cytoplasmic membrane is known to disrupt its integrity. To reduce styrene toxicity and enhance production, an ABC-transporter was introduced into the host cell—an efflux pump that removes organic solvent from the cell. As described and exemplified herein, styrene production by E. coli cells expressing the ABC-transporter was enhanced nearly four times.

Accordingly, in another aspect, the subject technology provides a host cell comprising: (a) a recombinantly expressed phenylalanine ammonia lyase; (b) a recombinantly expressed cinnamic acid decarboxylase; and (c) a recombinantly expressed ABC-transporter. Method of using the ABC-transporter for styrene production is also provided.

B. Definitions

As used herein, the singular forms "a," "an" and "the" include plural references unless the content clearly dictates otherwise.

The terms "cinnamic acid" and "cinnamate" are used interchangeably in the specification, and are abbreviated as "CA." Trans-cinnamic acid is abbreviated as tCA.

The term "cinnamic acid decarboxylase" refers to an enzyme that catalyzes the conversion of trans-cinnamic acid to styrene. The term encompasses wild type or naturally occurring cinnamic acid decarboxylase, as well as functional fragments or variants of a wild type cinnamic acid decarboxylase. The *Saccharomyces cerevisiae* cinnamic acid decarboxylase described herein is also termed ferulic acid decarboxylase (FDC or FDC1). Ferulic acid is also a phenylacrylic acid.

The term "control" as used herein refers to a sample that provides a basis for comparison. For example, in a screening assay to determine cinnamic acid decarboxylase activity, a "control" can be a parallel sample comprising a cinnamic acid decarboxylase whose activity has been characterized (e.g., a wild type cinnamic acid decarboxylase, a specific mutant cinnamic acid decarboxylase, etc.). Alternatively, a control may be a pre-determined threshold value, or a value that is present in a database (e.g., a table, electronic database, spreadsheet, etc.).

An amino acid position "corresponding to" a reference position is a position that aligns with a reference sequence, as identified by aligning the amino acid sequences. Such alignments can be done by hand or by using well-known sequence alignment programs such as ClustalW2, Blast 2, etc.

A protein is "derived" from an organism when the protein is isolated from that organism, or modified or generated (e.g., chemically synthesized or recombinantly produced) using information of the protein from that organism The term "detectable marker" refers to a chemical compound that is added to (or coated onto) a styrene-absorption material, in an amount effective to detect styrene vapor. Preferred detectable markers are chemical compounds that undergo a chemical reaction in the presence of styrene, and produce a colorimetric species. The chemical response of the detectable marker is preferable concentration dependent.

The term "fermentable carbon substrate" refers to a carbon source capable of being metabolized by host cells as described herein, and particularly carbon sources selected from the group consisting of monosaccharides, oligosaccharides, polysaccharides, one-carbon substrate, and a combination thereof.

The term "functional fragment" of protein refers to refers to a peptide fragment that is a portion of the full length protein, and has substantially the same biological activity, or carries out substantially the same function as the full length protein (e.g., carrying out the same enzymatic reaction). For example, a functional fragment of a PAL can catalyze the phenylalanine to cinnamic acid conversion, and a functional fragment of a FDC can catalyze the cinnamic acid to styrene conversion.

The term "functional variant" of protein refers to a protein in which one or more amino acid residues have been changed without altering the overall conformation and function of the reference protein. Functional variants includes, e.g., replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide.

The term "homologous" in all its grammatical forms and spelling variations refers to the relationship between polynucleotides or proteins that possess a "common evolutionary origin," including polynucleotides or proteins from superfamilies and homologous polynucleotides or proteins from different species (Reeck et al., Cell 50:667, 1987). Such polynucleotides or proteins have sequence homology, as reflected by their sequence similarity, whether in terms of percent identity or the presence of specific amino acids or motifs at conserved positions. For example, two homologous proteins can have amino acid sequences that are about 80%, about 85%, about 90%, about 95%, about 96%, about 97%, about 98%, about 99%, or even 100% identical.

In this sense, techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" may then be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity", as can two or more amino acid sequences. The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known by those skilled in the art.

The terms "mutation," or "mutant" as used herein, refer to a deletion, an insertion, or a substitution of a nucleotide or an amino acid residue of a wild type sequence. A wild type sequences refers to the most frequent sequence found in nature, against which mutants are defined.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "phenylalanine ammonia lyase," abbreviated PAL, refers to an enzyme that catalyzes the conversion of phenylalanine to trans-cinnamic acid. The term encompasses wild type or naturally occurring phenylalanine ammonia lyase, as well as functional fragments or variants of a wild type phenylalanine ammonia lyase.

The term "mutated cinnamic acid decarboxylase" refers to an enzyme that catalyzes the conversion of trans-cinnamic acid to styrene, or the conversion of coumaric acid to 4-hydroxystyrene.

The term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The team "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined, italicized and/or boldface headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Unless specified otherwise, the percent identity of two polypeptide or polynucleotide sequences refers to as the percentage of identical amino acid residues or nucleotides across the entire length of the shorter of the two sequences.

C. Phenylalanine Ammonia Lyase

Phenylalanine ammonia lyase (EC 4.3.1.24; formally EC 4.3.1.5) is an enzyme that catalyzes the chemical reaction:

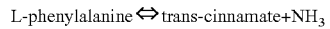

L-phenylalanine ⇔ trans-cinnamate+NH$_3$

Other names that are commonly used for this enzyme include tyrase, phenylalanine deaminase, tyrosine ammonialyase, L-tyrosine ammonia-lyase, phenylalanine ammonium-lyase, PAL, and L-phenylalanine ammonia-lyase. PAL is a non-mammalian enzyme widely distributed in plants and yeast.

A representative list of PALs include (identified by Genbank accession number and species): Q9ATN7 *Agastache rugosa;* 093967 *Amanita muscaria* (Fly agaric); P35510, P45724, P45725, Q9SS45, Q8RWP4 *Arabidopsis thaliana* (Mouse-ear cress); Q6ST23 *Bambusa oldhamii* (Giant timber bamboo); Q42609 *Bromheadia finlaysoniana* (Orchid); P45726 *Camellia sinensis* (Tea); Q9MAX1 *Catharanthus roseus* (Rosy periwinkle) (Madagascar periwinkle); Q9SMK9 *Cicer arietinum* (Chickpea); Q9XFX5, Q9XFX6 *Citrus clementina×Citrus reticulate*; Q42667 *Citrus Ziman* (Lemon); Q8H6V9, Q8H6W0 *Coffea canephora* (Robusta coffee); Q852S1 *Daucus carota* (Carrot); 023924 *Digitalis lanata* (Foxglove); 023865 *Daucus carota* (Carrot); P27991 *Glycine max* (Soybean); 004058 *Helianthus annuus* (Common sunflower); P14166, (Q42858) *Ipomoea batatas* (Sweet potato); Q8GZR8, Q8W2E4 *Lactuca sativa* (Garden lettuce); 049835, 049836 *Lithospermum erythrorhizon*; P35511, P26600 *Lycopersicon esculentum* (Tomato); P35512 *Malus domestica* (Apple) (*Malus sylvestris*); Q94C45, Q94F89 *Manihot esculenta* (Cassaya) (Manioc); P27990 *Medicago sativa* (Alfalfa); P25872, P35513, P45733 *Nicotiana tabacum* (Common tobacco); Q6T1C9 *Quercus suber* (Cork oak); P14717, P53443, Q7M1Q5, Q84VE0, Q84VE0 *Oryza sativa* (Rice); P45727 *Persea americana* (Avocado); Q9AXI5 *Pharbitis nil* (Violet) (Japanese morning glory); P52777 *Pinus taeda* (Loblolly pine); Q01861, Q04593 *Pisum sativum* (Garden pea); P24481, P45728, P45729 *Petroselinum crispum* (Parsley) (*Petroselinum hortense*); Q84L12 *Phalaenopsis×Doritaenopsis* hybrid cultivar; P07218, P19142, P19143 *Phaseolus vulgaris* (Kidney bean) (French bean); Q7XJC3, Q7XJC4 *Pinus pinaster* (Maritime pine); Q6UD65 *Populus balsamifera* subsp. *trichocarpa×Populus deltoides*; P45731, Q43052, 024266 *Populus kitakamiensis* (Aspen); Q8H6V5, Q8H6V6 *Populus tremuloides* (Quaking aspen); P45730 *Populus trichocarpa* (Western balsam poplar); 064963 *Prunus avium* (Cherry); Q94ENO *Rehmannia glutinosa*; P11544 *Rhodosporidium toruloides* (Yeast) (*Rhodotorula gracilis*); P10248 *Rhodotorula rubra* (Yeast) (*Rhodotorula mucilaginosa*); Q9M568, Q9M567 *Rubus idaeus* (Raspberry); P31425, P31426 *Solanum tuberosum* (Potato); Q6SPE8 *Stellaria longipes* (Longstalk starwort); P45732 *Stylosanthes humilis* (Townsville stylo); P45734 *Trifolium subterraneum* (Subterranean clover); Q43210, Q43664 *Triticum aestivum* (Wheat); Q96V77 *Ustilago maydis* (Smut fungus); P45735 *Vitis vinifera* (Grape); and Q8VXG7 *Zea mays* (Maize).

Crystal structures of several PALs are also known (identified by PDB accession code and species): 1T6J (*Rhodosporidium toruloides*); 1T6P (*Rhodosporidium toruloides*); 1W27 (*Petroselinum crispum*); 1Y2M (*Rhodosporidium toruloides*); 2NYF (*Nostoc punctiforme*); and 3nz4 (*Taxes canadensis*). PAL from *Rhodosporidium toruloides* (also known as *Rhodotorula glutinis*) is a homotetramer, each subunit having a "seahorse" shape that interlocks head-to-tail with two other subunits, thereby maximizing adjacent subunit interactions and yielding a close-fitting tetramer. The tetramer assembly leads to a cluster of four vicinal cysteines (residues 140, 455, 467, and 530), with the sulfur atoms of Cys467 and Cys530 separated by 3.62 angstroms. The structure of the main body of PAL has a central core of nearly parallel α-helices of varying lengths. There is only one section of β-sheet longer than three residues (strands of residues 231-237 and 240-246); it resides in the funnel region leading to the active site. MacDonald, et al., A modern view of phenylalanine ammonia lyase, Biochem Cell Biol. 2007; 85(3):273-82.

Genes or polynucleotides encoding PAL from both plant and microbial sources are known in the art. See, for example, EP 321488 (*R. toruloides*); WO 9811205 (*Eucalyptus grandis* and *Pinus radiate*); WO 9732023 (*Petunia*); JP 05153978 (*Pisum sativum*); WO 9307279 (potato, rice). The sequences of various PAL genes can be readily ascertained from literature, public databases (see for example GENBANK® Accession Nos. AJ010143 and X75967), or other commercial sources. For example, full-length cDNAs of *Arabidopsis* PAL1 (At2g37040), PAL2 (At3g53260) and PAL4 (At3g10340) can be purchased from *Arabidopsis* Biological Resource Center (ABRC) at the Ohio State University under the stock numbers G10120 (in pENTR223.1 vector), G12256 (in pENTR223.1 vector), and U24927 (in pENTR/D-TOPO vector), respectively.

In certain embodiments, the phenylalanine ammonia lyase of the subject technology is derived from an organism selected from the group consisting of: an *Arabidopsis*, an *Anabaena*, a *Nostoc*, and a *Saccharomyces*. Other preferred source organisms include, e.g., yeasts such as *Rhodotorula*, *Rhodosporidium*, and *Sporobolomyces*; bacteria such as *Streptomyces*; and plants such as pea, potato, rice, *eucalyptus*, pine, corn, *petunia, arabidopsis*, tobacco, and parsley.

The subject technology also encompasses homologs (including orthologs), functional fragments, or functional variants of the exemplary PALs described herein. Methods of obtaining homologs and variants of PALs are well known in the art, including for example, sequence-dependent protocols. Exemplary sequence-dependent protocols include, e.g., nucleic acid hybridization, DNA and RNA amplification (e.g., polymerase chain reaction (PCR), ligase chain reaction (LCR)), etc.

For example, genes encoding homologs of a PAL can be isolated directly by using all or a portion of the known sequences as DNA hybridization probes to screen libraries from any desired plant, fungi, yeast, or bacteria, using techniques well known to those skilled in the art. Specific oligonucleotide probes based upon the literature nucleic acid sequences can be designed and synthesized by methods known in the art (Maniatis, infra). Moreover, the entire sequences can be used directly to synthesize DNA probes by methods known to a skilled artisan, such as random primers DNA labeling, nick translation, or end-labeling techniques, or RNA probes using available in vitro transcription systems. In addition, specific primers can be designed and used to amplify a part of or full-length of a target sequences. The resulting amplification products can be labeled directly during amplification reactions, or labeled after amplification reactions, and used as probes to isolate full-length cDNA or genomic fragments under conditions of appropriate stringency.

In addition, two short segments of the literature sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the literature sequences, and the sequence of the other primer takes advantage of the presence of the polyadenylic acid tracts to the 3' end of the mRNA precursor encoding bacterial genes. Alternatively, the second primer sequence may be based upon sequences derived from the cloning vector. For example, the skilled artisan can follow the RACE protocol (Frohman et al., PNAS USA 85:8998 (1988)) to generate cDNAs by using PCR to amplify copies of the region between a single point in the transcript and the 3' or 5' end. Primers oriented in the 3' and 5' directions can be designed from the literature sequences. Using commercially available 3' RACE or 5' RACE systems, specific 3' or 5' cDNA fragments can be isolated (Ohara et al., Proc. Natl. Acad. Sci. USA 86:5673 (1989); Loh et al., Science 243:217 (1989)).

The nucleic acid and protein sequences of a homolog or a variant can further be identified by using a "query sequence" to perform a search against public databases to identify other family members or related sequences.

Accordingly, in an exemplary embodiment, the phenylalanine ammonia lyase of the subject technology comprises an amino acid sequence selected from the group consisting of: SEQ ID NO:2, SEQ ID NO:4, SEQ ID NO:6, and a functional fragment or variant thereof. SEQ ID NO:2, SEQ ID NO:4, and SEQ ID NO:6 are the amino acid sequences of *Arabidopsis* PAL1, PAL2, and PAL4, respectively. Variants of PAL may include those polypeptide sequences comprising an amino acid sequence that is about 60%, about 70%, about 75%, about 80%, about 85%, about 90%, about 95%, about 96%, about 97%, or about 98%, about 99%, or even 100% identical to any one of SEQ ID NO:2, SEQ ID NO:4, SEQ ID NO:6, or a fragment thereof. The fragment may comprise about 100, 150, 200, 250, 300, 350, 400, 450, 500, 550, 600, 650, 700, or 750 amino acid residues of the full length PAL.

In another exemplary embodiment, the phenylalanine ammonia lyase of the subject technology comprises an amino acid sequence encoded by a polynucleotide sequence selected from the group consisting of: SEQ ID NO:1, SEQ ID NO:3, SEQ ID NO:5, and a fragment or variant thereof. SEQ ID NOs:1, SEQ ID NO:3, and SEQ ID NO:5 are the nucleotide sequences encoding *Arabidopsis* PAL1, PAL2, and PAL4, respectively. Variants of PAL-coding sequence may include those polynucleotide sequences that is about 60%, about 70%, about 75%, about 80%, about 85%, about 90%, about 95%, about 96%, about 97%, about 98%, about 99%, or even 100% identical to any one of SEQ ID NO:1, SEQ ID NO:3, SEQ ID NO:5, or a fragment thereof. The fragment may comprise about 300, 400, 500, 600, 700, 800, 900, 1000, 1100, 1200, 1300 1400, 1500, 1600, 1700, 1800, 1900, 2000, or 2100 nucleotides of the full length PAL-coding sequence.

To determine the percent identity of two amino acid sequences or of two polynucleotide sequences, the sequences are aligned for optimal comparison purposes (e.g., gaps can be introduced in the sequence of a first amino acid or nucleic acid sequence for optimal alignment with a second amino or nucleic acid sequence and non-homologous sequences can be disregarded for comparison purposes). Unless specified otherwise, an alignment is a global alignment, (i.e., the percentage of identical amino acid residues or nucleotides across the entire length of the shorter of the two sequences). If a local alignment is desired, preferably, the length of a sequence aligned for comparison is about 30%, about 40%, about 50%, about 60%, about 70%, about 80%, or about 90% of the length of the shorter of the two sequences.

D. Cinnamic Acid Decarboxylase

Cinnamic acid decarboxylase is an enzyme that catalyzes the conversion of trans-cinnamic acid to styrene.

In certain embodiments, the cinnamic acid decarboxylase of the subject technology is derived from an organism selected from the group consisting of: an *Arabidopsis*, an *Anabaena*, a *Nostoc*, and a *Saccharomyces*.

1. FDC1 and OHBA1

In an exemplary embodiment, the cinnamic acid decarboxylase of the subject technology is derived from *Saccharomyces cerevisiae*. The *Saccharomyces cerevisiae* cinnamic acid decarboxylase described herein is also termed ferulic acid decarboxylase (FDC or FDC1). The sequence of FDC/FDC1 is disclosed in U.S. Pat. Nos. 5,955,137 and 6,468,566.

Figure 1B:
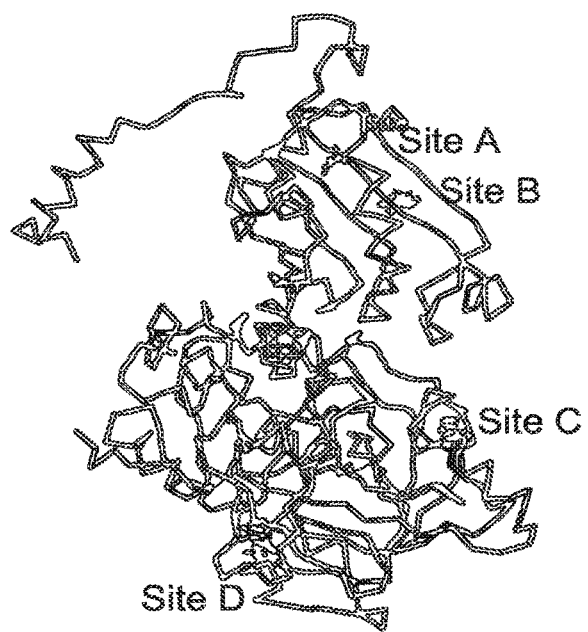
FIG. 1B shows four possible tCA binding sites in FDC1 (sites A-D).
Figure 1C:
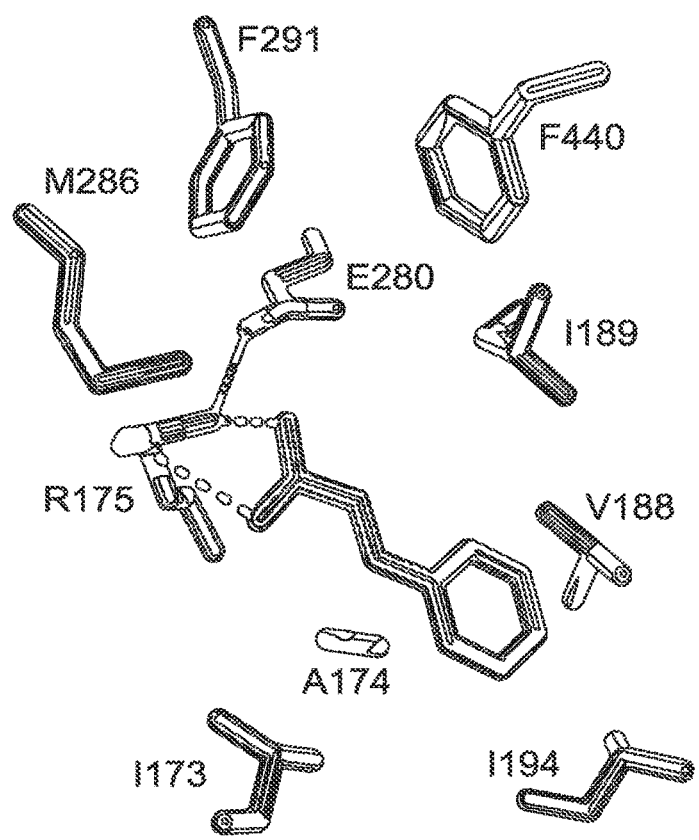
FIG. 1C shows the predicted substrate (tCA) binding site in yeast FDC1.

As disclosed and exemplified herein, full length cinnamic acid decarboxylase from *Saccharomyces cerevisiae* comprises 503 amino acids (SEQ ID NO:8). A computer model of full length FDC1 is shown in FIG. 1A; and four possible tCA binding sites are shown in FIG. 1B, with site C being the most likely site. Further analysis of site C shows that I173, A174, R175, V188, I189, K190 (not shown for figure clarification), I194, E280, M286, F291 and F440 are involved with substrate binding (FIG. 1C). The nucleotide sequence encoding FDC1 is shown as SEQ ID NO:7.

Kinetic studies show that the Km for wild type FDC is about 688 μM and the $V_{max}$ is about 6.17 nmol·mg$^{-1}$·min$^{-1}$. In addition to tCA, FDC1 also binds to substrates including ferulic acid, 2-methylcinnamic acid, and 4-hydroxycinnamic acid.

Another exemplary cinnamic acid decarboxylase is 3-octaprenyl-4-hydroxybenzoate carboxy-lyase from *Aspergillus niger* (OHBA1; SEQ ID NO:10). The nucleotide sequence encoding OHBA1 is shown as SEQ ID NO:9.

The subject technology also encompasses homologs (including orthologs), functional fragments, or functional variants of the exemplary cinnamic acid decarboxylases described herein. Homologs and variants of cinnamic acid decarboxylases can be obtained using methods described above.

For example, a functional variant may be a sequence that (i) is about 50%, about 60%, about 70%, about 80%, about 85%, about 90%, about 95%, about 96%, about 97%, about 98%, about 99%, or even 100% identical to SEQ ID NO:8, (ii) comprises at least 1, at least 2, at least 3, at least 4, at least 5, at least 6, at least 7, at least 8, at least 9, or at least 10 of the following residues: I at a position corresponding to residue 173 of SEQ ID NO: 8, A at a position corresponding to residue 174 of SEQ ID NO: 8, R at a position corresponding to residue 175 of SEQ ID NO: 8, V at a position corresponding to residue 188 of SEQ ID NO: 8, I at a position corresponding to residue 189 of SEQ ID NO: 8, K at a position corresponding to residue 190 of SEQ ID NO: 8, 1 at a position corresponding to residue 194 of SEQ ID NO: 8, E at a position corresponding to residue 280 of SEQ ID NO: 8, M at a position corresponding to residue 286 of SEQ ID NO: 8, F at a position corresponding to residue 291 of SEQ ID NO: 8, and F at a position corresponding to residue 440 of SEQ ID NO: 8; and a combination of (i) and (ii).

Amino acid residues that "correspond to" a particular position of SEQ ID NO: 8 can be identified by aligning the target sequence with SEQ ID NO: 8. As an example, alignment of FDC1 and OHBA1 is shown below (FDC1 is the query sequence; OHBA1 is the subject sequence).

```
Query   8 LEFRDFIQVLKDEDDLIEITEEIDPNLEVGAIMMKAYESHLPAPLFKNLKGASKDLFSIL   67
          L FR F++ LK ++DL+EI   IDPNLE  AI R+  E++  APLF NL G    LF IL
Sbjct   8 LCFRSFVEALKVDNDLVEINTPIDPNLEAAAITRRVCETNDKAPLFNNLIGMKNGLFRIL   67

Query  68 GCPAGLRSKEKGDHGRIAHHLGLDPKTTIKEIIDYLLECKEKEPLPPITVPVSSAPCKTH  127
             G P  LR     +GR+A HL L P  +++EI+D +L    + P+      V + PCK +
Sbjct  68 GAPGSLRKSSADRYGRLARHLALPPTASMREILDKMLSASDMPPI--PPTIVPTGPCKEN  125

Query 128 ILSEEKIHLQSLPTPYLHVSDGGKYLQTYGMWILQTPDKKWTNWSIARGMVVDDKHITGL  187
            L + +  L  LP P +H SDGGKY+QTYGM I+Q+PD  WTNWSIAR MV D  H+TGL
Sbjct 126 SLDDSEFDLTELPVPLIHKSDGCKYIQTYGMHIVQSPDGTWTNWSIARAMVHDKNHLTGL  185
```

```
                                                 -continued
Query 188 VIKPQHIRQIADSWAAIGKANEIPFALCFGVPPAAILVSSMPIPEGVSESDYVGAILGES      247
             VI PQHI QI    W   G++ ++P+AL FGVPPAAI+ SSMPIP+GV+E+ YVGA+ G S
Sbjct 186 VIPPQHIWQIHQMWKKEGRS-DVPWALAFGVPPAAIMASSMPIPDGVTEAGYVGAMTGSS        244

Query 248 VPVVKCETNDLMVPATSEMVFEGTLSLTDTHLEGPFGEMHGYVFKSQGHPCPLYTVKAMS        307
              + +VKC+TNDL VPATSE+V EGTLS+++T EGPFGEMHGY+F     H     Y V ++
Sbjct 245 LELVKCDTNDLYVPATSEIVLEGTLSISETGPEPGPFGEMHGYIFPGDTHLGAKYKVNRIT      304

Query 308 YRDNAILPVSNPGLCTDETHTLIGSLVATEAKELAIESGLPILDAFMPYEAQALWLILKV        367
             YR+NAI+P+S+ G  TDETHT+IGSL A E ++L  ++ LPI DAF P+E+Q  W+ L+V
Sbjct 305 YRNNAIMPMSSCGRLTDETHTMIGSLAAAEIRKLCQQNDLPITDAFAPFESQVTWVALRV        364

Query 368 DLKGLQALKTTPEEFCKKVGDIYFRTYVGFIVHEIILVADDIDIFNFKEVIWAYVTRHTP        427
              D + L+A+KTT E F K+VGD+ F   K G+ +H ++LV DDID++   K+V+WA+ TR  P
Sbjct 365 DTEKLRAMKTTSEGFRKRVGDVVFNHKAGYTIHRLVLVGDDIDVYEGKDVLWAFSTRCRP        424

Query 428 VADQMAFDDVTSFPLAPFVSQSSRSKTMKGGKCVTNCIFRQQYERSFDYITCNFEKGYPK        487
               D+  F+DV  FPL P++    +     +GGK V++ +    +Y   ++    +F + YP+
Sbjct 425 GMDETLFEDVRGFPLIPYMGHGN-GPAHRGGKVVSDALMPTEYTTGRNWEAADFNQSYPE        483

Query 488 GLVDKVNENWKRYGY                                                    502
              L   KV +NW + G+
Sbjct 484 DLKQKVLDNWTKMGF                                                    498
```

In an exemplary embodiment, the cinnamic acid decarboxylase of the subject technology comprises an amino acid sequence selected from the group consisting of: SEQ ID NO:8, SEQ ID NO:10, and a functional fragment or variant thereof. Variants of cinnamic acid decarboxylase may include those polypeptide sequences comprising an amino acid sequence that is about 50%, about 60%, about 70%, about 75%, about 80%, about 85%, about 90%, about 95%, about 96%, about 97%, about 98%, about 99%, or even 100% identical to any one of SEQ ID NO:8, SEQ ID NO:10, or a fragment thereof. The fragment may comprise about 100, 150, 200, 250, 300, 350, 400, 450, 500, 550, 600, 650, 700, or 750 amino acid residues of the full length cinnamic acid decarboxylase.

In another exemplary embodiment, the cinnamic acid decarboxylase of the subject technology comprises an amino acid sequence encoded by a polynucleotide sequence selected from the group consisting of: SEQ ID NO:7, SEQ ID NO:9, and a fragment or variant thereof. Variants of cinnamic acid decarboxylase-coding sequence may include those polynucleotide sequences that is about 60%, about 70%, about 75%, about 80%, about 85%, about 90%, about 95%, about 96%, about 97%, about 98%, about 99%, or even 100% identical to any one of SEQ ID NO:7, SEQ ID NO:9, or a fragment thereof. The fragment may comprise about 300, 400, 500, 600, 700, 800, 900, 1000, 1100, 1200, 1300 1400, 1500, 1600, 1700, 1800, 1900, 2000, or 2100 nucleotides of the full length coding sequence.

2. Exemplary FDC1 Mutants

Based on the structural analysis of yeast FDC1, residues 155-156, 159, 162-164, 172-175, 187-196, 226-227, 280, 285-287, 291, 326, 331, 360-361, 395-396, 398, and 440-441 of FDC1 (SEQ ID NO:8) are identified as potential sites for mutagenesis. Accordingly, in another aspect, the subject technology provides a mutant cinnamic acid decarboxylase, wherein a mutation is introduced at an amino acid residue position corresponding to one of the following positions: 155, 156, 159, 162, 163, 164, 172, 173, 174, 175, 187, 188, 189, 190, 191, 192, 193, 194, 195, 196, 226, 227, 280, 285, 286, 287, 291, 326, 331, 360, 361, 395, 396, 398, 440, 441 of SEQ ID NO:8, and a combination thereof. The mutation may be a deletion, an insertion, or a substitution mutation.

In an exemplary embodiment, the mutant cinnamic acid decarboxylase comprises a mutation at an amino acid residue position corresponding to residue 190 of SEQ ID NO: 8. Preferably, the residue corresponding to 190 is replaced with one of the following: E, C, D, V, N, L, H. In another exemplary embodiment, the mutant cinnamic acid decarboxylase comprises a mutation at an amino acid residue position corresponding to residue 175 of SEQ ID NO: 8. Preferably, the residue corresponding to 175 is replaced with I.

In certain embodiments, the mutant cinnamic acid decarboxylase is a mutant FDC1, wherein a mutation is introduced to one of the following positions in SEQ ID NO:8: 155, 156, 159, 162, 163, 164, 172, 173, 174, 175, 187, 188, 189, 190, 191, 192, 193, 194, 195, 196, 226, 227, 280, 285, 286, 287, 291, 326, 331, 360, 361, 395, 396, 398, 440, 441, and a combination thereof.

In certain embodiments, the mutant cinnamic acid decarboxylase is a mutant FDC1, wherein a mutation is introduced to that one of the following positions in SEQ ID NO:8: 175, 190, 193, and a combination thereof.

In certain embodiments, the mutant cinnamic acid decarboxylase is a mutant FDC1, comprising one of the mutations in SEQ ID NO:8: K190E, K190C, K190H, K190P, K190L, K190R, K190D, K190V, K190S, K190N, R175I, H193P, and a combination thereof.

In certain embodiments, the mutant cinnamic acid decarboxylase comprises any one of the sequences selected from the group consisting of SEQ ID NO:16; SEQ ID NO:18; SEQ ID NO:20; SEQ ID NO:22; SEQ ID NO:24; SEQ ID NO:26; SEQ ID NO:28; SEQ ID NO:30; SEQ ID NO:32; SEQ ID NO:34; SEQ ID NO:36; and SEQ ID NO:38.

The cinnamic acid decarboxylase of the subject technology may also comprise a functional fragment or variant of the mutant cinnamic acid decarboxylase described herein. Variants of cinnamic acid decarboxylase may include those polypeptide sequences comprising an amino acid sequence that is about 50%, about 60%, about 70%, about 75%, about 80%, about 85%, about 90%, about 95%, about 96%, about 97%, about 98%, about 99%, or even 100% identical to any one of SEQ ID NO:16; SEQ ID NO:18; SEQ ID NO:20; SEQ ID NO:22; SEQ ID NO:24; SEQ ID NO:26; SEQ ID NO:28; SEQ ID NO:30; SEQ ID NO:32; SEQ ID NO:34; SEQ ID NO:36; SEQ ID NO:38; and a fragment thereof. The fragment may comprise about 100, 150, 200, 250, 300, 350, 400, 450, 500, 550, 600, 650, 700, or 750 amino acid residues of the full length cinnamic acid decarboxylase.

Alternatively, or in addition, the variants may comprise at least 1, at least 2, at least 3, at least 4, at least 5, at least 6, at least 7, at least 8, at least 9, or at least 10 the following residues: I at a position corresponding to residue 173 of SEQ ID NO: 8, A at a position corresponding to residue 174 of SEQ ID NO: 8, R at a position corresponding to residue 175 of SEQ ID NO: 8, V at a position corresponding to residue 188 of SEQ ID NO: 8, I at a position corresponding to residue 189 of SEQ ID NO: 8, K at a position corresponding to residue 190 of SEQ ID NO: 8, I at a position corresponding to residue 194 of SEQ ID NO: 8, E at a position corresponding to residue 280 of SEQ ID NO: 8, M at a position corresponding to residue 286 of SEQ ID NO: 8, F at a position corresponding to residue 291 of SEQ ID NO: 8, and F at a position corresponding to residue 440 of SEQ ID NO: 8.

Libraries of cinnamic acid decarboxylase mutants are also provided. The library comprises a plurality of mutant cinnamic acid decarboxylases. For example, the library may comprise cinnamic acid decarboxylase mutants that represent about 15, about 16, about 17, about 18, or about 19 different mutations at particular target position. For example, the library may comprise about 19 different mutants in which K190 of FDC1 (SEQ ID NO:8) is replaced with each one of the other 19 amino acids. Alternatively, the library may comprise cinnamic acid decarboxylase mutants that represents about 5, about 6, about 7, about 8, about 9, about 10, about 11, about 12, about 13, about 14, about 15, about 16, about 17, about 18, or about 19 mutations at different positions. For example, an Alanine scan may be used to create mutant libraries in which amino acid residues at different positions are replaced with Alanine.

Changes to the amino acid sequence may be generated by changing the nucleic acid sequence encoding the amino acid sequence. A nucleic acid sequence encoding a mutant cinnamic acid decarboxylase may be prepared by methods known in the art using the guidance of the present specification for particular sequences. These methods include, but are not limited to, preparation by site-directed (or oligonucleotide-mediated) mutagenesis (Coombs et al., Proteins (1998), 259-311, 1 plate. Editor(s): Angeletti, Ruth Hogue. Publisher: Academic, San Diego, Calif.); PCR mutagenesis or error prone PCR (Melnikov et al., Nucleic Acids Research, (Feb. 15, 1999) Vol. 27, No. 4, pp. 1056-1062); cassette mutagenesis of an earlier prepared nucleic acid sequence; "gene shuffling" (U.S. Pat. Nos. 5,605,793; 5,811,238; 5,830,721; and 5,837,458); all of which are techniques well known in the art.

Alternatively, in vivo mutagenesis may be employed using commercially available materials such as *E. coli* XL 1-Red strain, and the *Epicurian coli* XL 1-Red mutator strain from STRATAgene (STRATAgene, La Jolla, Calif., Greener and Callahan, Strategies 7:32-34) (1994)). This strain is deficient in three of the primary DNA repair pathways (mutS, mutD and mutT), resulting in a mutation rate 5000-fold higher than that of wild type.

3. Method of Screening

In another aspect, the subject technology provides a method for screening a candidate proteins for cinnamic acid decarboxylase activity, comprising (a) providing a protein sample comprising the candidate protein, and a substrate sample comprising trans-cinnamic acid; (b) combining the protein sample and substrate sample to form a mixture, and incubating the mixture under a condition that allows a cinnamic acid decarboxylase to convert trans-cinnamic acid to styrene; and (c) exposing the mixture to a detection material that comprises (i) polymeric resin that absorbs styrene vapor; and (ii) a detectable marker that causes a color change in the presence of styrene. A change of the color of the detection material indicates that the candidate protein has cinnamic acid decarboxylase activity.

In screening for FDC mutants, a high-throughput screening assay has been developed. Screening a large population of the protein library is the bottleneck for the molecular evolution of the protein. The functional characterization of decarboxylase routinely relies on analytic instruments, like HPLC or LC-MS. Although the HPLC is highly sensitive, it is time consuming, expensive, and generates waste like methanol or acetonitrile and not suitable for high-throughput applications.

To overcome these technical barriers, the subject technology provides a spectroscopic-based colorimetric assay method. First, a candidate protein and tCA are incubated under a condition that allows a cinnamic acid decarboxylase to convert trans-cinnamic acid to styrene. Typically, the incubation condition should allow a cinnamic acid decarboxylase to exhibit optimal enzymatic activity (for example, at a temperature from about 10° C. to about 65° C., from about 25° C. to about 55° C., from about 35° C. to about 60° C., or from about 35° C. to about 55° C.; at a pH between 6-10, between 6-8, or between 5.5-7.5; in the presence of metal ions from about 1 mM to about 20 mM; etc.). The candidate protein and tCA can be incubated for about 30 minutes, about 1 hour; about 90 minutes, about 2 hours, about 2.5 hours, about 3 hours, about 3.5 hours, about 4 hours, about 4.5 hours, about 5 hours, about 6 hours, about 7 hours, or about 8 hours, to allow sufficient amount of styrene to be produced.

Second, the reaction mixture is exposed to a detection material that comprises (i) polymeric resin that absorbs styrene vapor; and (ii) a detectable marker that causes a color change in the presence of styrene. Because styrene vaporizes, the detection material can be placed on top of the reaction mixture to absorb styrene vapor (without actually dipping into the reaction mixture). Accordingly, the detection material can be attached to a solid support, and can be inverted during the detection process to absorb styrene vapor. See, e.g., FIG. 19.

Preferred polymeric resins for absorbing styrene vapor include, e.g., reversed phase hydrophobic resins, which has a hydrocarbon or aromatic functional group (e.g., an aromatic benzene ring) that can bind with polar and non-polar compounds. More preferably, the hydrophobic resins have a hydrocarbon or aromatic functional group and do not have any polar group. Examples of the reversed phase hydrophobic resins include C18, C8, phenyl, SDB-L sorbents resins, and combinations thereof.

Exemplary polymeric resins that can be used to absorb volatile organic compounds (such as styrene vapor) include, for example, STRATA-X® polymeric resins (Phenomenex), Ainberlite polymeric resins (Sigma-Aldrich), DOWEX™ polymeric resins or AMBERJET™ polymeric resins (The Dow Chemical Company), Macronet™ polymeric resins, PuroSorb™ polymeric resins, or Chromalite® resins (Puro-Lite), etc. The surface area and pore size distribution of the resin should suitable for absorbing volatile organic compounds. Because a polymeric resin is made with few functional groups (often it is the single dominant functional group which gives the surface its adsorption characteristics), one can ascertain the affinity (e.g., Hanson solubility parameter) and predict the adsorption capacity based on thermodynamics. Various studies have shown that adsorption capacities of a variety of solutes, and polymeric resins can be correlated with solubility parameters.

Other materials suitable for absorbing styrene vapor include activated carbon and cellulosic materials. For example, the cotton burrs disclosed in US 2002/0151622 as cellulosic materials can be used in the present invention to absorb volatile organic compounds.

The detection material also comprises a detectable marker that causes a color change in the presence of styrene. One exemplary detectable marker is 4-nitrobenzyl-pyridine (NBP). The unpaired electron of NBP reacts with the oxirane ring of styrene oxide to yield a blue chromophore.

If desired, the color change of the detectable material can be determined by a quantitative assay, such as by spectrophotometry. The color change may also be determined qualitatively. Sometimes, the color change would be apparent to an observer.

If desired, the activity of the candidate protein can be compared with a control. A control can be a parallel sample comprising a cinnamic acid decarboxylase whose activity has been characterized (e.g., a wild type cinnamic acid decarboxylase, or a specific mutant cinnamic acid decarboxylase that serves as the base sequence for further mutations). Alternatively, a control may be a pre-determined threshold value, or a value that is present in a database (e.g., a table, electronic database, spreadsheet, etc.).

Figure 13:
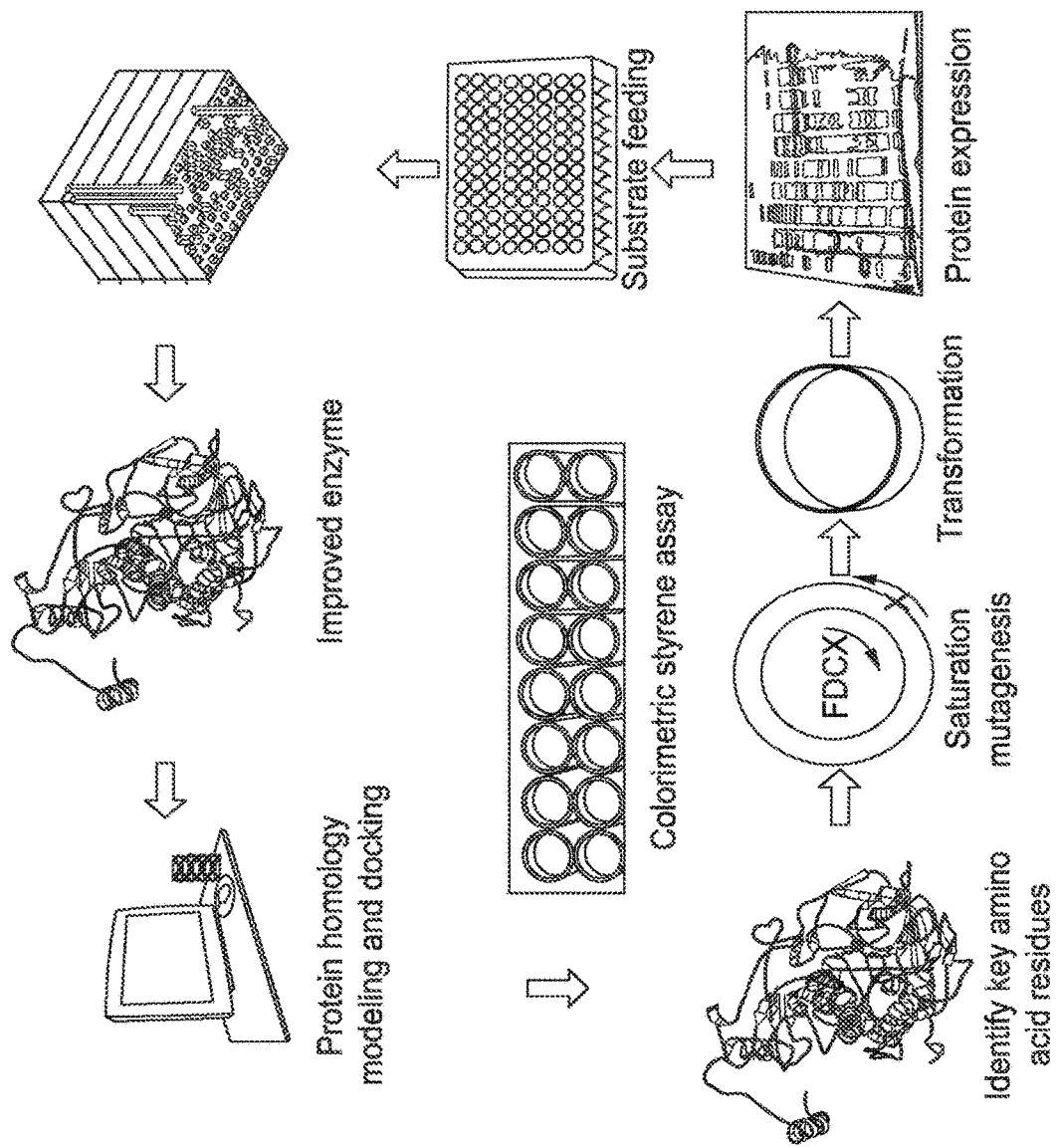
FIG. 13 depicts the process of random mutagenesis to create FDC mutants, and the high throughput colorimetric screening of FDC1 mutants.

As shown in FIG. 13, the screening assay can be conducted for more than one round, and can be combined with computer modeling to rationally design and improve the activities of cinnamic acid decarboxylases.

In certain embodiments, mutated cinnamic acid decarboxylase capable of converting converting trans-cinnamic acid to styrene, or converting coumaric acid to 4-hydroxystyrene, can be screened by the method described herein. In certain embodiments, the candidate protein being screened can be a fusion protein comprising a mutated cinnamic acid decarboxylase.

4. Recombinant Production and Purification of Cinnamic Acid Decarboxylase

In another aspect, the subject technology also provides a method of recombinant production and purification of cinnamic acid decarboxylase, such as FDC. In particular, the subject technology provides a method of isolating a recombinantly produced cinnamic acid decarboxylase, comprising: (i) providing a bacterial host comprising a nucleic acid that encodes a cinnamic acid decarboxylase operably linked to a promoter sequence; (ii) culturing the bacterial host in a culture medium to express the cinnamic acid decarboxylase in the host cell, therein the host cell is cultured at a temperature that is from about 10° C. to about 25° C.; and (iii) isolating the cinnamic acid decarboxylase from the host cell, wherein the isolation is conducted in an anaerobic environment.

In some embodiments, culturing the bacterial host cell (e.g., E. coli) at lower temperature can significantly promote the correct folding of the recombinantly produced cinnamic acid decarboxylase, such as FDC1. Lowering the culturing temperature also facilitates the conversion of aggregated or misfolded protein to a functionally soluble form. In certain embodiments, the cell culture is grown at a temperature of about 10, 11, 12, 13, 14, 15, 16, 17, 18, 19, 20, 21, 22, 23, 24, or 25° C.

Reducing agents, such as Tris(2-carboxyethyl) phosphine (TCEP) or β-mercaptoethanol, can also be used in the method of recombinantly producing cinnamic acid decarboxylase, such as FDC1. Accordingly, one or more buffer solutions used for isolating the cinnamic acid decarboxylase may comprise a reducing agent, such as TCEP at a concentration of about 5 mM, 10 mM, 15 mM, 20 mM, 25 mM, 30 mM, 35 mM, 40 mM, 45 mM, 50 mM, or 100 mM; or β-mercaptoethanol at a concentration of about 5 mM, 10 mM, 15 mM, 20 mM, 25 mM, 30 mM, 35 mM, 40 mM, 45 mM, 50 mM, or 100 mM; and a combination thereof.

Samples and cell extracts containing the recombinant cinnamic acid decarboxylase (such as FDC1) maintained in an anaerobic environment also contain cinnamic acid decarboxylase activity.

The recombinantly produced cinnamic acid decarboxylase (such as FDC1) maintains cinnamic acid decarboxylase activity in the presence of metal ions. Suitable metal ions include, e.g., calcium, zinc, magnesium, iron, manganese ion, or a combination thereof. The metal ion may be present at a concentration of from about 0.1 mM to about 100 mM, such as about 0.1 mM, about 0.2 mM, about 0.5 mM, about 1 mM, about 2 mM, about 5 mM, about 10 mM, about 15 mM, about 20 mM, about 25 mM, about 30 mM, about 40 mM, about 50 mM, about 60 mM, about 70 mM, about 80 mM, about 90 mM, about 100 mM; from about 0.1 mM to about 50 mM, from about 0.1 mM to about 25 mM, from about 0.1 mM to about 20 mM, from about 0.1 mM to about 10 mM, from about 1 mM to about 50 mM, from about 1 mM to about 25 mM, from about 1 mM to about 20 mM, from about 1 mM to about 15 mM, or from about 1 mM to about 10 mM. Preferably, the metal ion is an alkaline earth metal ion, or a transitional metal ion.

The purified cinnamic acid decarboxylase described herein is suitable for crystallization.

5. Preparation of Crystalline Form of Cinnamic Acid Decarboxylase.

To gain insight into the structure of cinnamic acid decarboxylase, a method to crystallize this protein was developed. Traditionally, hanging drop and sitting drop vapor diffusion methods are used for crystallization. Both methods require a closed system, that is, the system must be scaled off from the outside using an airtight container or high-vacuum grease between glass surfaces.

The subject technology provides a method of crystallizing a cinnamic acid decarboxylase, the method comprising (a) providing a cinnamic acid decarboxylase solution at a concentration of from about 1 mg/ml to about 50 mg/ml; (b) mixing the cinnamic acid decarboxylase solution with a reservoir solution at a volume ratio of from about 1:10 to about 10:1; and (c) maintaining the mixture of step (b) at a temperature suitable for the formation of the cinnamic acid decarboxylase crystals.

Preferably, the protein concentration in step (a) is from about 2 mg/ml to about 20 mg/ml, more preferably from about 5 mg/ml to about 10 mg/ml. The volume ratio of the cinnamic acid decarboxylase solution to the reservoir solution is preferably from about 1:5 to about 5:1, more preferably from about 1:2 to about 2:1. Typically, 1 to 2 μl of the cinnamic acid decarboxylase solution (protein concentration at about 5.0 to 10.0 mg/me is mixed with 1 to 2 μl of a reservoir solution in a drop on glass. The mixture is put upside down on a well, containing the reservoir solution (typically about 500 μl) and the system is incubated at a temperature of from about 1° C. to about 20° C., preferably from about 4° C. to about 12° C. Initially, the droplet of protein solution contains an insufficient concentration of precipitant for crystallization, but as water evaporates from the drop and transfers to the reservoir, the precipitant concentration increases to a level for crystallization. Since the system is in equilibrium, these conditions are maintained until the crystallization is complete.

The crystallization of the cinnamic acid decarboxylase can be improved when the protein forms a complex with a small molecule. For example, the small molecule may be added to the protein solution at step (a) or to the protein/reservoir mixture at step (b) to allow the formation of a protein-small molecule complex. Typically, the final concentration of the small molecule in the mixture of step (b) is from about 0.01% (w/v) to about 1% (w/v), preferably from about 0.05% (w/v) to about 0.5% (w/v), more preferably from about 0.08% (w/v) to about 0.2% (w/v).

Suitable small molecules include substrates of cinnamic acid decarboxylase (e.g. trans-cinnamic acid) and its analogs, such as 3-hydroxyl cinnamic acid, ferulic acid, 2-methylcinnamic acid, 4-hydroxy-cinnamic acid, 3,4-dimethoxy-cinnamic acid, 2,5-dimethoxy-cinnamic acid, and combinations thereof.

The crystallization method can be further improved by including one or more additives in the solution, such as $MnCl_2$ at a concentration of from about 0.001M to about 0.1M, preferably from about 0.005M to about 0.02M; polyvinylpyrrolidone K15 at a concentration of from about 0.1% (w/v) to about 2.5% (w/v), preferably from about 0.25% (w/v) to about 1% (w/v); Non-detergent Sulfobetaine 201 (NDSB-201, $C_8H_{11}NO_3S$) at a concentration of from about 0.02M to about 1M, preferably from about 0.1M to about 0.3M; benzamidine hydrochloride at a concentration of from about 0.2% (w/v) to about 10% (w/v), preferably from about 1% (w/v) to about 3% (w/v); all concentrations being measured in the protein-reservoir mixture of step (b).

E. Fusion Proteins and Protein Complexes

In another aspect, the subject technology provides a fusion protein comprising: (i) a first domain that comprises a phenylalanine ammonia lyase, and (ii) a second domain that comprises a cinnamic acid decarboxylase. Alternatively, a phenylalanine ammonia lyase and a cinnamic acid decarboxylase can form a protein complex, via non-covalent interaction(s).

The fusion protein or protein complex described herein takes advantage of the "substrate channeling" phenomenon. Substrate channeling refers to a phenomenon in which substrates are efficiently delivered from enzyme to enzyme without equilibration with other pools of the same substrates. The fusion protein or protein complex can channel intermediates between sequential enzymes, and control the flux of substrates into competing branches of the pathway. In effect, this creates local pools of metabolites at high concentrations relative to those found in other areas of the cell.

Any one of the phenylalanine ammonia lyase or cinnamic acid decarboxylase described herein can be used to produce a fusion protein. In certain embodiments, the fusion protein further comprises a linker covalently linking the first domain (PAL) and the second domain (cinnamic acid decarboxylase). The linker preferably comprises one or more amino acid residues (e.g., an amino acid linker or a peptide linker). The amino acid residues of the linker may comprise L-amino acid(s), D-amino acid(s), amino acid analogues, or a combination thereof. Other possible linkers include, e.g., a covalent bond, C1-C6 alkyl, a cycloalkyl such as a cyclopentyl or cyclohexyl, a cycloalkenyl, aryl, or heteroaryl moiety. A linker may also comprise a combination of one or more amino acid(s) with another linking moiety (such as C1-C6 alkyl-, cycloalkyl-(C5, C6), aryl, or heteroaryl moieties).

In certain embodiment, the linker is a peptide linker. The peptide linker may be 1, 2, 3, 4, 5, 6, 7, 8, 9, 10, 11, 12, 13, 14, 15, 16, 17, 18, 19, 20, 21, 22, 23, 24, 25, 30, 35, or 40 amino acid long. Preferably, the length of the linker is from 2 to 15 amino acids.

In certain embodiments, the linker is a glycine/serine linker, i.e., a peptide linker consisting essentially of glycine and serine. In an exemplary embodiment, the linker comprises GS or GSG. In another exemplary embodiment, the linker comprises the Gly-Ser-Gly (GSG) motif, such as GGSG (SEQ ID NO:39), (GS)×3 (SEQ ID NO:40), (GGSG)×2 (SEQ ID NO:41), SGGSGGSGG (SEQ ID NO:42), GGSGGGSGGGSG (SEQ ID NO:43), (GGGGS)×3 (SEQ ID NO:44), as described in Table 1 below.

TABLE 1

Glycine/Serine Linkers

| Linker | Amino Acid Sequence |
|---|---|
| GS Linker | GS |
| GSG Linker | GSG |
| SEQ ID NO: 39 | GGSG |
| SEQ ID NO: 40 | GSGSGS |
| SEQ ID NO: 41 | GGSGGGSG |
| SEQ ID NO: 42 | SGGSGGSGG |
| SEQ ID NO: 43 | GGSGGGSGGGSG |
| SEQ ID NO: 44 | GGGGSGGGGSGGGGS |

Fusion proteins described herein can be produced using techniques well known in the art. For example, when the linker is a peptide linker, the fusion protein can be produced using standard recombinant DNA technology. Other types of linker can be attached by, e.g., standard conjugation techniques. See, e.g., Heimanson et al., Bioconjugate Techniques, 2nd Ed., 2008; Academic Press.

The fusion protein may comprise multiple units of phenylalanine ammonia lyase and cinnamic acid decarboxylase. In certain embodiments, the fusion protein can be PAL-FDC, PAL-FDC-PAL-FDC, or PAL-FDC-FDC-PAL, etc. For example, the FDC can be at the 5' terminal of the DNA encoding the fusion protein, and the PAL can be at the 3' terminal of the DNA encoding the fusion protein. In another example, the PAL can be at the 5' terminal of the DNA encoding the fusion protein, and the FDC can be at the 3' terminal of the DNA encoding the fusion protein. In addition, the cinnamic acid decarboxylase unit of the fusion protein can be wild type (WT) or mutant proteins, such as any of the mutant FDC proteins described above. For example, the fusion protein can be PAL-FDC(WT) or PAL-FDC(K190E).

Alternatively or in addition, the phenylalanine ammonia lyase and the cinnamic acid decarboxylase can form a protein complex, via non-covalent interaction(s). A "protein complex" refers to an association of more than one protein. The proteins of the complex may be associated by e.g., functional, stereochemical, conformational, biochemical, or electrostatic association. It is intended that the term encompass associations of any number of proteins.

Alternatively, or in addition, the phenylalanine ammonia lyase and the cinnamic acid decarboxylase can be modified to include an "interacting moiety." For example, one enzyme can comprise an antibody, and the other can comprise a cognate antigen; or one enzyme can comprise a ligand, and the other can comprise a cognate receptor; or one enzyme can comprise biotin, and the other can comprise avidin, etc. The interacting moieties can interact with each other, thereby brining the two enzymes in proximity to each other. Any pairs of interacting moieties can be used.

F. Host Cells and Cell Cultures

Methods described herein use host cells to produce styrene. A host cell can be derived from a bacterium, fungus (e.g., yeast), protist (e.g., algae), plant, insect, amphibian, fish, reptile, bird, mammal (including human), or can be a hybridoma cell. Host cells can be unmodified cells or cell lines, or cell lines which have been genetically modified (e.g., to facilitate production of styrene). In some embodiments, the host cell is a cell line that has been modified to allow for growth under desired conditions, such as at a lower temperature.

As described herein, suitable host cells that express phenylalanine ammonia lyase or cinnamic acid decarboxylase can be cultured, sometimes in large scale (i.e., about 1 liter, about 10 liters, at les 100 liters, etc.), to produce commercially useful amounts of styrene or other compounds downstream from styrene (compounds which will result from further processing of styrene in these microorganisms via enzymatic or biological pathways).

The methods described herein can be applied to any size of cell culture flask and/or bioreactor. For example, the methods can be applied in bioreactors or cell cultures of 1 L, 10 L, 30 L, 50 L, 100 L, 150 L, 200 L, 300 L, 500 L, 1000 L, 2000 L, 3000 L, 4000 L, 5000 L, 10,000 L or larger.

The pH of the liquid medium can either be kept constant, that is to say regulated during the culturing period, or not. The cultures can be grown batchwise, semibatchwise or continuously. Nutrients can be provided at the beginning of the fermentation or fed in semi-continuously or continuously.

Media components include, e.g., buffer, amino acid content, vitamin content, salt content, mineral content, serum content, carbon source content, lipid content, nucleic acid content, hormone content, trace element content, ammonia content, co-factor content, indicator content, small molecule content, hydrolysate content and enzyme modulator content.

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981; the entirety of which is hereby incorporated herein by reference). These media which can be employed in accordance with the subject technology usually comprise one or more carbon sources, nitrogen sources, inorganic salts, vitamins and/or trace elements.

Carbon sources for use in the culture media of the host cells comprise sugars, such as mono-, di- or polysaccharides. Examples of carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

In an embodiment, the inorganic salt compounds that are present in the culture media comprise about one of the chloride, phosphorus and sulfate salts of calcium, magnesium, sodium, cobalt, molybdenum, potassium, manganese, zinc, copper or iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing derivatives of styrene.

Phosphoric acid, potassium dihydrogenphosphate or dipotassium hydrogenphosphate or the corresponding sodium-containing salts may be used as sources of phosphorus.

Other components that may be added to the culture medium in order to keep the metal ions in solution comprise dihydroxyphenols such as catechol or protocatechuate and organic acids such as citric acid.

The culture medium may comprise one or more metal ions, such as calcium, zinc, magnesium, iron, manganese ion, and a combination thereof. The metal ion may be present at a concentration of from about 0.1 mM to about 100 mM, such as about 0.1 mM, about 0.2 mM, about 0.5 mM, about 1 mM, about 2 mM, about 5 mM, about 10 mM, about 15 mM, about 20 mM, about 25 mM, about 30 mM, about 40 mM, about 50 mM, about 60 mM, about 70 mM, about 80 mM, about 90 mM, about 100 mM; from about 0.1 mM to about 50 mM, from about 0.1 mM to about 25 mM, from about 0.1 mM to about 20 mM, from about 0.1 mM to about 10 mM, from about 1 mM to about 50 mM, from about 1 mM to about 25 mM, from about 1 mM to about 20 mM, from about 1 mM to about 15 mM, or from about 1 mM to about 10 mM. Preferably, the metal ion is an alkaline earth metal ion, or a transitional metal ion.

The fermentation media used according to the subject technology for culturing the host cells of the subject technology usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case. Information on the culture of media can be found in the textbook "Applied Microbial. Physiology, A Practical Approach" (Editors P. M. Rhodes, P. F. Stanbury, IRL Press (1997) pp. 53-73; the entirety of which is hereby incorporated herein by reference). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The temperature of the cell culture will be selected based primarily on the range of temperatures at which the cell culture remains viable, at which a high level of polypeptide is produced, at which misfolding and/or aggregation of the polypeptide are reduced, at which the polypeptide exhibits a more extensive or otherwise more desirable post-translational modification (e.g., glycosylation, phosphorylation, etc.), or any combination of these or other factors deemed important by the practitioner. In general, most host cells grow well and can produce high levels or protein or polypeptide within a range of about 15° C. to 45° C. In certain embodiments, the cell culture is grown at a temperature of about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45° C. at one or more times during the cell culture process. Those of ordinary skill in the art will be able to select appropriate temperature or temperatures in which to grow cells, depending on the needs of the cells and the production requirements.

Furthermore, the culture may be subjected to one or more temperature shifts during the course of the culture. When shifting the temperature of the culture, the temperature shift may be relatively gradual. For example, it may take several hours or days to complete the temperature change. Alternatively, the temperature shift may be relatively abrupt. The temperature may be steadily increased or decreased during the culture process. Additionally or alternatively, the temperature may be increased or decreased by discrete amounts at various times during the culture process. The subsequent temperature(s) or temperature range(s) may be lower than or higher than the initial or previous temperature(s) or temperature range(s). One of ordinary skill in the art will understand that multiple temperature shifts are encompassed by the subject technology. For example, the temperature may be shifted once (either to a higher or lower temperature or temperature range), the cells maintained at this temperature or temperature range for a certain period of time, after which the temperature may be shifted again to a new temperature or temperature range, which may be either higher or lower than the temperature or temperature range of the previous temperature or temperature range. The temperature of the culture after each discrete shift may be constant or may be maintained within a certain range of temperatures.

As with the initial temperature or temperature range, the temperature or temperature range of the cell culture after the temperature shift(s) is generally selected based primarily on the temperature(s) at which the cell culture remains viable, the range in which a high level of protein is produced. For example, a bacterial cell culture may be grown at 37° C. after seeding to encourage cell proliferation; once the cells reach a desired density, the expression of a recombinant protein is induced, and the temperature is shifted to 25° C. to reduce misfolding or aggregation of the recombinantly produced protein.

Anaerobic condition is also contemplated. Exemplary anaerobic bacterial hosts include, e.g., *Bacteroids, Fusobacterium, Clostridium, Propionibacterium, Lactobacillus, Peptococcus, Peptostreptococcus* and *Veillonella*.

If desired, the styrene produced in the host cells can further undergo enzymatic reaction and be converted to a downstream derivative of styrene such as toluene, xylene, polystyrene, ABS, styrene-butadiene (SBR) rubber, styrene-butadiene latex, SIS (styrene-isoprene-styrene), S-EB-S (styrene-ethylene/butylene-styrene), styrene-divinylbenzene (S-DVB), styrene-acrylonitrile resin (SAN) and unsaturated polyesters and the like. Thus, in some embodiments the host cells of the subject technology can convert certain percentage of the styrene produced to a downstream derivative of styrene. For example, the host cell can convert about 5% of the styrene to a downstream derivative, or from about 5% to about 15% of the styrene to a downstream derivative, or from about 10% to about 25% of the styrene to a downstream derivative, or from about 20% to about 35% of the styrene to a downstream derivative, or from about 30% to about 45% of the styrene to a downstream derivative, or from about 40% to about 55% of the styrene to a downstream derivative, or from about 50% to about 65% of the styrene to a downstream derivative, or from about 60% to about 75% of the styrene to a downstream derivative, or from about 70% to about 85% of the styrene to a downstream derivative, or from about 80% to about 95% of the styrene to a downstream derivative.

1. Microbial Hosts

Microorganisms useful for the production of styrene may include bacteria, such as enteric bacteria (*Escherichia*, and *Salmonella* for example), *Bacillus, Acinetobacter, Actinomycetes* (such as *Streptomyces*), *Corynebacterium, Methanotrophs* (such as *Methylosinus*), *Methylomonas, Rhodococcus, Pseudomona, Cyanobacteria* (such as *Rhodobacterand, Synechocystis*), *Klebsiella, Pantoea, Corynebacterium, Clostridium*, etc.; yeasts, such as *Saccharomyces, Zygosaccharomyces, Kluyveromyces, Candida, Hansenula, Debaryomyces, Mucor, Pichia* and *Torulopsis*; filamentous fungi such as *Aspergillus, Arthrobotrys*; algae, etc.

Although any of the above mentioned microorganisms would be useful in the production of styrene, preferred are mutant strains of bacteria that over-produce phenylalanine. "Phenylalanine overproducing" strain is a mutant microbial strain that produces higher level of phenylalanine as compared to that of the wild-type strain that does not have the mutation. Phenylalanine is naturally present in micro-organisms. However, for an optimal synthesis of styrene a host cell preferably over-produces phenylalanine such that the substrate level does not limit styrene production by the host cell. Methods to increase aromatic amino acid synthesis in a micro-organism are known in the art.

One specific example of an *E. coli* phenylalanine overproducer is the *E. coli* strain NST74 (U.S. Pat. No. 4,681, 852). Others suitable Phenylalanine overproducing strains include, e.g., *Corynebacterium glutamicum* (Ikeda, M. and Katsumata, R. Metabolic engineering to produce tyrosine or phenylalanine in a tryptophan-producing *Corynebacterium glutamicum* strain, Appl. Environ. Microbial. (1992), 58(3), pp. 781-785); *Microbacterium ammoniaphilum* ATCC 10155; *Corynebactrium lillium* NRRL-B-2243, *Brevibacterium divaricatum* NRRL-B-2311; *Arthrobacter citreus* ATCC 11624. Additional suitable phenylalanine overproducing strains can be found, e.g., in Maiti et al, Supra and Metabolic Engineering For Microbial Production Of Aromatic Amino Acids And Derived Compounds, J. Bongaertes et al, Metabolic Engineering vol 3, 289-300, 2001.

The host cell may also be selected for increased resistance against a toxic analogue of an aromatic amino acid (e.g., phenylalanine). For example, mutant micro-organisms can be selected for resistance to toxic (m-fluoro-)analogues of phenylalanine. These insensitive mutants often produce high levels of phenylalanine and tyrosine (GB 1071935; U.S. Pat. No. 3,709,785).

It is also possible to obtain a recombinant host cell with increased phenylalanine production by overexpression of one or more key genes in the biosynthesis of phenylalanine (Ikeda 2003. Amino acid production processes. P. 1-35, in T. Scheper (Ed.), Advances in Biochemical Engineering/Biotechnology, Vol. 79. Springer-Verlag, Berlin Heidelberg).

Standard recombinant DNA methodologies may be used to obtain a nucleic acid that encodes a protein described herein (e.g., phenylalanine ammonia lyase, cinnamic acid decarboxylase, or a fusion protein), incorporate the nucleic acid into an expression vector, and introduce the vector into a host cell, such as those described in Sambrook, et al. (eds), Molecular Cloning; A Laboratory Manual, Third Edition, Cold Spring Harbor, (2001); Ausubel, F. M. et al. (eds.) Current Protocols in Molecular Biology, John Wiley & Sons (1995). A nucleic acid encoding a protein may be inserted into an expression vector or vectors such that the nucleic acids are operably linked to transcriptional and translational control sequences (such as a promoter sequence, a transcription termination sequence, etc.). The expression vector and expression control sequences are generally chosen to be compatible with the expression host cell used.

The expression of proteins in a microbial host described herein can be further improved by codon-optimization. For example, modifying a less-common codon with a more common codon may affect the half-life of the mRNA or alter its structure by introducing a secondary structure that interferes with translation of the message. All or a portion of a coding region can be optimized. In some cases the desired modulation of expression is achieved by optimizing essentially the entire gene. In other cases, the desired modulation will be achieved by optimizing part of but not entire sequence of the gene.

The codon usage of any coding sequence can be adjusted to achieve a desired property, for example high levels of expression in a specific cell type. The starting point for such an optimization may be a coding sequence with 100% common codons, or a coding sequence which contains a mixture of common and non-common codons.

Two or more candidate sequences that differ in their codon usage can be generated and tested to determine if they possess the desired property. Candidate sequences can be evaluated by using a computer to search for the presence of regulatory elements, such as silencers or enhancers, and to search for the presence of regions of coding sequence which could be converted into such regulatory elements by an alteration in codon usage. Additional criteria may include enrichment for particular nucleotides, e.g., A, C, G or U, codon bias for a particular amino acid, or the presence or absence of particular mRNA secondary or tertiary structure. Adjustment to the candidate sequence can be made based on a number of such criteria.

In certain embodiments, the codon optimized nucleic acid sequence can express its protein, at a level which is about 110%, about 150%, about 200%, about 250%, about 300%, about 350%, about 400%, about 450%, or about 500%, of that expressed by nucleic acid sequence that has not been codon optimized.

In addition to the nucleic acid that encodes the protein, the expression vector may additionally carry regulatory sequences that control the expression of the protein in a host cell, such as promoters, enhancers or other expression control elements that control the transcription or translation of the nucleic acid(s). Such regulatory sequences are known in the art (see, e.g., Goeddel, Gene Expression Technology: Methods in Enzymology 185, Academic Press (1990)). It will be appreciated by those skilled in the art that the design of the expression vector, including the selection of regulatory sequences may depend on such factors as the choice of the host cell to be transformed, the level of expression of protein desired, etc.

In addition to sequences encoding the protein and regulatory sequences, the recombinant expression vectors of the subject technology may carry additional sequences, such as sequences that regulate replication of the vector in host cells (e.g., origins of replication) and selectable marker genes.

The expression vector(s) encoding the protein may be transformed or transfected into a host cell by standard techniques, such as electroporation, calcium-phosphate precipitation, or DEAE-dextran transfection.

Where commercial production of styrene is desired, a variety of fermentation methodologies may be applied. For example, large scale production may be effected by both batch or continuous fermentation.

A classical batch fermentation is a closed system where the composition of the media is set at the beginning of the fermentation and not subject to artificial alterations during the fermentation. Thus, at the beginning of the fermentation the medium is inoculated with the desired microorganism or microorganisms and fermentation is permitted to occur adding nothing to the system. Typically, however, the concentration of the carbon source in a "batch" fermentation is limited and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in the log phase generally are responsible for the bulk of production of end product or intermediate.

A variation on the standard batch system is the Fed-Batch system. Fed-Batch fermentation processes are also suitable in the subject technology and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, T. D.; Biotechnology: A Textbook of Industrial Microbiology, 2nd ed.; Sinauer Associates: Sunderland, Mass., 1989; or Deshpande, M. V. Appl. Biochem. Biotechnol. 36:227, (1992).

Commercial production of styrene may also be accomplished with continuous fermentation. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in their log phase of growth.

Continuous fermentation allows for modulation of any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by the medium turbidity, is kept constant. Continuous systems strive to maintain steady state growth conditions and thus the cell loss due to the medium removal must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

2. Plant Hosts

Plant cells may also be used as hosts for producing styrene. Preferred plant hosts will be any variety that support a high expression level of phenylalanine ammonia lyase and/or cinnamic acid decarboxylase. Suitable green plants will include, e.g., soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa*, L), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include, e.g., commercially significant hosts such as *Spirulina, Haemotacoccus*, and *Dunalliela*. Suitable plants also include biofuel, biomass, and bioenergy crop plants. Exemplary plants include *Arabidopsis thaliana*, lice (*Oryza sativa*), switchgrass (*Panicum vigratum*), *Brachypodium* spp, *Brassica* spp., and *Crambe abyssinica*.

In some embodiments, the plant cell is an *Arabidopsis* plant cell, a tobacco plant cell, a *petunia* plant cell, or a cell from an oilseed crop (including, e.g., a soybean plant cell, a canola plant cell, a rapeseed plant cell, a palm plant cell, a sunflower plant cell, a cotton plant cell, a corn plant cell, a peanut plant cell, a flax plant cell, a sesame plant cell, etc.).

Suitable host cells can be genetically engineered to express phenylalanine ammonia lyase and cinnamic acid decarboxylase. For example, nucleic acid encoding phenylalanine ammonia lyase or cinnamic acid decarboxylase can be operably linked to promoters capable of directing expression of a protein in the desired tissues at the desired stage of development. Any suitable promoter and/or terminator capable of inducing expression of a coding region may be used. Some suitable examples of promoters and terminators include those from nopaline synthase (nos), octopine synthase (ocs) and cauliflower mosaic virus (CaMV) genes.

One type of efficient plant promoter that may be used is a high level plant promoter. High level plant promoters that may be used in the subject technology include the promoter of the small subunit (ss) of the ribulose-1,5-bisphosphate carboxylase for example from soybean (Berry-Lowe et al., J. Molecular and App. Gen., 1:483-498) (1982)), and the promoter of the chlorophyll a/b binding protein. These two promoters are known to be light-induced in plant cells (see, for example, Genetic Engineering of Plants, an Agricultural Perspective, A. Cashmore, Plenum, N.Y. (1983), pages 29-38); Coruzzi, G. et al., The Journal of Biological Chemistry, 258: 1399 (1983), and Dunsmuir, P. et al., Journal of Molecular and Applied Genetics, 2:285 (1983)).

Standard recombinant DNA methodologies may be used to obtain a nucleic acid that encodes a protein described herein, incorporate the nucleic acid into an expression vector and introduce the vector into a host cell. The choice of vector depends upon the method that will be used to transform host plants. The skilled artisan is well aware of the genetic elements that must be present on the plasmid vector in order to successfully transform, select and propagate host cells containing the vector. The skilled artisan will also recognize that different independent transformation events will result in different levels and patterns of expression (Jones et al., EMBO J. 4:2411-2418) (1985); De Almeida et al., Mol. Gen. Genetics 218:78-86) (1989)), and thus that multiple events must be screened in order to obtain lines displaying the desired expression level and pattern. Such screening may be accomplished by Southern analysis of DNA blots (Southern, J. Mol. Biol. 98, 503, (1975)). Northern analysis of mRNA expression (Kroczek, J. Chromatogr. Biomed. Appl., 618 (12):133-145) (1993)), Western analysis of protein expression, or phenotypic analysis.

The expression of proteins in a plant host described herein can be further improved by codon-optimization, as described above. In certain embodiments, the codon optimized nucleic acid sequence can express its protein, at a level which is about 110%, about 150%, about 200%, about 250%, about 300%, about 350%, about 400%, about 450%, or about 500%, of that expressed by nucleic acid sequence that has not been codon optimized.

The subject technology also provides transgenic host cells or host cells that have been transformed with one or more of nucleic acids disclosed herein. The nucleic acid molecule can be stably integrated into the genome of the cell, or the nucleic acid molecule can also be present as an extrachromosomal molecule. Such an extrachromosomal molecule can be auto-replicating. Transformed cells, tissues, or subjects are understood to encompass not only the end product of a transformation process, but also transgenic progeny thereof.

Introduction of a nucleic acid of the subject technology into a plant cell can be performed by a variety of methods known to those of ordinary skill in the art including, but not limited to, insertion of a nucleic acid sequence of interest into an *Agrobacterium rhizogenes* Ri or *Agrobacterium tumefaciens* Ti plasmid, microinjection, electroporation, or direct precipitation. By way of providing an example, in some embodiments, transient expression of a nucleic acid sequence or gene of interest can be performed by agro-infiltration methods. In this regard, a suspension of *Agrobacterium tumefaciens* containing a nucleic acid sequence or gene of interest can be grown in culture and then injected into a plant by placing the tip of a syringe against the underside of a leaf while gentle counter-pressure is applied to the other side of the leaf. The Agro bacterium solution is then injected into the airspaces inside the leaf through stomata. Once inside the leaf, the Agro bacterium transforms the gene of interest to a portion of the plant cells where the gene is then transiently expressed.

As another example, transformation of a vector or nucleic acid of interest into a plant cell can be performed by particle gun bombardment techniques. In this regard, a suspension of plant embryos can be grown in liquid culture and then bombarded with plasmids or nucleic acids that are attached to gold particles, wherein the gold particles bound to the plasmid or nucleic acid of interest can be propelled through the membranes of the plant tissues, such as embryonic tissue. Following bombardment, the transformed embryos can then be selected using an appropriate antibiotic to generate new, clonally propagated, transformed embryogenic suspension cultures.

For additional guidance regarding methods of transforming and producing transgenic plant cells, see U.S. Pat. Nos. 4,459,355; 4,536,475; 5,464,763; 5,177,010; 5,187,073; 4,945,050; 5,036,006; 5,100,792; 5,371,014; 5,478,744; 5,179,022; 5,565,346; 5,484,956; 5,508,468; 5,538,877; 5,554,798; 5,489,520; 5,510,318; 5,204,253; 5,405,765; EP Nos. 267,159; 604,662; 672,752; 442,174; 486,233; 486, 234; 539,563; 674,725; and, International Patent Application Publication Nos. WO 91/02071 and WO 95/06128.

3. Reducing Styrene Toxicity

In another aspect, the subject technology provides a host cell comprising: (a) a recombinantly expressed phenylalanine ammonia lyase; (b) a recombinantly expressed cinnamic acid decarboxylase; and (c) a recombinantly expressed membrane-bound transporter.

One significant problem that limits the bioproduction of styrene is the toxicity of styrene to host cells. The accumulation of hydrophobic aromatics within the cytoplasmic membrane is known to disrupt its integrity. To reduce styrene toxicity and enhance production, a membrane-bound transporter (e.g. an efflux pump) can be introduced into the host cell to remove organic solvent from the cell. Accordingly, the host cell displays a tolerant phenotype towards hydrophobic solvents.

In one embodiment, the membrane-bound transporter can be an ABC-transporters (ATP-binding cassette transporters), which are transmembrane proteins that utilize the energy of adenosine triphosphate (ATP) hydrolysis to carry out certain biological processes including translocation of various substrates across membranes and nontransport-related processes such as translation of RNA and DNA repair. They transport a wide variety of substrates across extra- and intracellular membranes, including metabolic products, lipids and sterols, and drugs. Proteins are classified as ABC transporters based on the sequence and organization of their ATP-binding cassette (ABC) domain(s).

Provided herein are host cells that express an ABC-transporter, which allows the host cells to secrete styrene into the culture medium. In particular, the ABC-transporter is a solvent-resistant pump. Solvent-resistant pumps conferring resistance or tolerance towards organic solvents have been shown to possess very broad specificity, taking organic compounds that by virtue of their chemical-physical characteristics (e.g., accumulating in the bacterial membrane), such as aromatics, alcohols, alkanes etc., as substrates (Kieboom et al. 1998. J. Biol. Chem. 273:85-91). Aromatic compounds also partition effectively to the cell membrane where they act as substrates for solvent-resistant pumps.

In one embodiment of the subject technology, a host cell comprises a member of the proton-dependent resistance/nodulation/cell division (RND) family of efflux pumps. RND-type efflux pumps belong to the multidrug resistance (MDR) pumps. They have an extremely broad substrate specificity and protect bacterial cells from the actions of antibiotics on both sides of the cytoplasmic membrane. Members of this family have been shown to be involved in export of antibiotics, metals, and oligosaccharides involved in nodulation signalling. RND-type efflux pumps usually function as three-component assemblies spanning the outer and cytoplasmic membranes and the periplasmic space of Gram-negative bacteria. Examples of suitable RND-type efflux pumps for use in a method of the subject technology can be found in Tseng, T. T., Gratwick, K. S., Kollman, J., Park., D., Nies, D. H., Goffeau, A., & Saier Jr., M. H. (1999). J. Mol. Microbial. Biotechnol. 1: 107-125.

In one embodiment, the host cell comprises the solvent resistance pump srpABC of *P. putida* S12 (Isken et al. 1996 J. Bacterial. 178:6056; Kieboom et al. 1998. J. Biol. Chem. 273:85-91). The deduced amino acid sequences of the proteins encoded by the srpABC genes have extensive homology with those of the RND family of efflux pumps. It is composed of three protein components that together span the inner and outer membranes of Gram-negative bacteria: an inner membrane transporter (SrpB analogues), an outer membrane channel (SrpC analogues), and a periplasmic linker protein (SrpA analogues). Dendrograms showing the phylogenetic relationship of SrpA, SrpB, and SrpC to other proteins involved in multidrug resistance are shown in Kieboom et al. (1998 J. Biol. Chem. 273:85-91). The srpABC-encoded proteins show the most homology with those for the mexAB/oprM-encoded multidrug resistance pump found in *Pseudomonas aeruginosa*. SrpA, SrpB, and SrpC are 57.8, 64.4, and 58.5% identical to MexA, MexB, and OprM, respectively. In one embodiment, a host cell comprises an efflux pump consisting of an inner membrane transporter, an outer membrane channel, and a periplasmic linker protein belonging to the RND-family of efflux pumps wherein the proteins show a homology of about 50%, about 55%, about 60%, about 70%, about 80%, about 85%, about 95%, about 98%, about 99%, or even 100% sequence identity to the SrpA, SrpB or SrpC proteins of *P. putida* S12. Any functional equivalents of known solvent efflux pumps that can use an aromatic compound as a substrate can be used.

In one embodiment, the host cell can convert the fermentable carbon substrate into an aromatic amino acid (e.g., phenylalanine), which is subsequently converted into styrene. Once produced, styrene actively transported out of the host cell by an efflux pump, preferably by a member of the proton-dependent resistance/nodulation/cell division (RND) family of efflux pumps, such as srpABC.

The bacterium *P. putida* S12 has also been engineered as a solvent tolerance platform for the biosynthesis of both p-hydroxybenzoate and p-hydroxystyrene (Verhoef et al., 2007, Bioproduction of p-hydroxybenzoate from renewable feed stockby solvent-tolerant *Pseudomonas putida* S12. Journal of Biotechnology 132, 49-56; Verhoef et al., 2009, Bioproduction of p-hydroxystyrene from glucose by the solvent-tolerant bacterium *Pseudomonas putida* S12 in a two-phase water-decanol fermentation. Applied and Environmental Microbiology 75, 931-936). The engineered strain can be used for the bioproduction of styrene. Other hosts may be engineered in a similar fashion to increase tolerance to organic compounds.

G. Harvesting Styrene from Cell Culture

Styrene can be harvested from the cell culture using conventional methods. For example, host cells can be removed by filtration or centrifugation. Oil phase and water phase may be separated by centrifugation or chromatography. Additional adsorption, distillation, and microfiltration techniques may be used to further purify styrene. A general scheme of purification involves removing polymerization inhibitors with alkaline water solution (usually 5-10% NaOH), washing in stilled water, drying and fractional distillation under reduced pressure, microfiltration of the styrene monomer in the gas state, and a combination thereof.

Thus, the subject technology provides an inexpensive biological route to the production of styrene which is useful in a variety of commercial materials including polystyrene, ABS, styrene-butadiene (SBR) rubber, styrene-butadiene latex, SIS (styrene-isoprene-styrene), S-EB-S (styrene-ethylene/butylene-styrene), styrene-divinylbenzene (S-DVB), styrene-acrylonitrile resin (SAN) and unsaturated polyesters. These materials are used in rubber, plastic, insulation, fiberglass, pipes, automobile and boat parts, food containers, and carpet backing.

H. Biosynthesis of Styrene

Typically, styrene can be produced by incubating a substrate described herein (such as glucose, phenylalanine, or trans-cinnamic acid) with the host cell comprising any cinnamic acid decarboxylase described herein or any fusion proteins described herein. The concentration of glucose in the incubation typically is from about 0.02% to about 3%, preferable from about 0.05% to about 1.5%, more preferably from about 0.1% to about 1%. The concentration of trans-cinnamic acid in the incubation typically is from about 0.02% to about 0.5%, preferable from about 0.05% to about 0.2%. The concentration of phenylalanine in the incubation typically is from about 0.02% to about 0.5%, preferable from about 0.05% to about 0.2%. In one embodiment, following the addition of the substrate, the host cells is cultured continuously for about 10 to about 72 hours, preferably from about 15 to about 36 hours, at a temperature of from about 16° C. to about 37° C., preferably from 22° C. to about 30° C.

Based on the above, the subject technology provides a method of producing styrene, the method comprising (a) contacting a host cell with a fermentable carbon substrate, the host cell comprising a fusion protein as described above; and (b) culturing the host cell in a culture medium for a time sufficient to produce styrene.

The subject technology also provides a method of producing styrene, the method comprising (a) contacting a host cell with a fermentable carbon substrate, the host cell comprising (i) a phenylalanine ammonia lyase; and (ii) a mutant cinnamic acid decarboxylase as described above; and (b) culturing the host cell in a culture medium for a time sufficient to produce styrene.

The subject technology also provides a host cell comprising: (a) a recombinantly expressed phenylalanine ammonia lyase; (b) a recombinantly expressed cinnamic acid decarboxylase; and (c) a recombinantly expressed membrane-bound transporter. Accordingly, the subject technology also provides a method for the production of styrene, the method comprising: (a) contacting the above host cell with a fermentable carbon substrate; and (b) culturing the host cell in a culture medium for a time sufficient to produce styrene.

In traditional methods, styrene biosynthesis is accomplished in closed containers to prevent styrene from evaporating from the container. This closed system cannot maintain the facultative anaerobic conditions (optimal conditions) for a biological system to produce styrene. Thus, with the traditional method, styrene product accumulates in the closed container and the styrene biosynthesis eventually stops due to the toxicity effect imposed by styrene on the biosynthetic system (e.g. a host cell). Surprisingly, the inclusion of an absorbing material to remove the styrene vapor from the biosynthesis process not only enables a reliable detection of the styrene product (e.g. by the method of screening FDC mutant activities as described above), but also improves the yield of styrene biosynthesis.

Accordingly, the subject technology also provides a method for producing styrene, the method comprising: (a) contacting a host cell with a fermentable carbon substrate, the host cell comprising (i) a phenylalanine ammonia lyase; and (ii) a cinnamic acid decarboxylase; and (b) culturing the host cell in a culture medium for a time sufficient to produce styrene, wherein the vapor of the styrene product is absorbed by an absorbing material.

In this aspect, the phenylalanine ammonia lyase and the cinnamic acid decarboxylase may include both wild type proteins and mutant proteins. For example, the cinnamic acid decarboxylase may be a mutant FDC protein as described above. In addition, the phenylalanine ammonia lyase and the cinnamic acid decarboxylase may be present as separate proteins or as a fusion protein, such as the PAL-FDC(WT) or PAL-FDC(K190E) fusion proteins described above.

Figure 19:
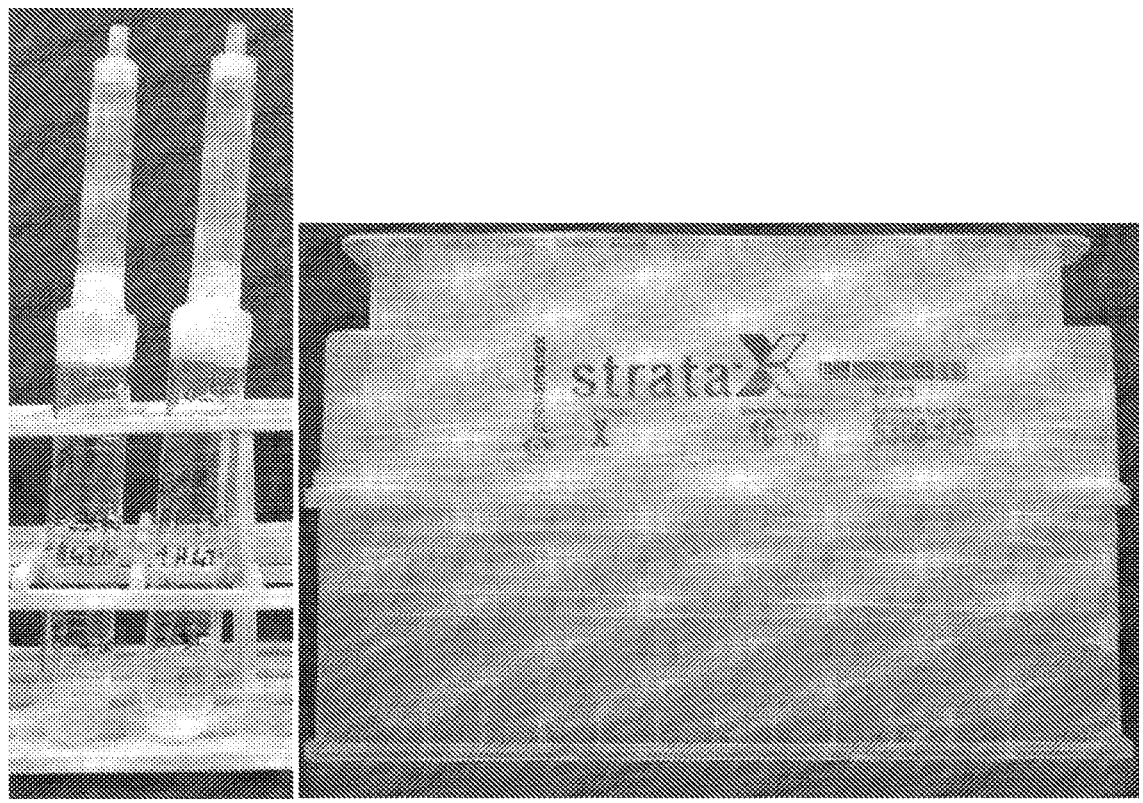
FIG. 19 shows the use of STRATA-X® resin on top of a culture tube (left) or on top of a 96-well culture plate (right).

In one embodiment, the styrene vapor is absorbed by a polymeric resin that is capable of absorbing organic molecules, while air is allowed to flow freely into the biosynthesis system (e.g. a host cell). Any absorbing material used in the high-throughput screening process for cinnamic acid decarboxylase activity described above can also be employed in the styrene biosynthesis process with similar devices (FIG. 19). For example, STRATA-X column (containing reverse phase polymeric resin) can be used to absorb the styrene vapor produced from a host cell (thus reducing toxicity to the host cell), while allowing oxygen to pass through the resin to maintain facultative anaerobic conditions for cell growth. Typically, this method allows styrene to be produced at level of greater than 1 g/L.

All the method of producing styrene described above, including the method involving a fusion protein, the method involving mutant cinnamic acid decarboxylase, the method involving membrane-bound transporter, and the method involving removal of styrene vapor by an absorbing material, can also be used to produce 4-hydroxystyrene. In one embodiment, tyrosine or coumaric acid or both can be used as substrate in the methods described above to produce 4-hydroxystyrene.

The capability to construct a fusion protein and to rapidly examine cinnamic acid decarboxylase activity in a large number of samples allows for simultaneously screening the activities of the PAL and cinnamic acid decarboxylase units in the fusion protein, such that an improved overall styrene yield can be achieved. This process is advantageous over the process of examining the PAL and cinnamic acid decarboxylase activities separately before building a fusion protein.

Accordingly, the subject technology provides a method for simultaneously screening phenylalanine ammonia lyase and cinnamic acid decarboxylase activities, the method comprising: (a) providing a fusion protein comprising: (i) a first domain comprising a phenylalanine ammonia lyase, and (ii) a second domain comprising a cinnamic acid decarboxylase; (b) mixing the fusion protein with a substrate under a condition that allows the fusion protein to convert the substrate to a product; and (c) detecting the amount of the remaining substrate, or the amount of the product, or both.

In one embodiment, the subject technology also provides a method for simultaneously screening phenylalanine ammonia lyase and cinnamic acid decarboxylase activities, the method comprising: (a) providing a fusion protein comprising: (i) a first domain comprising a phenylalanine ammonia lyase, and (ii) a second domain comprising a cinnamic acid decarboxylase; (b) providing a substrate selected from the group consisting of phenylalanine, trans-cinnamic acid, tyrosine, coumaric acid, and combinations thereof; (c) incubating the fusion protein and the substrate under a condition that allows the fusion protein to convert the substrate to a product selected from the group consisting of styrene, 4-hydroxystyrene, and combination thereof; and (d) detecting the amount of the remaining substrate, or the amount of the product, or both.

The fusion protein may be prepared using any of the above-described PALs and cinnamic acid decarboxylases, such as PAL-FDC or PAL-FDC(K190E). Typically, a substrate (such as phenylalanine or trans-cinnamic acid) is mixed with the fusion protein, and the activities of the PAL and cinnamic acid decarboxylase in the fusion protein can be simultaneously detected by measuring the amount of the remaining substrate, or the amount of the product, or both. For example, when phenylalanine is mixed with the fusion protein as substrate, the amount of trans-cinnami acid and styrene as products can be measured. In this example, the concentration of cinnamic acid reflects both its production from phenylalanine (by PAL) and its conversion to styrene (by cinnamic acid decarboxylases), and the concentration of styrene reflects the overall styrene production by the fusion protein from any substrate (FIG. 18). Similarly, when trans-cinnamic acid is mixed with the fusion protein for conversion to styrene, both the remaining amount of trans-cinnamic acid substrate and the amount of styrene product can be measured.

In one embodiment, the simultaneously screening for phenylalanine ammonia lyase and cinnamic acid decarboxylase activities can be performed under similar conditions used for the high-throughput screening assays for cinnamic acid decarboxylase activity described herein. In an exemplary embodiment, the detection of styrene comprises exposing the mixture of the fusion protein and the substrate to a polymeric resin that absorbs styrene vapor. Suitable resins include hydrophobic resins, such as C18, C8, phenyl, SDB-L sorbents resins, and combinations thereof.

Examples

The subject technology is further defined in the following Examples. It should be understood that these Examples, while indicating preferred embodiments of the subject technology, are given by way of illustration only. From the above discussion and these Examples, one skilled in the art can ascertain the essential characteristics of the subject technology, and without departing from the spirit and scope thereof, can make various changes and modifications of the subject technology to adapt it to various uses and conditions.

Example 1. Recombination Production, Purification, and Characterization of Yeast FDC1

1. Expression of Yeast FDC1 in *E. coli*

Decarboxylation of trans-cinnamic acid (tCA) by ferulic acid decarboxylase (FDC1) is the last step in the styrene biosynthesis pathway to yield styrene. Though it was reported that expression of FDC1 alone is insufficient to convert tCA to styrene (Jiang et al., 2005, Applied and Environmental Microbiology, 71: 2962-2969; Clausen et al., 1994, Gene, 142: 107-112.), more recently, it was reported that expression of FDC1 alone was sufficient to convert tCA to styrene in vivo (McKenna et al., 2011, Metabolic Engineering, 13 (5): 544-554). McKenna speculated that other proteins, like *E. coli* Ubix that is associated with FDC1 in vivo, enable the conversion of tCA to styrene. There is no report that clearly shows that FDC1 alone, without association of any other proteins, is sufficient to convert tCA to styrene.

To examine the activity of purified FDC1 in vitro, an expression vector was constructed and FDC1 was expressed in *E. coli* under various conditions. Plasmid pDEST17-FDC1 was transformed into *E. Coli* strain BL21 (DE3) competent cells. Terrific-broth media supplemented with ampicillin (100 µg/mL) was inoculated with a 1000-time dilution of an overnight culture. The bacteria were cultured at 37° C. until $OD_{600}$ reached 0.8 to 1.0, at which point isopropyl β-D-1-thiogalactopyranoside (IPTG) was added to a final concentration of 0.2 mM, and continued to be cultured for 3 hours at the same temperature. Three different lysis buffers were used to check the expression of FDC 1. Buffer A contained 25 mM potassium phosphate buffer pH 7.5, 500 mM sodium chloride, 10 mM imidazole, 20 mM βME, 0.5 mM PMSF, 10 mM $MgCl_2$, 2 µg/mL DNAse, 2 µg/mL RNAse, and 4 µg/mL lysozyme. Buffer B contained 50 mM potassium phosphate pH buffer 7.0, 1 mM DTT, 50 mM sodium thiosulfate, 20% glycerol, 500 mM NaCl, 10 mM $MgCl_2$, 20 mM imidazole, 2 µg/mL DNAse, 2 µg/mL RNAse, and 4 µg/mL lysozyme. Buffer C was composed of Buffer A containing 50 mM sodium thiosulfate and 20% glycerol.

Figure 2A:
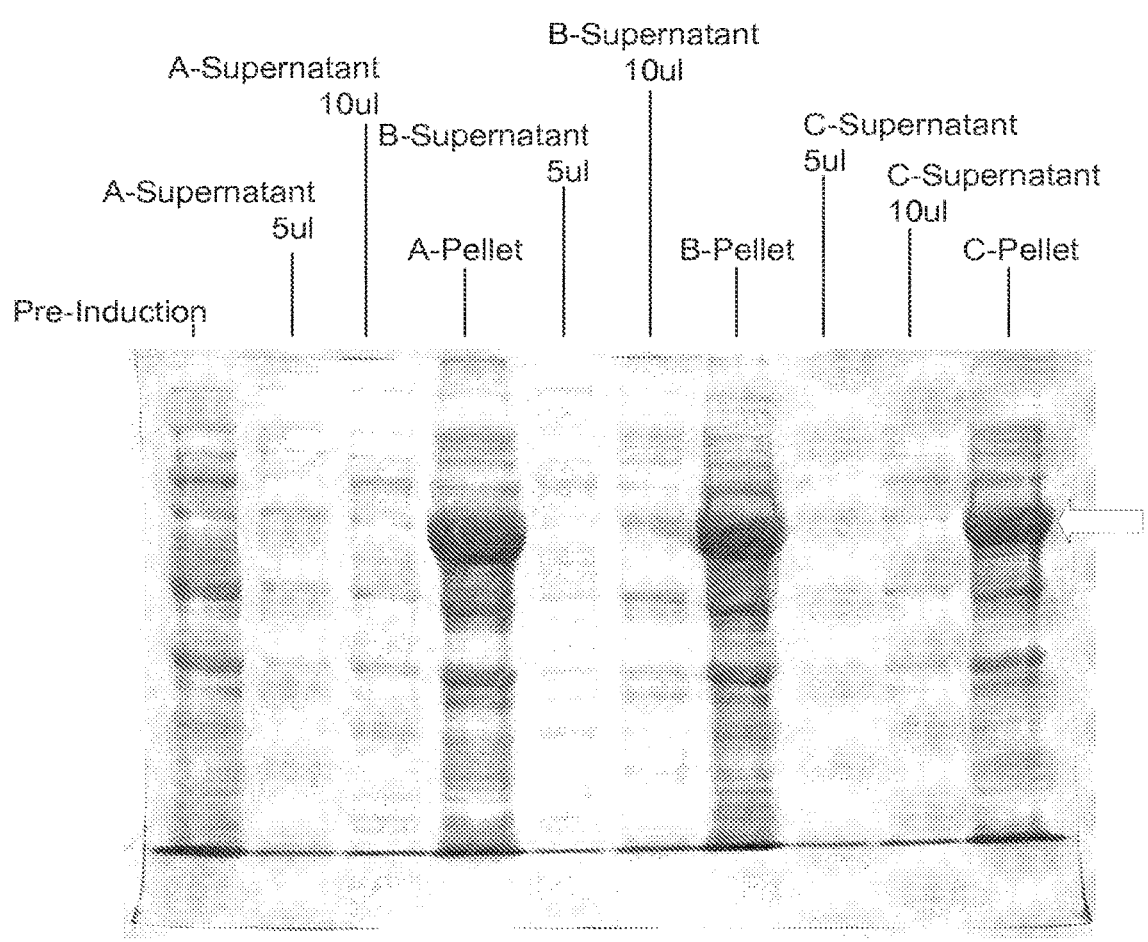
FIG. 2A shows the expression of FDC1 in *E. coli* at 37° C., using three different buffers. The recombinantly produced FDC1 only accumulated in the insoluble pellet fractions (inclusion bodies).

At 37° C., the recombinant FDC1 was not expressed as a soluble form in *E. coli*, and formed inclusion bodies, as shown in FIG. 2A. The standard protocols for expressing recombinant proteins are not applicable for FDC1.

Figure 2B:
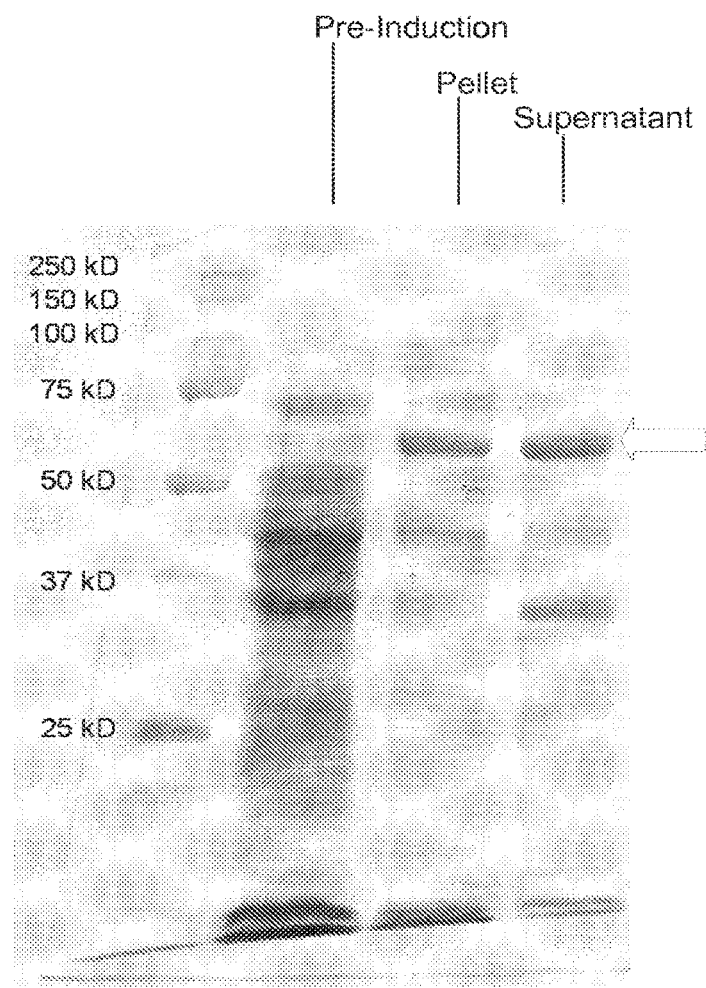
FIG. 2B shows the expression of FDC1 in *E. coli* at 16° C. Soluble FDC1 was detected in the supernatant.

To produce functional FDC1 in *E. coli*, expression of FDC1 was induced at various temperatures (37° C., 30° C., 25° C., 18° C., and 16° C.) in the presence of various concentrations of IPTG (0.2 mM, 0.5 mM). Concentrations of IPTG had no significant effect on expression; however, lower temperature improved expression and solubility of this protein. Optimal FDC1 expression was achieved after induction with 0.2 mM IPTG at 16° C. for 16 hours (FIG. 2B). The cells were harvested by centrifugation at 4500 rpm at 4° C. and washed once with 1×PBS buffer and then stored at −80° C.

Expression of FDC1 was examined by SDS-PAGE (10% acrylamide slab gel, 0.75 mm thick), using the Laemmli protocol. Coomassie brilliant blue R-250 was used to stain the protein band.

Our results indicated that expression of FDC1 at lower temperature with lower concentration of IPTG played a role for the correct folding of the enzyme, and the conversion of aggregated or misfolded forms to a soluble, functional form.

2. Purification of Yeast FDC1

There is no report on the purification and characterization of yeast FDC1. To examine the activity and properties of FDC1, functional FDC1 that was recombinantly produced from *E. coli* was purified.

Figure 3:
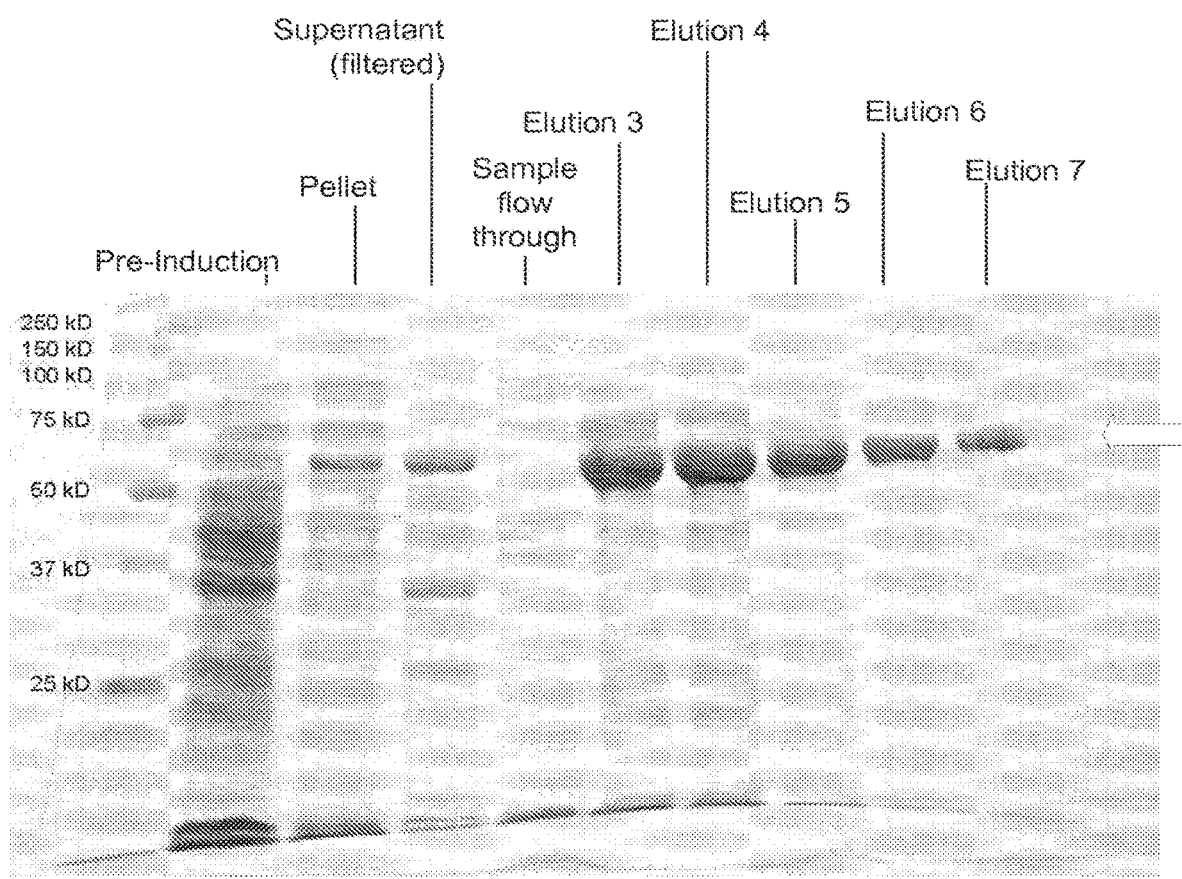
FIG. 3 shows the SDS-PAGE analysis of purified FDC1.

Purification was carried out in an anaerobic environment at 4° C. The cells were suspended in buffer A (composed of 50 mM Tris-HCl pH 8.0 containing 50 mM $Na_2S_2O_3$, 25 mM TCEP, 500 mM NaCl, 0.5 mM PMSF, 20 mM β-mercaptoethanol, 20% glycerol, and 10 mM imidazole) containing 10 mM $MgCl_2$, 0.2% Triton X-100, 2 µg/mL DNAse, 2 µg/mL RNAse, and 4 µg/mL lysozyme. The cells were disrupted by ultra-sonication and the supernatant was collected by centrifugation at 15,000 g for 20 min at 4° C. The resulting supernatant was filtered through a 0.45 µm PES filter and then applied to $Ni^+$-agarose affinity column (GE Healthcare), equilibrated with the buffer A. The column was washed well with buffer A until all the non-specific binding proteins eluted from the column. The protein was eluted with buffer A containing 250 mM imidazole. The protein content was determined by the spectrophotometer at 280 nm. The protein was fairly pure (FIG. 3).

Recombinant FDC1 that can convert tCA to styrene was purified. However, the protein lost its activity very fast during purification. The protein activity can be maintained when the purification was conducted under an anaerobic condition, such as by adding higher amounts of reducing agents (50 mM $Na_2S_2O_3$, 25 mM TCEP, and 20 mM β-mercaptoethanol) in the buffers.

3. Activity Assays for Recombinantly Produced FDC1

To study the function of recombinant FDC1 in vitro, the effects of various conditions (e.g., buffers at a wide pH range, various substrate concentrations, and various organic solvents for product extraction) on the enzymatic activity of FDC1 were tested.

First, an enzymatic assay that is very accurate and reproducible was developed, which can measure FDC1 activity at a low concentration of substrate.

The standard reaction mixture for decarboxylation consisted of 25 mM potassium phosphate buffer (pH 6.5) containing 5 mM dithiothreitol, 1.4 mM trans-cinnamic acid and enzyme (0.50 mg) to a final volume of 1.0 mL. The reaction was started by the addition of the enzyme and was incubated at 30° C. for 5 min. The reaction was stopped by adding 24 µl of glacial acetic acid (17.4N) after which 2-propanol was added in equal volume to the reaction mixture in order to solubilize the product. The amount of styrene produced was measured by HPLC using a Dionex Ultimate3000 UHPLC equipped with an auto sampler, diode array (UV/Vis) detector, and reverse phase Acclaim 120 C18 column (2.1×150 mM Dionex USA). Samples (10 µl) were injected for analyses at a total constant flow rate of 0.6 ml/minute. The samples were resolved in 0.15% acetic acid (A) with an increasing concentration gradient of acetonitrile containing 0.15% acetic acid (B) for 0 to 4 min, 5%; 4 to 5 minutes, 5 to 40%; 5 to 7 min, 40 to 45%; 7 to 8 min, 45 to 85%; 8 to 12 min, 85 to 95%; 12 to 14 minutes, 95 to 5% at a flow rate of 1 ml/min. The specific activity was expressed in U (nmol styrene)·$mg^{-1}$·$min^{-1}$.

4. Effect of pH on FDC1 Activity

Figure 4:
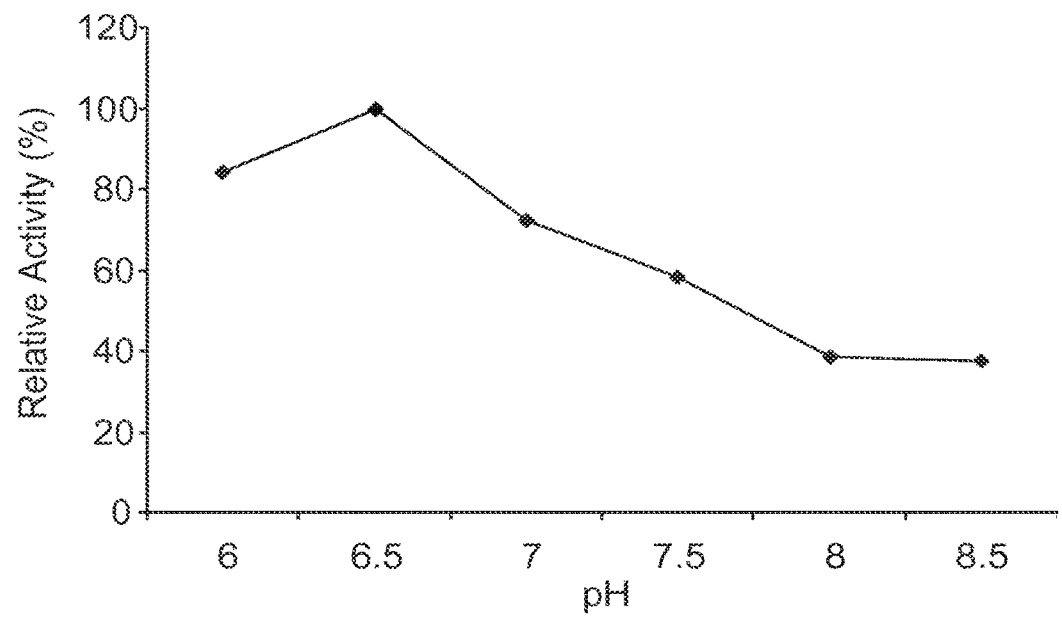
FIG. 4 shows the effect of pH on FDC1 activity. The enzyme showed maximum activity at pH 6.5, and is considered as having 100% relative activity. The x-axis represents pH values of different reaction buffers.

Buffer pH is one of the main factors that can influence an enzymatic reaction. Reactions in buffers at pH 6.0, 6.5, 7.0, 7.5, 8.0, and 8.5, respectively, were carried out to evaluate optimal pH for FDC1 activity. Potassium phosphate buffer was used for pH values 6.0 to 7.5 and Tris-HCl buffer was used for 8.0 and 8.5. The reaction mixture was composed of 200 µM cinnamic acid, 5 mM DTT, 100 mM various pH buffers, and 150 µL FDC1 crude extract to a final volume of 1 mL. The reaction mixtures were incubated for 30 minutes at 30° C. The styrene was extracted with 100 µL of butanol. The experimental negative control used the same conditions except the reaction mixture contained no substrate. The optimal pH for the decarboxylation of FDC1 crude extract was found to be about 6.5. Our results showed that buffer had a significant impact on FDC1 activity, and FDC1 showed highest activity at pH 6.5 (FIG. 4). This information is useful for industrial production of styrene.

5. pH Stability of FDC1

Buffer also affects the stability of FDC1 and the reaction rate. To study the stability of FDC1, the protein was incubated in buffers of different pH values, from 5.0 to 11.0.

Figure 5:
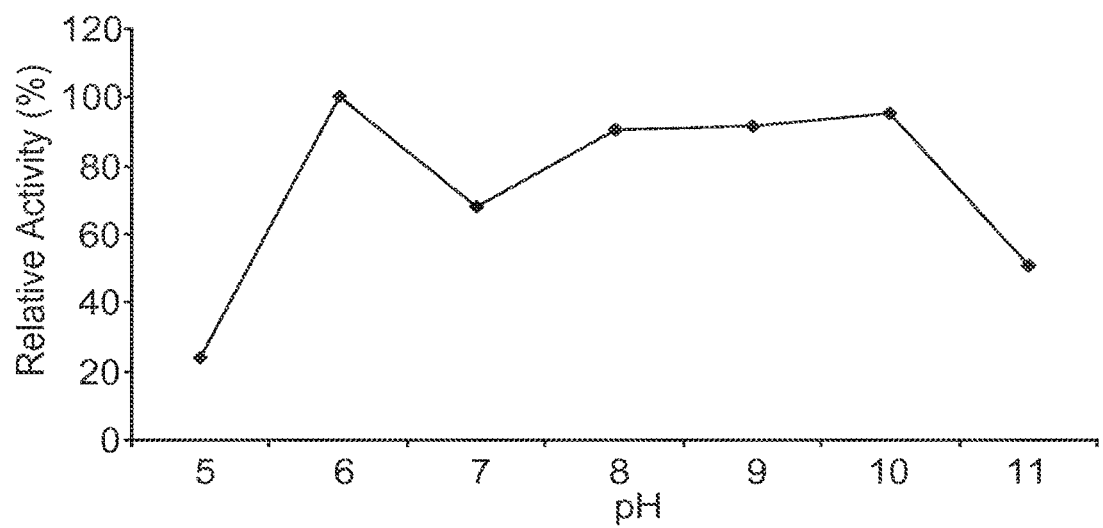
FIG. 5 shows the pH stability of FDC1. The enzyme exhibited good pH stability. It did not lose any activity when incubated for 30 minutes at pH 6.0 prior to the reaction, and is considered as having 100% relative activity. The x-axis represents pH values at which the protein was incubated for 30 minutes prior to enzymatic reaction.

The protein (crude extract, 586 µL) was added to 112 µL of 500 mM buffers at pH values of 5, 6, 7, 8, 9, 10, and 11, and incubated at 30° C. for 30 minutes. After treated in various pH buffers, an aliquot of protein (42 mg) was added to a final concentration of 100 mM potassium phosphate buffer pH 6.5, 5 mM DTT, 1.4 mM cinnamic acid and brought up to a final volume of 2 mL. The reaction mixture was then incubated for 8 minutes at 30° C. The styrene was extracted by the addition of 250 µL butanol. The experimental negative control used the same conditions except the reaction mixture contained no substrate. The FDC1 crude extract was found to be stable at a pH ranging from 6 to 10 (FIG. 5). This protein is stable and active in a wide range of pH and can be used for industrial production of styrene.

6. Effect of Temperature on FDC1 Activity

Temperature can affect the stability of FDC1 and the reaction rate. The effect of temperature on reaction rate is described by the Arrhenius equation. As a rule of thumb, reaction rates for many reactions double or triple for every 10 degrees Celsius increase in temperature, though the effect of temperature may be much larger or smaller than this.

Figure 6:
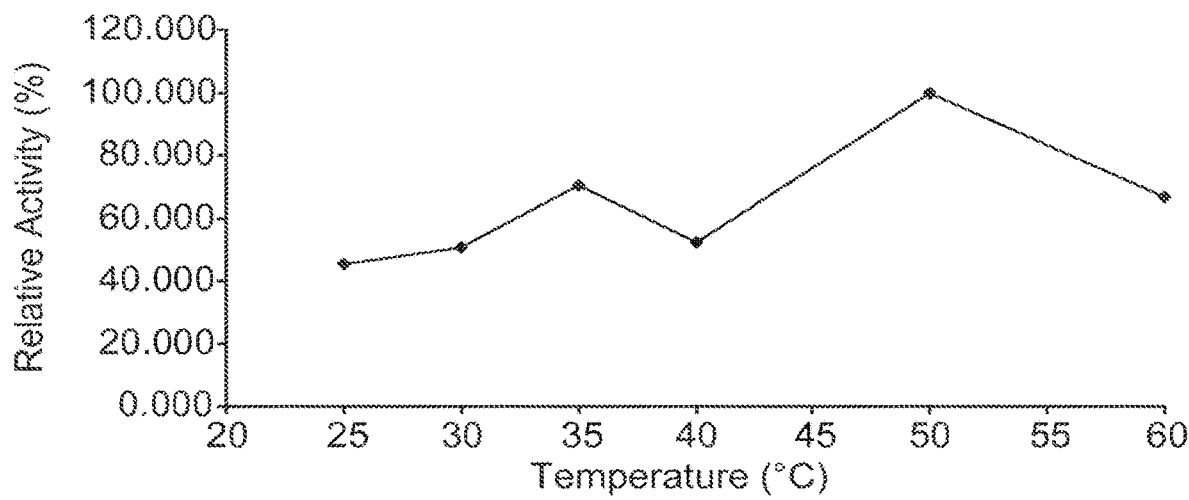
FIG. 6 shows the effect of temperature on FDC1 activity. The enzyme showed maximum activity when the reaction was carried out at 50° C., and is considered as having 100% relative activity. The x-axis represents temperatures at which the enzymatic reactions were carried out.

To evaluate the optimal temperature for FDC1, reactions were carried out at temperatures of 25° C., 30° C., 32° C., 35° C., 40° C., 50° C., and 60° C., respectively, for 30 minutes. The protein (FDC 1 crude extract, 13 mg) was added to reaction mixtures containing 25 mM potassium phosphate pH 6.5, 5 mM DTT, and 1.4 mM cinnamic acid to a volume of 1 mL. After the reaction 1 mL of propanol was added to the reaction mixtures to dissolve styrene. The experimental negative control used the same conditions except the reaction mixture contained no substrate. The optimum temperature for FDC1 activity was about 50° C. (FIG. 6).

Unexpectedly, the enzyme showed its maximum activity at a higher temperature as compared with other yeast enzymes. This information is useful for industrial production of styrene because a significant amount of cost associated with fermentation is cooling the fermentation system. Since FDC enzyme is active at higher reaction temperature, temperature range for fermentation can be controlled for increased yield and reduced cost on cooling.

7. Temperature Stability of FDC1

Figure 7:
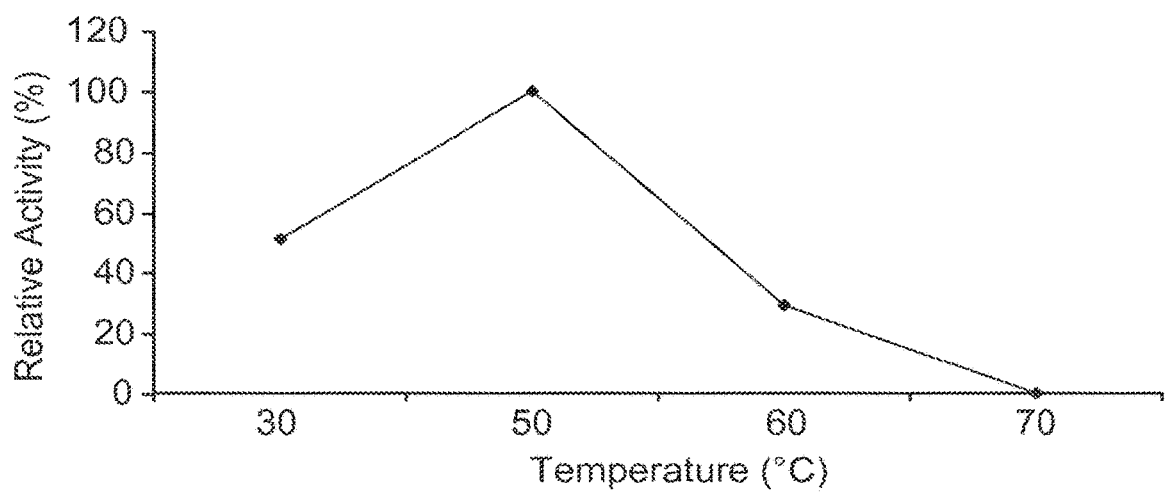
FIG. 7 shows the temperature stability of FDC1. The enzyme showed maximum activity at 50° C., and did not lose any activity when incubated at 50° C. for 30 minutes prior to the reaction (which is considered as having 100% relative activity). The x-axis represents temperatures at which the enzyme was incubated prior to enzymatic reaction.

To study the temperature stability of FDC1, reactions were carried out at temperatures of 30° C., 50° C., 60° C., and 70° C., respectively, for 30 minutes. After incubation at various temperatures, an aliquot of protein (42 mg) was added to 25 mM potassium phosphate buffer pH 6.5, 5 mM DTT, and 1.4 mM tCA to a final volume of 1 mL. The reaction mixtures were incubated for 8 minutes at 30° C. The styrene was extracted with 250 µl butanol and quantified by HPLC using C18 column. The experimental negative control used the same conditions except the reaction mixture contained no substrate. The enzyme was stable at 50° C. (FIG. 7).

Figure 8:
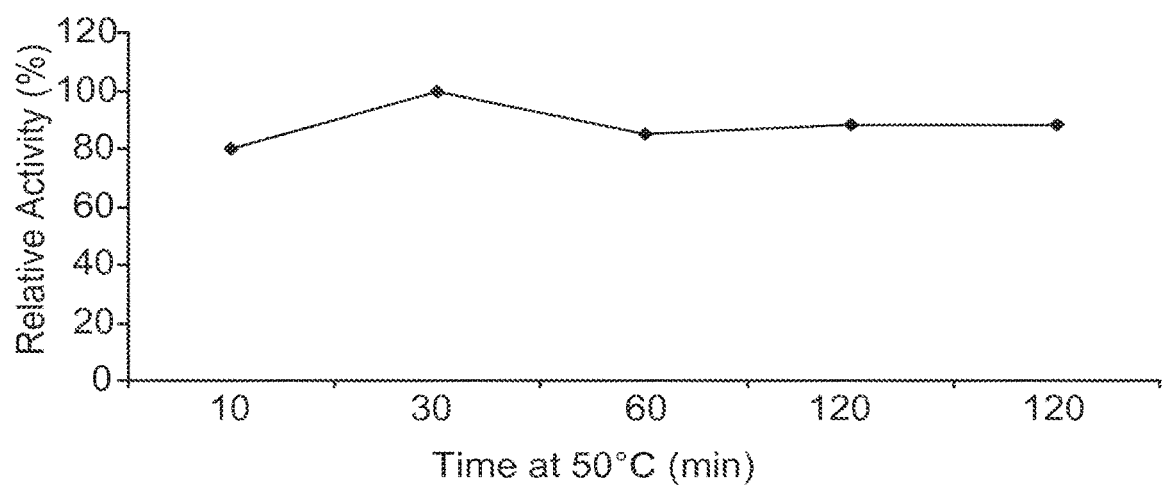
FIG. 8 shows the temperature stability of FDC1 at 50° C. for various time periods. The enzyme showed maximum activity after being incubated at 50° C. for 30 minutes prior to the reaction, and is considered as having 100% relative activity. The x-axis represents the duration (in minutes) in which the enzyme was incubated at 50° C. prior to enzymatic reaction.

The stability of FDC1 crude extract at 50° C. was also tested by incubating the crude extract at 50° C. for 10, 30, 60, and 120 minutes, respectively. After the protein was incubated for various times, an aliquot (42 mg) was added to 25 mM potassium phosphate buffer pH 6.5, 5 mM DTT, and 1.4 mM tCA to a final volume of 1 mL. The reaction mixtures were then incubated for 8 minutes at 30° C. Styrene was extracted by adding 250 µL butanol to the reaction mixtures and quantified by HPLC. The experimental negative control used the same conditions except the reaction mixture contained no substrate. The protein was stable at 50° C. for 2 hr (FIG. 8). This result demonstrates that the protein retained 100% of its activity even after incubation for about 2 hours. This piece of information is useful for industrial production of styrene, due to the thereto stability of FDC1.

8. Effect of Cofactors on FDC1 Activity

To examine the effect of cofactors on FDC1 enzymatic activity, reactions were carried out with various cofactors. Several cofactors, including thiamin pyrophosphate (TPP), biotin, and pyridoxal phosphate (PLP) were tested for their effects on FDC1 activity. Reaction mixtures containing 25 mM potassium phosphate buffer pH 6.5, 5 mM DTT, 0.5 mM tCA, 0.5 mM cofactor, and 0.5 mg purified FDC1 to a volume of 1 mL were incubated for 30 minutes at 30° C. Styrene was extracted with 250 μL butanol. The experimental control used the same conditions except the reaction mixture contained no cofactors. The experimental negative control used the same conditions except the reaction mixture contained no substrate.

Figure 9:
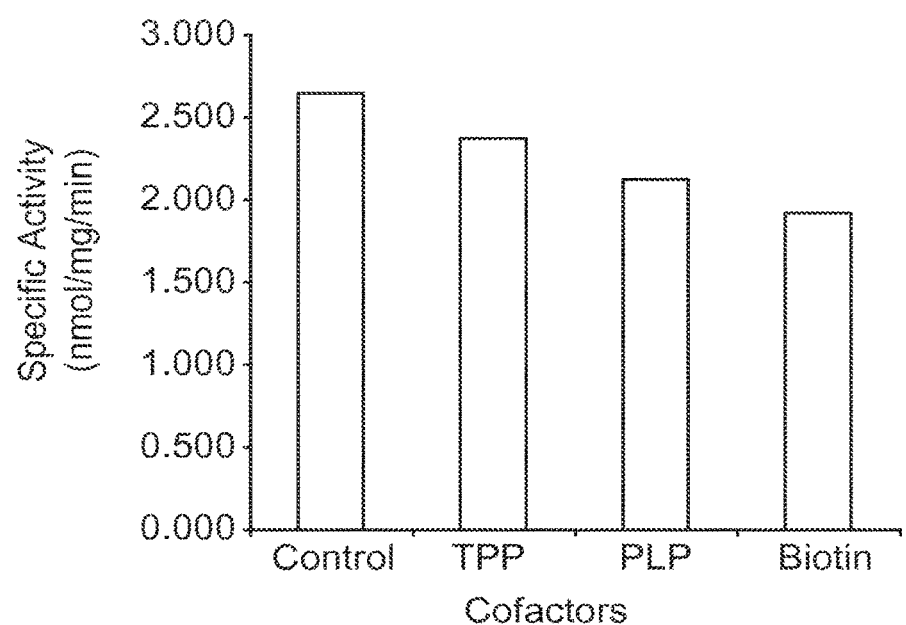
FIG. 9 shows the effect of cofactors on FDC1 activity. Specific activity is shown as nmol of styrene produced per mg enzyme per minute.

None of the cofactors increased the activity of FDC1. In fact, they were found to decrease FDC1 activity (FIG. 9). This result showed that this enzyme does not require any commonly known cofactors for its activity.

9. Effect of Metal Ions on FDC1 Activity

Figure 10A:
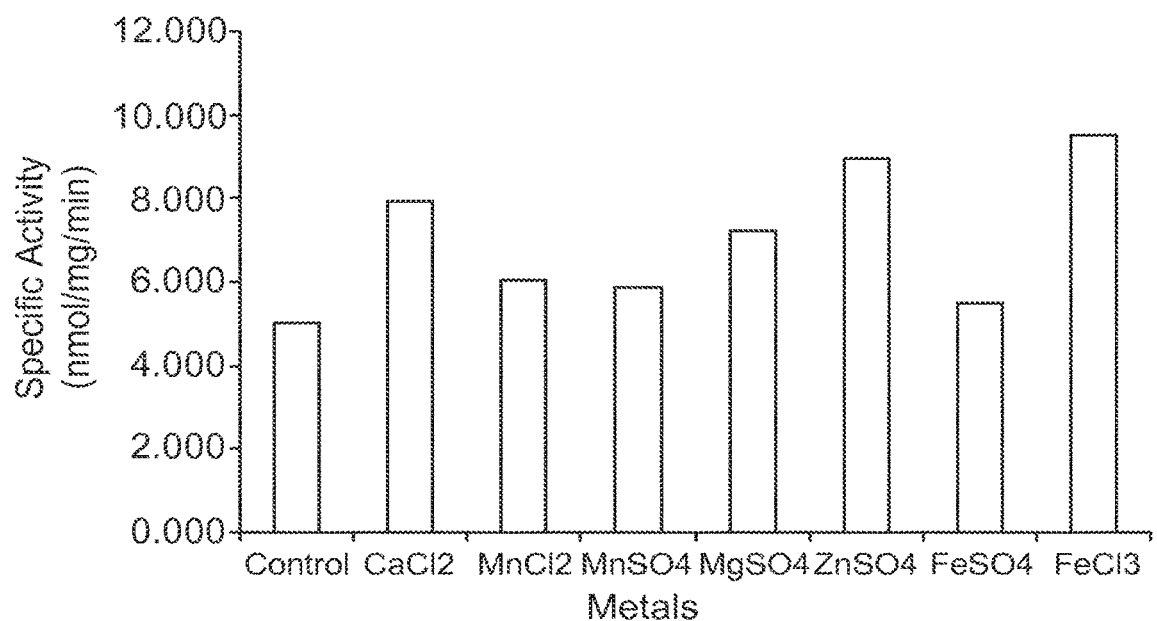
FIG. 10A shows the effect of metal ions on FDC1 activity.

To study the effect of metal ions on FDC1 activity, reactions were carried out with various metal ions, including $ZnSO_4$, $FeCl_3$, $MnCl_2$, $MgSO_4$, $CaCl_2$, $MnSO_4$, and $FeSO_4$. Reaction mixtures of 25 mM potassium phosphate buffer pH 6.5 containing 1.4 mM tCA, 5 mM DTT, 10 mM metal ion, and 0.5 ing purified FDC1 adjusted to a final volume of 1 mL were incubated for 5 minutes at 30° C. After the reaction, 1 mL of propanol was added to the reaction mixtures to solubilize styrene. The experimental control used the same conditions except the reaction mixture contained no metal ions. The experimental negative control used the same conditions except the reaction mixture contained no substrate. $Ca^{2+}$, $Mg^{2+}$, $Zn^{2+}$, and $Fe^{3+}$ ions increased the activity of FDC1 (FIG. 10A).

Figure 10B:
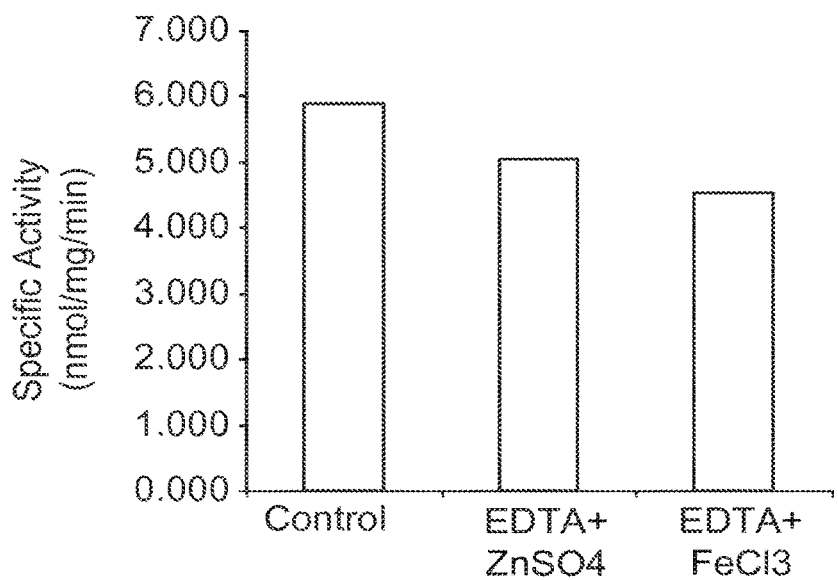
FIG. 10B shows the effect of $Zn^{2+}$ and $Fe^{3+}$ on FDC1 activity. Specific activity is shown as nmol of styrene produced per mg enzyme per minute.

The effects of $Zn^{2+}$ and $Fe^{3+}$ on FDC1 activity were further investigated using EDTA to cancel out the effects of the metal ions. Reaction mixtures of 25 mM potassium phosphate buffer pH 6.5 containing 1.4 mM tCA, 5 mM DTT, 10 mM metal ion, 10 mM EDTA and 0.5 mg purified FDC1 were adjusted to a final volume of 1 mL, and were incubated for 5 minutes at 30° C. After the reaction, 1 mL of propanol was added to the reaction mixtures to solubilize styrene. The experimental control used the same conditions except the reaction mixture contained no metal ions or EDTA. The experimental negative control used the same conditions except the reaction mixture contained no substrate. The reactions containing the metal ion and EDTA had a similar activity as compared to the control (FIG. 10B), indicating that $Zn^{2+}$ and $Fe^{3+}$ increased the activity of FDC1. Based on results presented in FIGS. 10A and 10B, enzyme activity of FDC1 can be increased by metal ions and it was not due to experimental artifact. For industrial production of styrene, this piece of information suggests that including certain metal ions in the culture media can be beneficial to styrene biosynthesis.

10. Substrate Specificity

Figure 11:
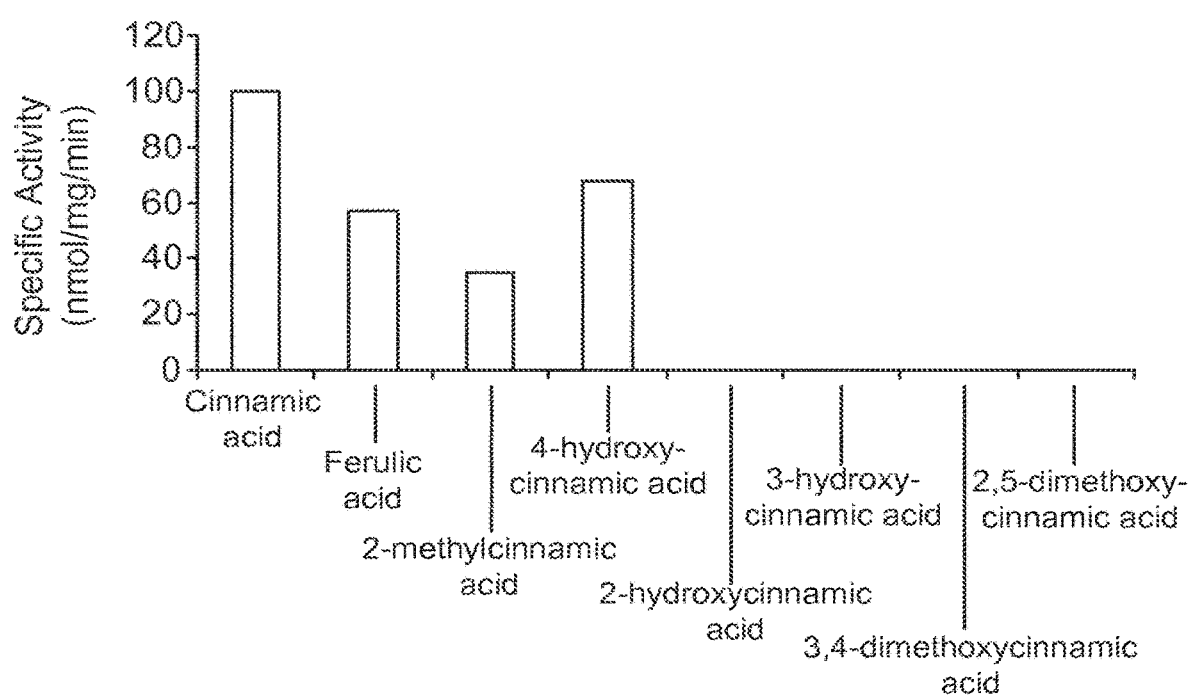
FIG. 11 shows the substrate specificity of FDC1. The enzyme showed maximum activity when t-cinnamic acid is used as a substrate, and is considered as having 100% relative activity.
Figure 12A:
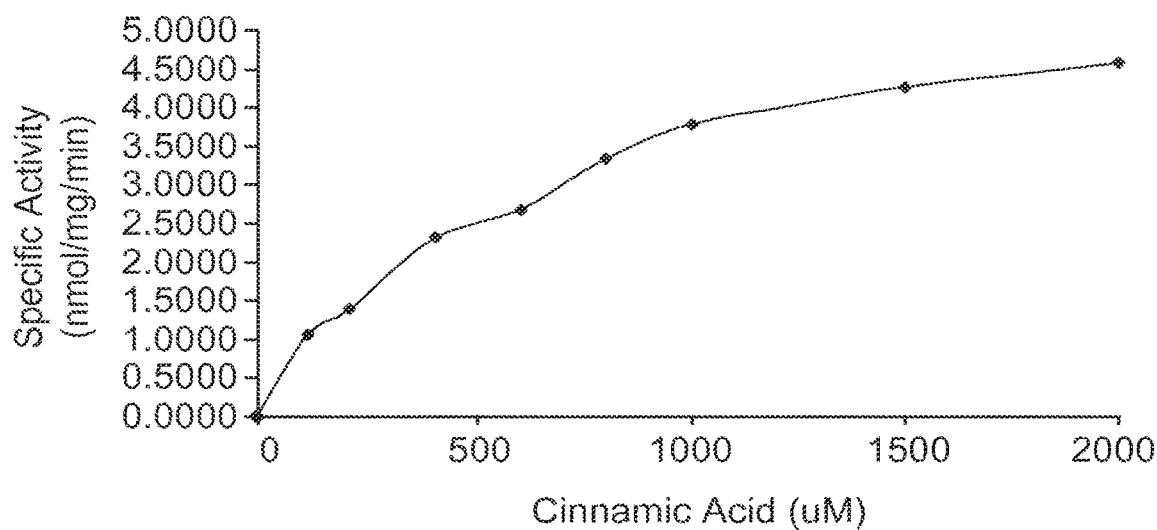
FIGS. 12A and 12B depict the kinetic analysis of FDC1. The x-axis represents the enzymatic reaction with various concentrations of substrate. Specific activity is shown as nmol of styrene produced per mg enzyme per minute.
Figure 12B:
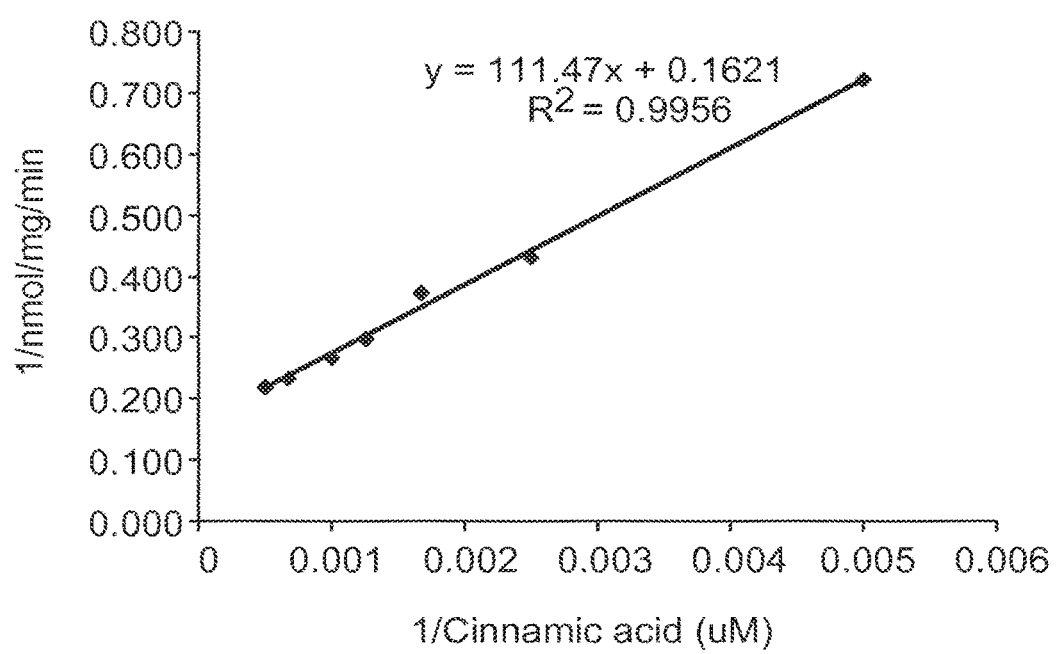

To examine whether FDC1 is highly specific for tCA (or whether it shows substrate promiscuity), tCA and its substrate analogues, such as ferulic acid, 2-methylcinnamic acid, 2-hydroxycinnamic acid, 3-hydroxycinnamic acid, 4-hydroxycinnamic acid, 3,4-dimethoxycinnamic acid, and 2,5-dimethoxycinnamic acid were tested. The reaction mixtures of 25 mM potassium phosphate buffer pH 6.5 containing 5 mM DTT, 0.2 mM substrate, and 0.5 mg purified FDC1 were adjusted to a final volume of 1 mL. The reaction mixtures were then incubated for 5 minutes at 30° C. After the reaction 1 mL of propanol was added to the reaction mixtures to solubilize styrene. The experimental negative control used the same conditions except the reaction mixture contained no substrate. The substrates ferulic acid, 2-methylcinnamic acid, and 4-hydroxycinnamic acid showed activities of 57%, 35%, and 68%, respectively, compared with that of tCA (FIG. 11). The enzyme did not show any activity for substrates 2-hydroxycinnamic acid, 3-hydroxycinnamic acid, 3,4-dimethoxycinnamic acid, and 2,5-dimethoxycinnamic acid (FIG. 11). The enzyme did not show strict specificity for tCA; instead, it showed moderate activity for ferulic acid, 2-methylcinnamic acid and 4-hydroxycinnamic acid.

Analyses of the substrate specificity will contribute to elucidate substrate binding site and the mechanism of enzyme activity. In addition, this substrate spectrum suggested that the same fermentation system can be used to produce different industrial monomers. In addition to converting cinnamic acid to styrene, 4-hydroxy, 3-methoxystyrene (a.k.a. 4-vinylguajacol, 4VG) from ferulic acid; 2-methyl-styrene from 2-methylcinnamic acid; and 4-hydroxystyrene (a.k.a. 4-vinylphenol) from 4-hydroxycinnamic acid can now be produced.

11. Kinetics

To examine the catalytic efficiency of this protein, kinetic studies of FDC1 was conducted using tCA as the substrate. To measure the steady state kinetic constants of wild type FDC1, enzymatic activities were determined with different concentrations of tCA (100-2000 μM). The reactions were performed in a total of 1.0 mL standard reaction mixture with 0.5 mg purified protein, and were allowed to proceed for 5 min at 30° C. The styrene was extracted with 250 μL butanol. The experimental negative control used the same conditions except the reaction mixture contained no substrate. Activities were quantified by standard assay method. Duplicate assays were performed and averaged. The $V_{max}$ and $K_m$ were determined by nonlinear regression analysis of the velocity-concentration data fit to the Michaelis-Menten equation.

The $K_m$ for wild type FDC1 was found to be 688 μM and the $V_{max}$ was 6.17 nmol·mg$^{-1}$·min$^{-1}$. The catalytic efficiency of this protein was found to be 8.4 M$^{-1}$ S$^{-1}$ which is lower compared with that of other natural enzymes. Lower catalytic efficiency of FDC1 is the major obstacle for production of styrene. Structure guided protein engineering will be a good approach for molecular evolution of FDC1 for increasing activity.

Example II. FDC1 Mutants and Mutant Libraries

1. FDC1 Structure Models

There is no tertiary structure of FDC1 that can be used for analyses of substrate binding sites. A homologous protein structure (3-Octaprenyl-4-Hydroxybenzoate decarboxylase, PDB code: 2IDB) showed only 20% identity with FDC1. To analyze substrate binding site, a model was built for truncated FDC1 by SWISMODEL program and a model for full length FDC1 by I-TASSER program. These two models are reliable as they superimpose very well. As the lower catalytic efficiency of FDC1 is a bottleneck to produce higher amounts of styrene, we applied a combined method of molecular biology and structural biology for laboratory evolution of a protein based model of full length wild type FDC1 (FIG. 1A).

Docking Substrate into FDC1.

For laboratory evolution of protein, the substrate binding site of FDC1 was examined. There is no report on the substrate binding site of FDC1. Docking for tCA with FDC1 was performed using the computer program SWISDOCK. After docking, it gave 4 possible binding sites (FIG. 1B).

After analysis of the structure, site C is studied for molecular evolution to improve the activity. Without limiting the scope of the subject technology, it is hypothesized that I173, A174, R175, V188, I189, K190 (not shown for figure clarification), I194, E280, M286, F291 and F440 contribute to substrate binding (FIG. 1C). Thus, the hydrophobic residues (A174, I194 and V188) create a pocket for binding the phenyl ring of tCA; and positive charged R175 makes hydrogen bonds with the carboxylic group of tCA and negative charged E280.

2. Saturation Mutagenesis of FDC1

As the conventional mutagenesis did not improve FDC1 activity, site directed saturation mutagenesis was applied. Saturation mutagenesis allows the change of one amino acid to 19 other alternative amino acid residues. Saturation mutagenesis was performed at sites 155-156, 159, 162-164, 172-175, 187-196, 226-227, 285-287, 291, 326, 331, 360-361, 395-396, 398, and 440-441 of FDC1 by following the QuickChang site-directed mutagenesis strategy (STRATAgene, CA) using NNK degenerate primers (N represents the mixture of A, T, G, C, and K for G/T). The codon NNK has 32-fold degeneracy and encodes all 20 amino acids without rare codons. The QuikChange PCR products were examined by agarose gel electrophoresis and then 15 µl of PCR products were digested with 1 µl Dpnl (New England Biolabs) at 37° C. for 4 hours to remove the template plasmid. Aliquots of (2 µl) digestive products were transformed into BL21-Gold (DE3) competent cells (STRATAgene, CA) and inoculated on Luria-Bertani (LB) agar plates containing kanamycin. The quality of the library by DNA sequencing was confirmed. The library covers 90% of mutagenesis (17 mutants out of 19). To cover 100% (19 out of 19 mutant), we screened 150 mutants for each site.

3. Colorimetric Method for High-Throughput Screening of FDC1 Mutant Library

Screening a large population of the protein library is the bottleneck for the molecular evolution of the protein. The functional characterization of decarboxylase routinely relies on analytic instruments, like HPLC or LC-MS. Although the HPLC is highly sensitive, it is time consuming, expensive, and generates waste like methanol or acetonitrile and not suitable for high-throughput applications. To overcome these technical barriers, a spectroscopic-based colorimetric assay method was developed, which was essentially based on detecting the enzymatically produced styrene from tCA. Detailed method has been given below.

The transformants (Example II.2) were inoculated in 96-well plates (NUNC, Roskilde, Denmark) containing 100 µl LB broth per well and incubated at 37° C., overnight. The cultures were then mixed with equal amount of 50% glycerol and stored at −80° C. as the master plate. An aliquot of 10 µl culture was inoculated in 2 ml deep-well plates (USA scientific) with 1 ml TB broth per well and incubated at 37° C. until the $OD_{600}$ reached 1.0. The cultures were then induced by 0.2 mM IPTG and incubated at 18° C. for 20 hours with shaking at 250 rpm.

Cells were harvested and suspended with 0.25 ml PBS buffer at pH 7.0 and the substrate (tCA) was added at a final concentration of 1 g/L. The culture was incubated at 30° C. for 4 hours and the volatile product styrene was collected by using 96 well STRATA-X® reversed phase plate containing 10 mg polymer based resin (Phenomenex) on top of the culture plate (FIG. 19). To avoid styrene vapor diffusion, 96-square well silicone sealing mats with pre-slit were used between 96-well culture plate and 96 well STRATA-X® reversed phase plate. The product was collected by 200 µl propanol for each well and the amount of product was measured by colorimetric method.

Various chemicals were tested as an indicator for styrene detection, including NBP (4-nitrobenzyl-pyridine) as a preferred indicator. Styrene was mixed with cytochrome P450 BM-3 in 50 mM phosphate buffer pH 8.0. The styrene oxidation reaction was started by adding 0.2 mM NADPH, and the reaction mixture was incubated at room temperature for 5 minutes with shaking. The NBP solution was added to the mixture and incubated at room temperature for further 5 minutes with shaking which gives white precipitate. The tube or plate containing reaction mixtures were heated at 70° C. for 30 minutes and chilled on ice for 5 minutes. After adding Dimethylformamide (150 µl) and 25 µl of 1M $K_2CO_3$, the reaction mixture gave blue color that can be measured spectrophotometrically at 600 nm immediately. The unpaired electron of NBP reacts with the oxirane ring of styrene oxide to yield a blue chromophore a blue color that can be monitored spectrophotometrically at 600 nm.

The 96-well plate cultures that contain styrene were monitored directly using this high throughput method (FIG. 13). This method can detect styrene as low as 1.0 mM. This colorimetric method is very fast, less expensive, reproducible and can measure 1000 colonies in a single day.

The mutants showing higher activity were confirmed by HPLC using an ACQUITY UPLC BEH C18 column (1.7-µm, 2.1×50-mm, Waters, USA). The samples were resolved in 30% acetonitrile (A) with an increasing concentration gradient of acetonitrile (B) for 1 min, 95%; then to 1 min, 30%; at a flow rate of 1 ml/min. UV absorption was monitored at 254-, 280-, and 310-nm. The changed amino acid residues in the mutants showing the higher activity were confirmed by DNA sequence.

Figure 14:
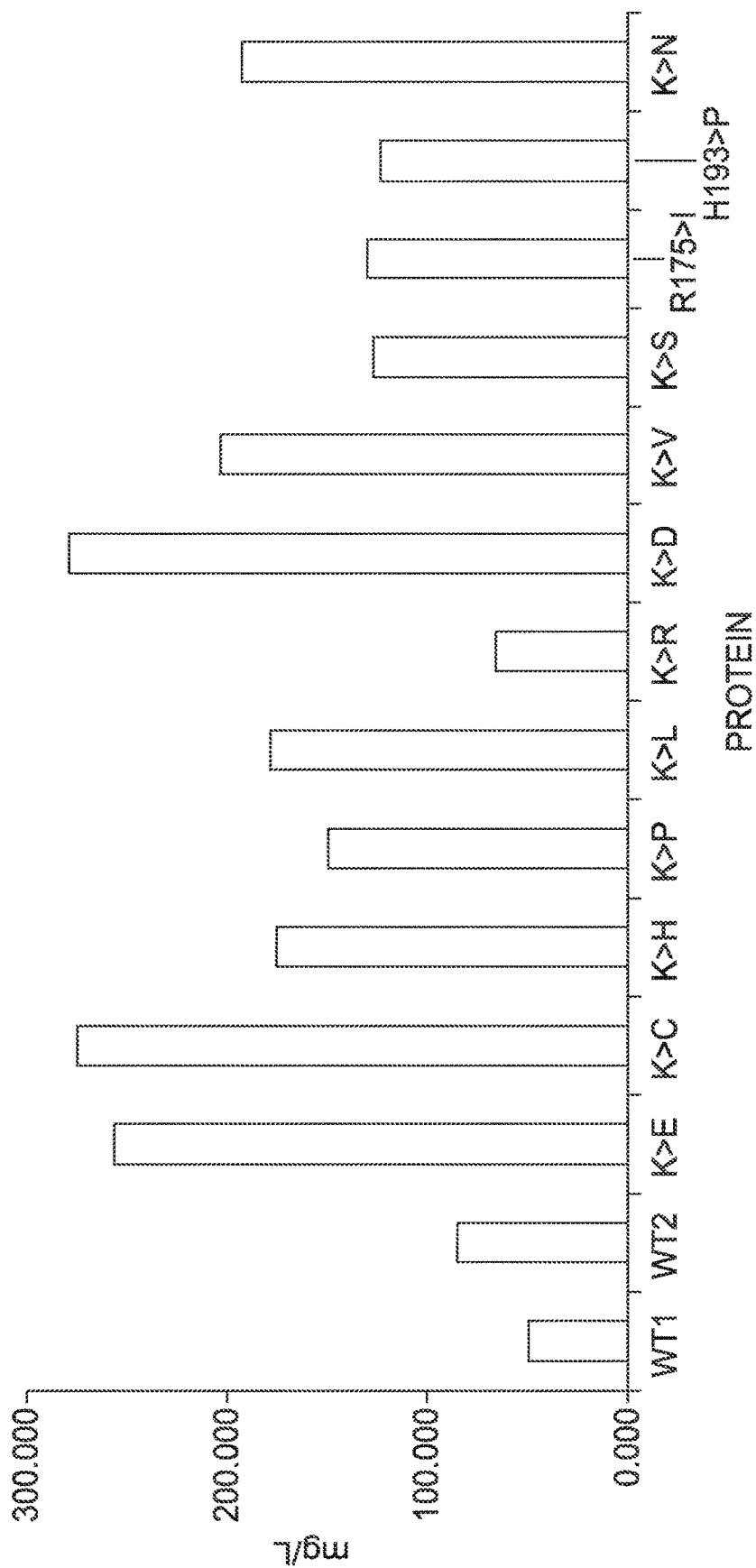
FIG. 14 shows styrene production by FDC1 mutants. The Y-axis represents amount of styrene produced by FDC1 mutants. The X-axis represents changed amino acids of the FDC1 mutants.

Several potential single mutants were identified (such as K190E, K190C, K190D, K190V, K190N, K190L, K190H, and R175I) that produced significantly higher amount of styrene, as compared to that of wild type (FIG. 14). Mutants K190E, K190C, K190V produced 3 times more, and mutant R175I produced 1.5 times more styrene, as compared to that of wild type. As such, the FDC1 mutants produced a significantly higher amount of styrene than that of wild type. Mutagenesis at different sites showed an additive or synergistic effect on protein evolution of methyltransferase (Bhuiya et al., 2010, Journal of Biological Chemistry, 285: 277-285.). Mutagenesis at K190 and R175 sites of FDC1 may further increase the production of styrene.

Production of styrene by maintaining the culture in an aerobic environment was conducted. Wild type FDC1 produced half the amount of styrene in an anaerobic condition, as compared to that of an aerobic condition. Using the STRATA-X® column, we can trap the volatile styrene and can maintain aerobic conditions.

Example III. FDC1-PAL Fusion Proteins

Expression of FDC-PAL2 Fusion Protein in *E. coli*.

Artificial channels were included in the styrene production. To construct the fusion protein of PAL2 and FDC using Gateway technology, four primers were designed for PCR amplification. The FDC-5' primer contained CACC sequence and the FDC-3' primer had a 9-amino acid linker, and two restriction sites NcoI and PstI at the 3'-end. To fuse PAL2 with FDC, the PAL2-5' primer correspondingly had an NcoI site and the PAL2-3' primer with a PstI site. The FDC gene (~1.5 kb) and the PAL2 gene (2.2 kb) were amplified using the above primers and cloned into the Gateway vector pDEST17. The constructs of the fusion protein of PAL2 and FDC were transformed to BL21(DE3). Fusion proteins of FDC mutant and PAL also can be obtained by the above process.

Figure 15:
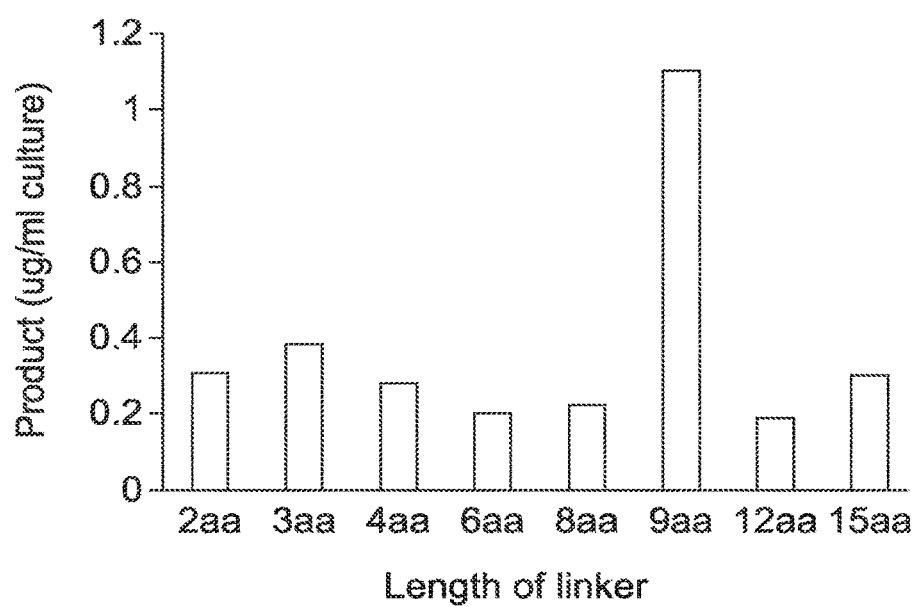
FIG. 15 shows the activities of FDC-PAL fusion proteins. The X-axis shows the lengths of the linkers.

The use of a linker for fusion proteins was evaluated based on the information from the resveratrol biosynthetic pathway. Previous results showed that fusion protein produced 15 fold more product compared with the expression two individual proteins (Yechun Wang et al (2011), JACS, 133: 20684-20687). The results indicate that linker plays an important role in fusion protein for improvement of biosynthetic pathway. Different length of linker 2, 3, 4, 6, 8, 9, 12 and 15 amino acid lengths were designed using GSG motif and examined the effect of linkers for resveratrol biosynthetic pathway. We found that 9 amino acid linker showed the highest yield, as compared to that of other linker (FIG. 15). Based on our findings, we designed 9 amino acid linkers for our PAL-FDC fusion proteins.

Figure 16:
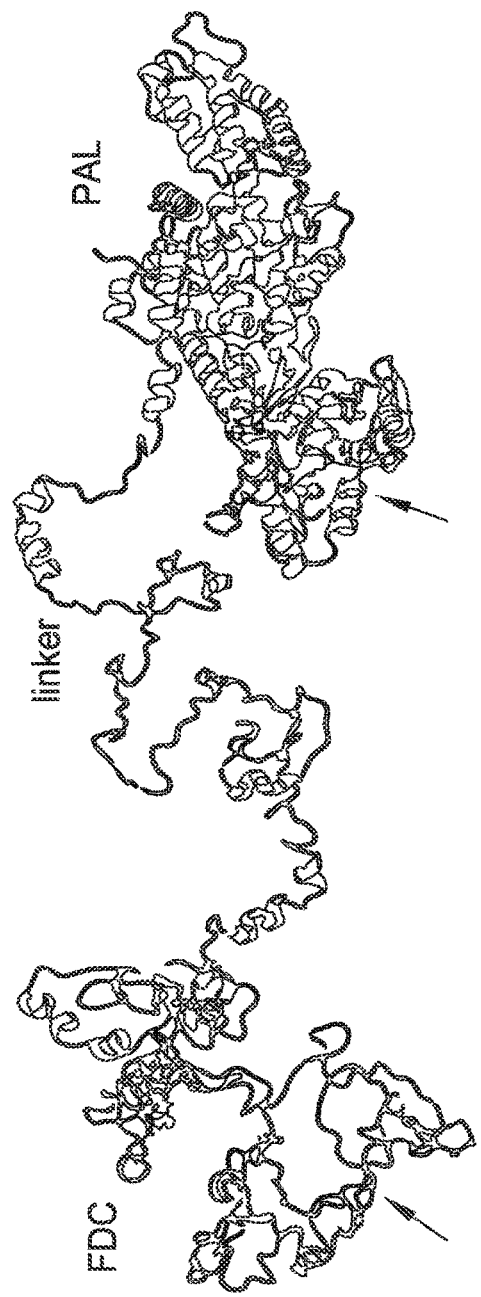
FIG. 16 is a schematic illustration of the predicted structure of FDC-PAL fusion protein.

Based on above observation, a computer model was constructed to prove that the artificial linker indeed increased metabolic channeling. The 9 a.a. linker connected two proteins (FIG. 16) in such a way that it prevent diffusion of intermediate (in this case cinnamic acid) so that intermediate can be uptake by second enzyme (FDC) efficiently and ultimately increase the final product styrene. The computer model predicted the distance between the two reaction centers (marked by the two arrows) are within 70 angstroms, forming a metabolic channel.

The expression analysis revealed that about 615 mg/L styrene was found in medium. This fusion protein produced styrene at an amount that was about 6-fold higher than that of FDC expressing in E. coli (95 mg/L in medium). This amount of styrene was also much higher than that of non-fused proteins of PAL2 and FDC (expressed in yeast, with 69 mg/L styrene detected). These analyses suggest that the fusion protein of PAL2 and FDC can be used to improve the bioproduction of styrene.

Example IV. Expression of an ABC-Transporter in E. Coli

Some bacteria have developed multiple mechanisms to adapt unfavorable conditions. For example, Pseudomonas strains have about three strategies for addressing organic solvent toxicity, i.e. modified membrane structure, active efflux pumps, and enzymatic detoxification. Here, a recombinant E. coli host expressing an efflux pump (called solvent-resistant-pump) was produced. The pump, a member of the ABC-transporter family, is composed of three subunits, srpA, periplasmic linker; srpB, inner membrane transporter; and srpC, out-membrane channels. The full-length of the srpABC pump sequence (~6 kb) was cloned from the genomic DNA of P. putida. The clone was first inserted to pENTR vector with Zeocin resistance and then to E. coli expression vector pCONA-2-DEST with Kanamycin resistance.

Figure 17:
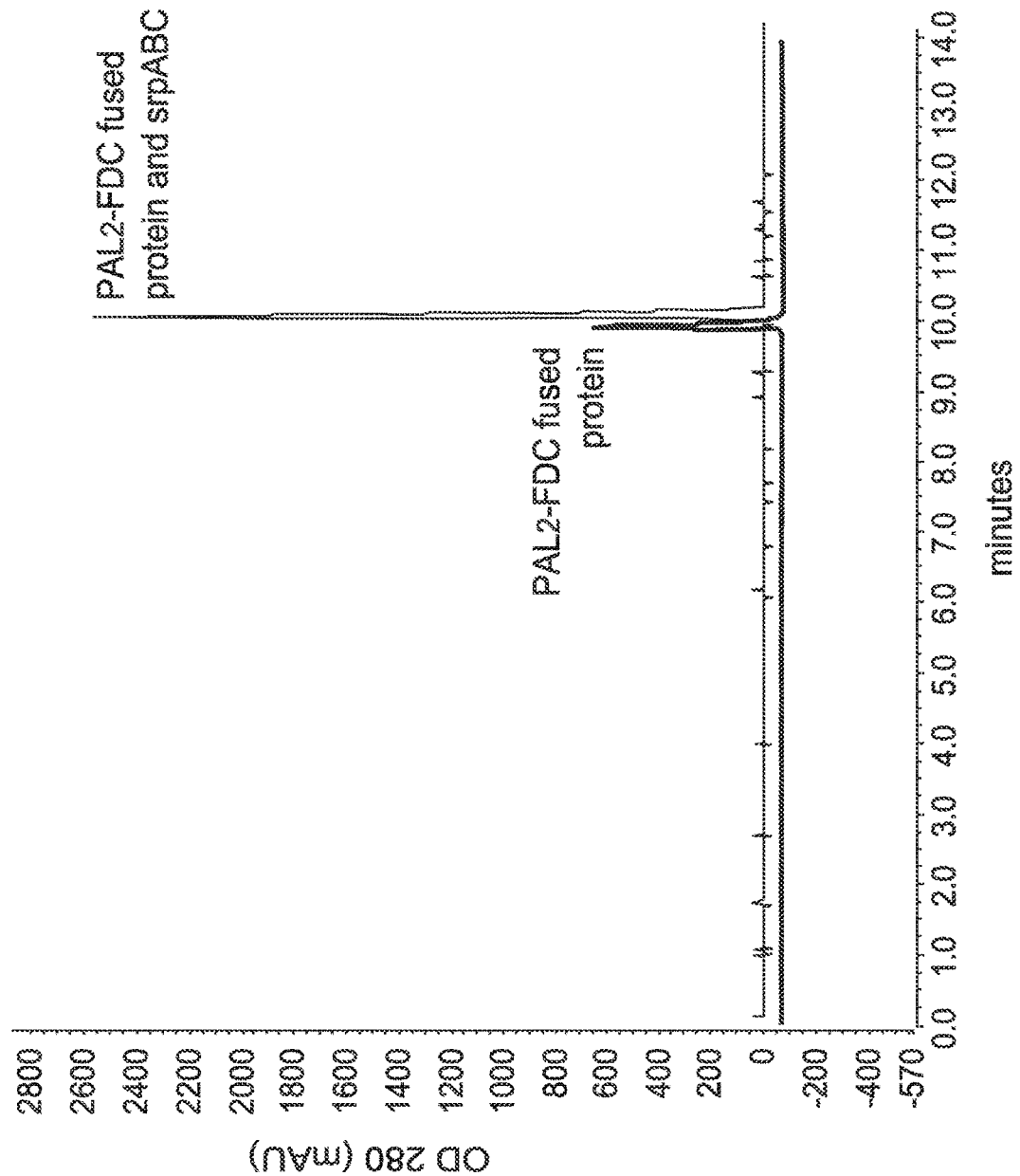
FIG. 17 shows that the production of styrene was significantly increased with the co-expression of an ABC-transporter.

Finally, the pump was transformed to the E. coli strain BL21 (DE3) containing the fusion of PAL2 and FDC which is resistant to Ampicillin. After the test expression of 5 clones in flasks, one clone was chosen for further experiment with fermenter. Fifty milliliters of overnight culture were inoculated in 1.5 L LB medium containing appropriate antibiotics. When cells reach an OD600~0.8, 5 mM of IPTG was added to the culture for induction. After 2 hrs the substrate Phe was added to a final concentration 5 g/L of cell culture. The styrene vapor was tracked in a bottle containing 250 ml of butanol. Samples from the overnight fermentation (~16 hrs) were taken and analyzed by HPLC in coupling with an Acclaim RSLC C18 column and detected at 280 nm. After 16 hrs fermentation, almost no styrene was found in medium, but high concentration of styrene can be found in butanol. Compared to the control that only contains the fusion of PAL2 and FDC, the clone containing triple genes (fusion of PAL2 and FDC plus srpABC) was able to produce nearly four times more product, i.e. 521 mg/L vis. 139 mg/L. (See FIG. 17).

Example V. Biosynthesis of Styrene

Production of Styrene from Glucose.

Figure 18A:
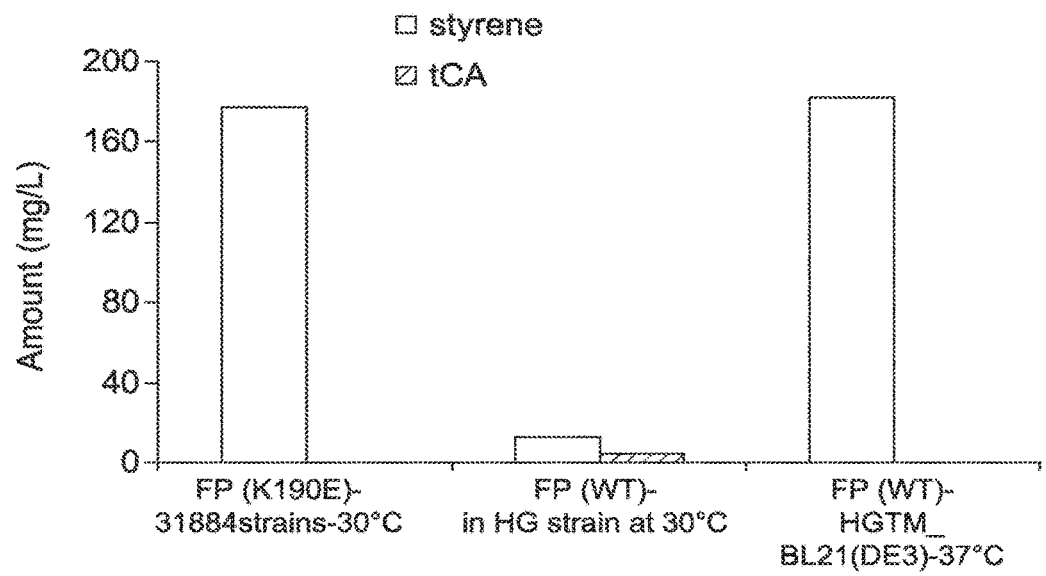
FIG. 18A shows the production of styrene and tCA from glucose.

A vector comprising fusion protein FDC1(K190E)-PAL was constructed, transformed it into phenylalanine producing strains (ATCC 31884 and HG), which was grown in LB containing ampicillin and/or kanamycin. The cultures were grown at 30° C. for 12 hours, after that the cultures were harvested and an aliquot of cultures were inoculated in M9 medium. The cultures were grown at 30° C. until the $OD_{600}$ reached to 0.8 and then they were induced with 0.2 mM IPTG and continued to culture at 30° C. or 37° C. for 48 hrs. The volatile styrene was collected by STRATA-X® column. The amount of phenylalanine, tCA, and styrene was measured by HPLC. The ATCC 31884 strains produced 177 mg/L of styrene from glucose at 30° C.; no accumulation of tCA or phenylalanine was observed (FIG. 18A). The HG strain produced 13.1 mg/L of styrene and 5.0 mg/l of tCA from glucose at 30° C., no accumulation of phenylalanine was observed (FIG. 18A).

Interestingly, the BL-21(DE3) strains produced 182 mg/L of styrene from glucose by co-expression of FDC-PAL fusion protein and phenylalanine producing vector (HGTM) at 37° C. The whole system for production of styrene from glucose is transferable to any host system.

STRATA-X® column produced 25 fold higher styrene (125 mg/L), as compared with that of in anaerobic condition and in absence of STRATA-X® column (5 mg/L), when FDC-PAL produced styrene from phenylalanine. STRATA-X® column maintain aerobic condition, trap volatile styrene and remove styrene that ultimately increase styrene production and remove toxicity effect on culture.

Production of Styrene from Trans-Cinnamic Acid or L-Phenylalanine.

The nucleotides encoding FDC wild type, FDC mutant (K190E), FDC (WT)-PAL fusion protein, and FDC (K190E)-PAL fusion protein were transformed in E. coli BL-21 (DE3). The cells were grown in LB at 30° C. for overnight. The cells were harvested and washed with M9 media. The cells were inoculated to 2.0 ml M9 media with the initial OD600 at 0.3 and were cultured at 30° C. until the OD600 of the culture reached to 0.6 to 0.8. The cells were then induced with 0.2 mM IPTG for 8.0 hours at 30° C. The cells transformed with FDC wild type and FDC (K190E) were fed with 0.1% trans-cinnamic acid. The cells transformed with FDC (WT)-PAL and FDC (K190E)-PAL fusion proteins were fed with either 0.1% trans-cinnamic acid or 0.1% L-phenylalanine. The fed cells were continuously cultured for 36 hours. STRATA X column was used to collect styrene. The product was eluted from the column by butanol and the amount was quantified by HPLC.

Figure 18B:
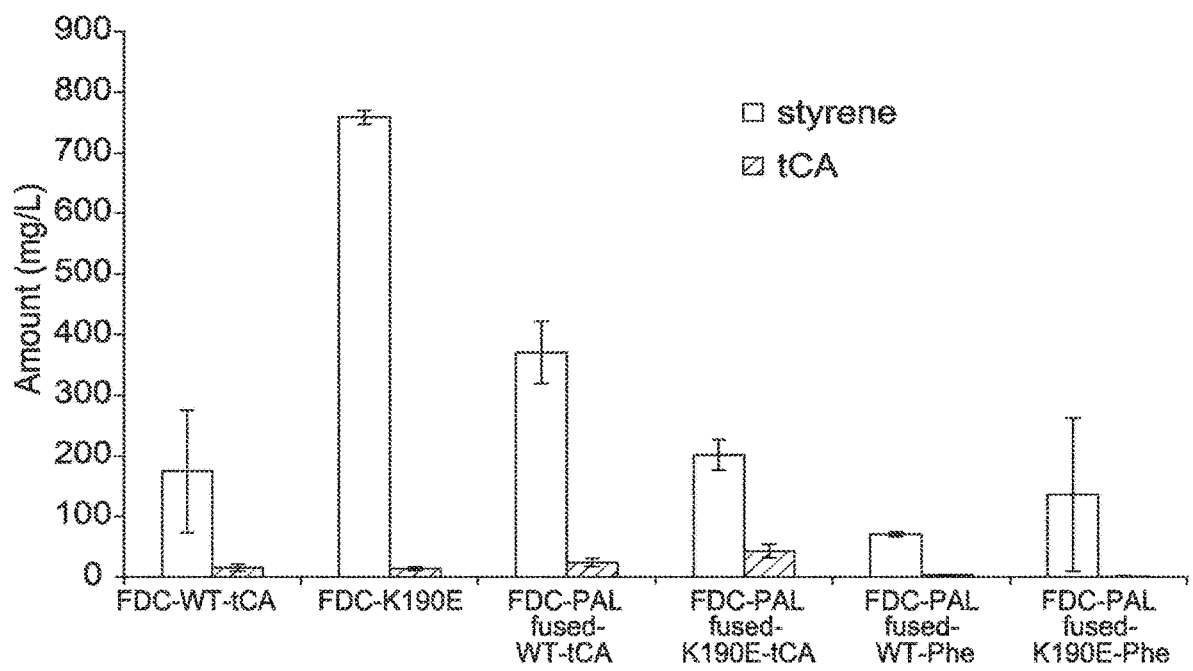
FIG. 18B shows production of styrene from trans-cinnamic acid or phenylalanine.

As shown in FIG. 18B, the cells transformed with FDC (K190E) mutant produced higher amount of styrene (758 mg/L) than that of FDC wild type (175 mg/ml). In comparison, FDC(K190E) fused with PAL produced slightly lower amount of styrene from either trans-cinnamic acid or L-phenylalanine than that produced by FDC wild type fused with PAL.

Example VI. Purification of Cinnamic Acid Decarboxylase for Crystallization

An expression vector of FDC1 that has 6-His and SUMO at the N-terminal end was constructed. The DNA encoding FDC1 were transformed into *E. coli* (Rosetta 2) competent cells and grown in LB containing ampicillin. The cultures were grown in LB at 37° C. for overnight. The cultures were inoculated in terrific-broth media and grown at 37° C. until the $OD_{600}$ reached 0.8 to 1.0 at which point IPTG was added to a final concentration of 0.2 mM, and continued to culture at 16° C. for 16 hours. Cells were harvested by centrifugation for 15 minutes at 4° C. at 4500 rpm. The cell pellet was suspended in buffer A (50 mM potassium phosphate buffer, 50 mM sodium thiosulfate, 50 mM TCEP-HCl, 500 mM NaCl, 0.5 mM PMSF, 10 mM $MgCl_2$, 10 mM imidazole, 20 mM βME, and 20% glycerol adjusted to pH 7.5) containing 0.1% triton X-100, and 2 µg/mL DNAse, RNAse, and 4 µg/mL lysozyme. The cells were disrupted by ultra-sonication 10 times at amplitude 15, process time 5 seconds, 1 second pulse on/off. The supernatant was collected by centrifugation for 15 minutes at 15,000 rpm at 4° C. The supernatant was filtered through a 0.45 µM PES filter and applied to a $Ni^+$-agarose affinity column (GE Healthcare). The column was washed with buffer A until non-specific binding proteins eluted from the column. FDC1 was eluted with 50 mM potassium phosphate, 50 mM sodium thiosulfate, 50 mM TCEP-HCl, 500 mM sodium chloride, 0.5 mM PMSF, 10 mM magnesium chloride, 250 mM imidazole, 20 mM βME, and 20% glycerol adjusted to pH 8.0. A total of 45.0 mg protein was found after $Ni^+$-agarose affinity column.

Hydrolase (0.5 mg) was added to cleave SUMO from the FDC1. Digestion was carried out at 4° C. by dialysis of the protein overnight in 1 L of 25 mM potassium phosphate, 50 mM sodium thiosulfate, 500 mM NaCl, 5 mM DTT, and 20% glycerol adjusted to pH 7.5. Dialysis was continued in a fresh liter of dialysis buffer for 2-4 hours the next morning.

Subtractive Purification.

The $Ni^+$-agarose affinity column was washed with water, recharged with nickel sulfate and equilibrated with buffer A before loading the protein in the column. The protein was loaded in column, flow through was collected, and an addition 15 ml of buffer A was loaded which was collected as flow through. After all the FDC1 had been collected, the column was washed with elution buffer to remove SUMO and hydrolase from the column. The flow through containing FDC1 was combined and the amount of protein was measured. A total 27.5 mg was found after subtractive purification. The protein was dialyzed overnight in 1 L Q-column buffer A (25 mM potassium phosphate, 5 mM DTT, and 25 mm sodium thiosulfate adjusted to pH 7.5).

Anion-Exchange Chromatography.

The anion-exchange Q-column (GE Healthcare) was equilibrated with Q-column buffer A. The protein was loaded into the column, and washed with buffer A until all the non-specific binding proteins were eluted from the column. The protein was eluted with Q-column buffer A containing 1 M sodium chloride. Elution started at 27% Q-column buffer B. The fractions containing FDC1 were used for SDS-PAGE to check the purity of the protein. A total of 5.0 mg protein was found after anion-exchange chromatography. The protein was dialyzed overnight in size exclusion buffer (50 mM sodium phosphate pH 7.5, 150 mM NaCl, 5 mM DTT, and 25 mM sodium thiosulfate).

Size-Exclusion Chromatography.

Figure 20:
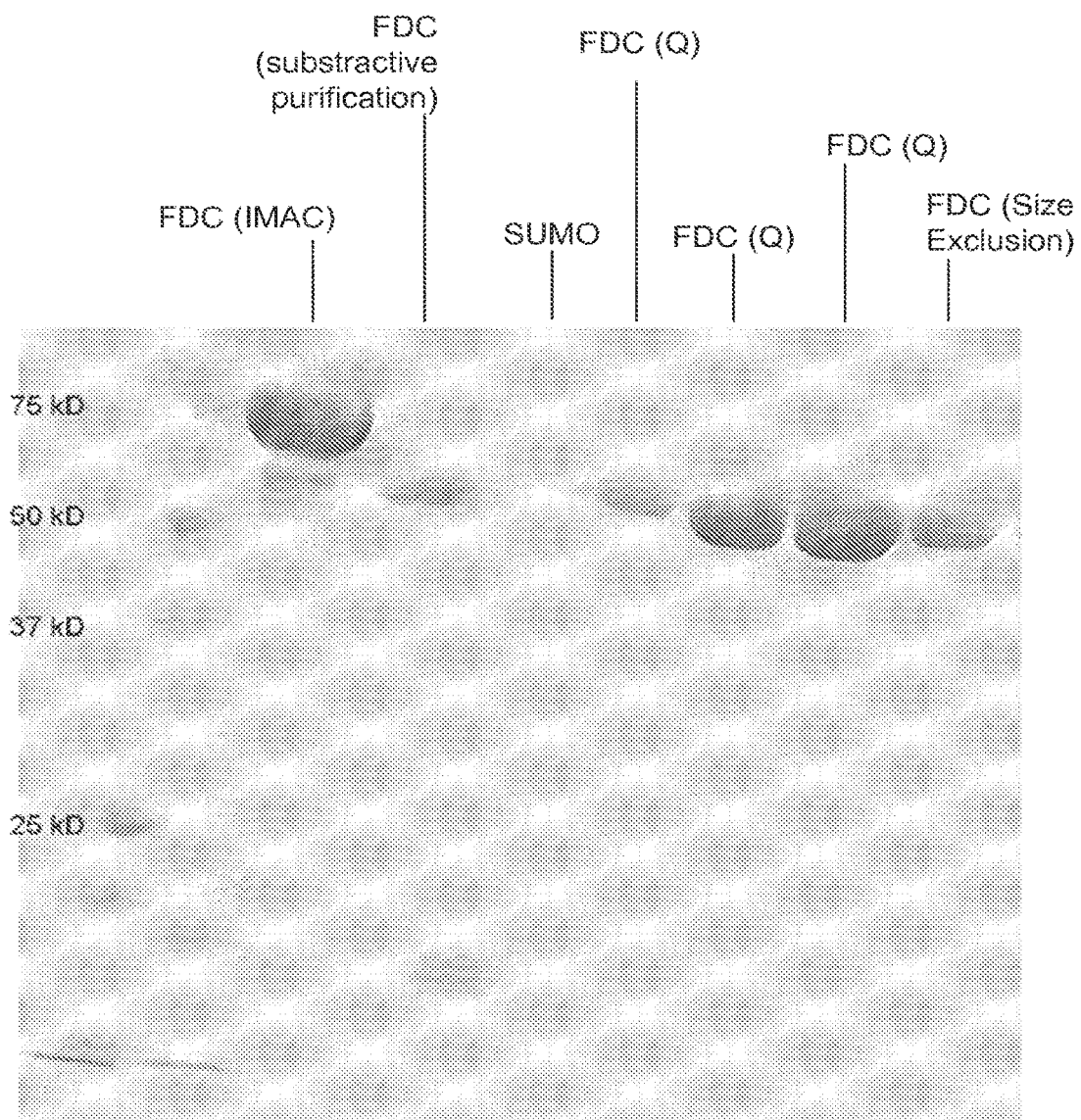
FIG. 20 shows the SDS-PAGE analysis of purified FDC1.

The protein was loaded onto the size exclusion column (GE Healthcare) and eluted with 50 mM sodium phosphate pH 7.5, 150 mM sodium chloride, 5 mM DTT, and 25 mM sodium thiosulfate. The fractions (tubes 33 through 38) containing FDC1 were combined and concentrated. A total of 3.5 mg purified protein was found after size-exclusion chromatography. The purity was checked by SDS-PAGE (FIG. 20). The protein was more than 98% pure and ready for crystallization.

Standard recombinant DNA and molecular cloning techniques used here are well known in the art and are described by Sambrook, J., Fritsch, E. F. and Maniatis, T. Molecular Cloning: A Laboratory Manual, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. Experiments with Gene Fusions; Cold Spring Harbor Laboratory: Cold Spring Harbor, N.Y., 1984; and by Ausubel, F. M. et al., In Current Protocols in Molecular Biology, published by Greene Publishing and Wiley-Interscience, 1987.

FDC mutants, for example, FDC (K190E) having an amino acid sequence as set forth in SEQ ID NO:16, can be purified by the same process as FDC1 as described above.

Example VII. Crystallization of Cinnamic Acid Decarboxylase

Crystals of mutant cinnamic acid decarboxylase FDC (K190E) in complex with 3-hydroxyl cinnamic acid were grown by the vapor diffusion method. Commercial screening Kit (Hampton research, Qiagen, Emerald Biosystems) was used for screening crystallization conditions. Different volume ratio of protein and reservoir were tested for crystallization. Hanging drops containing a 1:1, 1:2, or 2:1 mixture of protein (5-10 mg/ml) and crystallization buffer (10% (w/v) polyethylene glycol (PEG) 6000, 5% (w/v) 2-methyl-2,4-pantanediol (MPD), 0.1 M HEPES, pH 7.5, and 2 mM DTT) were maintained at 4° C. In particular, well diffracted crystals were grown in 7-11% (w/v) polyethylene glycol (PEG) 6000, 3% (w/v) 2-methyl-2,4-pantanediol (MPD), pH 6.5-7.5, and 2 mM DTT with 0.1% 3-hydroxyl cinnamic acid. Crystal conditions were further improved by adding 0.01M MnCl2, 0.5% (w/v) polyvinylpyrrolidone K15, 0.2M NDSB-201 or 2% (w/v) benzamidine hydrochloride as an additive.

Figure 21A:
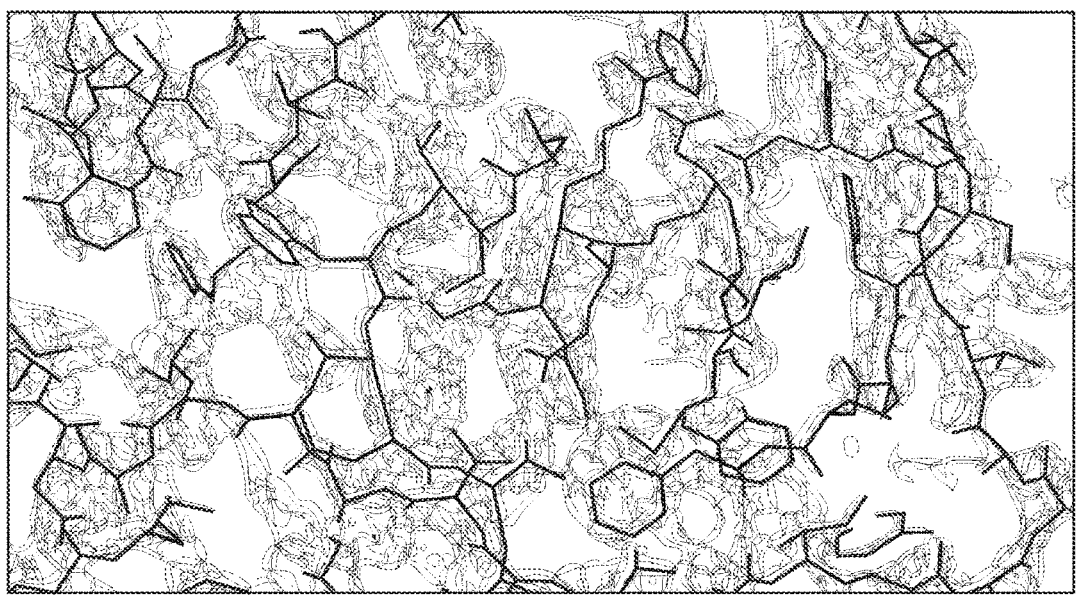
FIG. 21A shows a typical electron density map with initial model of the crystalline structure of FDC(K190E).
Figure 21B:
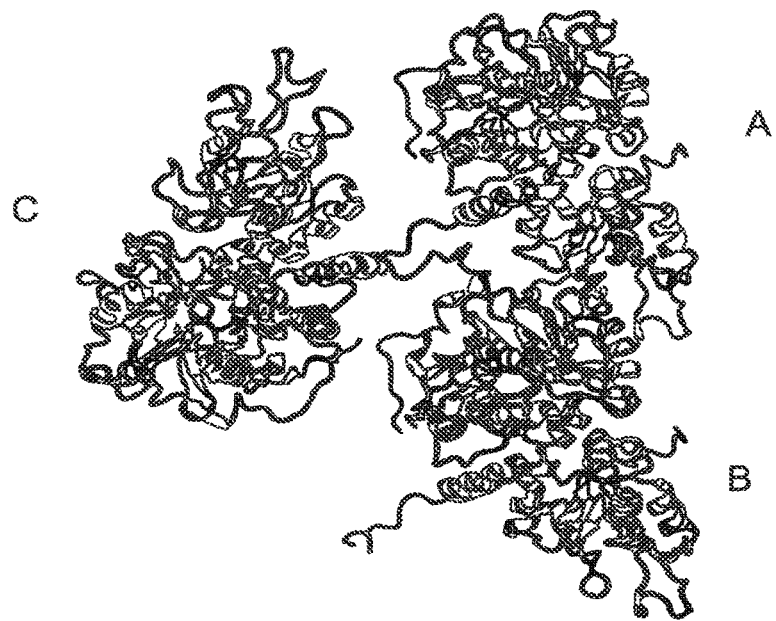
FIG. 21B shows an asymmetric unit of the crystalline structure of FDC(K190E).

The FDC(K190E) crystals grew in space group C2 with 3 chains per asymmetric unit. Unit cell dimensions for the crystal were a=249.51 Å, b=120.67 Å, c=158.49 Å, β=94.9°; Diffraction data were collected from single crystals mounted in a cryoloop and flash frozen in a nitrogen stream at 100 K and reduced with the HKL suite. Crystals were diffracted at 2.15 Å resolution. Molecular replacement (Phaser) in CCP4i suite was used to solve the structure of FDC(K190E) mutant using 3-octaprenyl-4-hydroxybenzoate decarboxylase (2IDB) structure as a model template. The initial model of the structures was built by manual building using the COOT and the model was refined using Refmac5. A typical electron density with current initial model of FDC is provided in FIG. 21A. An asymmetric unit of the crystal structure containing 3 chains is shown in FIG. 21B. As illustrated in FIG. 21B, FDC(K190E) molecules A and B form a dimer that is biologically active, and FDC(K190E) molecule C forms another dimer with its partner of another asymmetric unit (not shown).

The specification is most thoroughly understood in light of the teachings of the references cited within the specification. The embodiments within the specification provide an illustration of embodiments of the subject technology and should not be construed to limit the scope of the subject technology. The skilled artisan readily recognizes that many other embodiments are encompassed by the subject technology. All publications, patents, sequences (including sequences that are identified by GenBank accession numbers) cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the subject technology described herein. Such equivalents are intended to be encompassed by the embodiments.

What is claimed is:

1. A host cell comprising a cinnamic acid decarboxylase, wherein the cinnamic acid decarboxylase is a mutant cinnamic acid decarboxylase comprising the amino acid sequence as set forth in SEQ ID NO: 8 but with a mutation at an amino acid residue position selected from the group consisting of: 155, 156, 159, 162, 163, 164, 172, 173, 174, 175, 187, 188, 189, 190, 191, 192, 193, 194, 195, 196, 226, 227, 280, 285, 286, 287, 291, 326, 331, 360, 361, 395, 396, 398, 440, 441, and combinations thereof.

2. A host cell comprising: (a) a recombinantly expressed phenylalanine ammonia lyase; (b) a recombinantly expressed cinnamic acid decarboxylase; and (c) a recombinantly expressed membrane-bound transporter, wherein the cinnamic acid decarboxylase is a mutant cinnamic acid decarboxylase comprising the amino acid sequences as set forth in SEQ ID NO: 8 but with a mutation at an amino acid residue position selected from the group consisting of: 155, 156, 159, 162, 163, 164, 172, 173, 174, 175, 187, 188, 189, 190, 191, 192, 193, 194, 195, 196, 226, 227, 280, 285, 286, 287, 291, 326, 331, 360, 361, 395, 396, 398, 440, 441, and combinations thereof.

3. The host cell of claim 2, wherein the cinnamic acid decarboxylase comprises an amino acid sequence selected from the group consisting of: SEQ ID NO:16; SEQ ID NO:18; SEQ ID NO:20; SEQ ID NO:22; SEQ ID NO:24; SEQ ID NO:26; SEQ ID NO:28; SEQ ID NO:30; SEQ ID NO:32; SEQ ID NO:34; SEQ ID NO:36; and SEQ ID NO:38.

4. The host cell of claim 2, wherein the membrane-bound transporter is a bacterial ABC transporter.

5. A host cell comprising (a) a recombinantly expressed fusion protein comprising a first domain comprising a phenylalanine ammonia lyase, and a second domain comprising a cinnamic acid decarboxylase; and (b) a recombinantly expressed membrane-bound transporter, wherein the cinnamic acid decarboxylase is a mutant cinnamic acid decarboxylase comprising the amino acid sequence as set forth in SEQ ID NO: 8 but with mutation at an amino acid residue position selected from the group consisting of: 155, 156, 159, 162, 163, 164, 172, 173, 174, 175, 187, 188, 189, 190, 191, 192, 193, 194, 195, 196, 226, 227, 280, 285, 286, 287, 291, 326, 331, 360, 361, 395, 396, 398, 440, 441, and combinations thereof.

6. The host cell of claim 5, wherein the cinnamic acid decarboxylase is a mutant cinnamic acid decarboxylase comprising the amino acid sequence as set forth in SEQ ID NO: 8 but with a mutation at an amino acid residue position selected from the group consisting of 175, 190, and 193, and combinations thereof.

7. The host cell of claim 5, wherein the cinnamic acid decarboxylase comprises an amino acid sequence selected from the group consisting of: SEQ ID NO:16; SEQ ID NO:18; SEQ ID NO:20; SEQ ID NO:22; SEQ ID NO:24; SEQ ID NO:26; SEQ ID NO:28; SEQ ID NO:30; SEQ ID NO:32; SEQ ID NO:34; SEQ ID NO:36; and SEQ ID NO:38.

8. The host cell of claim 5, wherein the phenylalanine ammonia lyase comprises an amino acid sequence selected from the group consisting of: SEQ ID NO: 2, SEQ ID NO:4, and SEQ ID NO:6.

9. The host cell of claim 5, further comprising a linker covalently linking the first domain and the second domain.

10. The host cell of claim 9, wherein the linker is a peptide linker comprising 2 to 15 amino acids.

11. The host cell of claim 10, wherein the peptide linker is comprised of glycine and serine amino acids.

12. The host cell of claim 10, wherein the linker is selected from the group consisting of: GS, GSG, SEQ ID NO: 39, SEQ ID NO: 40, SEQ ID NO: 41, SEQ ID NO: 42, SEQ ID NO: 43, and SEQ ID NO:44.

13. The host cell of claim 5, wherein the recombinantly expressed membrane-bound transporter is a bacterial ABC transporter.

14. The host cell of claim 5, wherein the recombinantly expressed membrane-bound transporter is a solvent resistant efflux pump protein.

15. The host cell of claim 14, wherein the solvent resistant efflux pump protein is derived from *Pseudomonas putida*.

16. A method for the production of styrene, the method comprising:
    (a) contacting the host cell of claim 5 with a fermentable carbon substrate; and
    (b) culturing the host cell in a culture medium for a time sufficient to produce styrene.

17. The method of claim 16, wherein said styrene is produced in the state of vapor, and said vapor is absorbed by an absorbing material.

18. The method of claim 17, wherein the absorbing material is selected from the group consisting of polymeric resin, activated carbon, cellulosic material, and combination thereof.

19. The method of claim 18, wherein the polymeric resin is a hydrophobic resin.

20. The method of claim 18, wherein the polymeric resin is selected from the group consisting of C18, C8, phenyl, SDB-L sorbents resins, and combination thereof.

* * * * *